United States Patent [19]

Hou et al.

[11] Patent Number: 4,791,063

[45] Date of Patent: Dec. 13, 1988

[54] POLYIONENE TRANSFORMED MODIFIED POLYSACCHARIDE SUPPORTS

[75] Inventors: Kenneth C. Hou, S. Glastonbury; Chung-Jen Hou, South Windsor; Haunn-Lin Chen, Vernon, all of Conn.

[73] Assignee: Cuno Incorporated, Meriden, Conn.

[21] Appl. No.: 758,064

[22] Filed: Jul. 23, 1985

Related U.S. Application Data

[63] Continuation-in-part of Ser. No. 576,448, Feb. 2, 1984, Pat. No. 4,663,163, which is a continuation-in-part of Ser. No. 466,114, Feb. 14, 1983, abandoned.

[51] Int. Cl.$^4$ .......................... C12N 1/00; C08F 1/00
[52] U.S. Cl. ............................. 435/243; 435/252.1; 435/254; 435/287; 435/803; 524/27; 524/58; 525/54.3; 526/238.2

[58] Field of Search .................. 524/27, 58; 435/178, 435/179, 803, 243, 253, 287, 254; 525/54.3; 526/238.2

[56] References Cited

U.S. PATENT DOCUMENTS

| | | | |
|---|---|---|---|
| 3,438,915 | 4/1969 | Girard | 524/27 |
| 4,048,377 | 9/1977 | Boschetti et al. | 524/58 |
| 4,172,057 | 10/1979 | Henbest | 524/58 |
| 4,192,783 | 3/1980 | Bomball et al. | 524/58 |
| 4,192,785 | 3/1980 | Chen et al. | 524/27 |

*Primary Examiner*—Sam Rosen
*Attorney, Agent, or Firm*—Weingram & Zall

[57] ABSTRACT

Polyionene-transformed modified polymer-polysaccharide separation matrix and use thereof in removing contaminants of microorganism origin from biological liquids are disclosed.

55 Claims, 13 Drawing Sheets

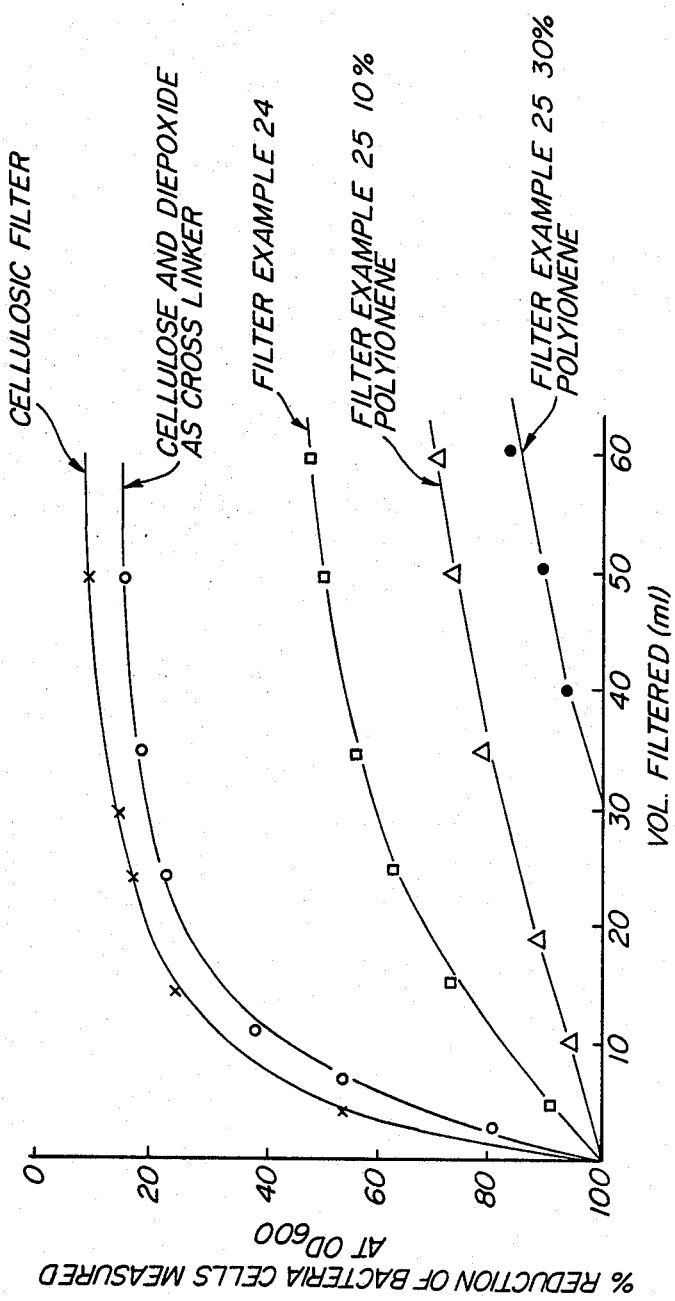

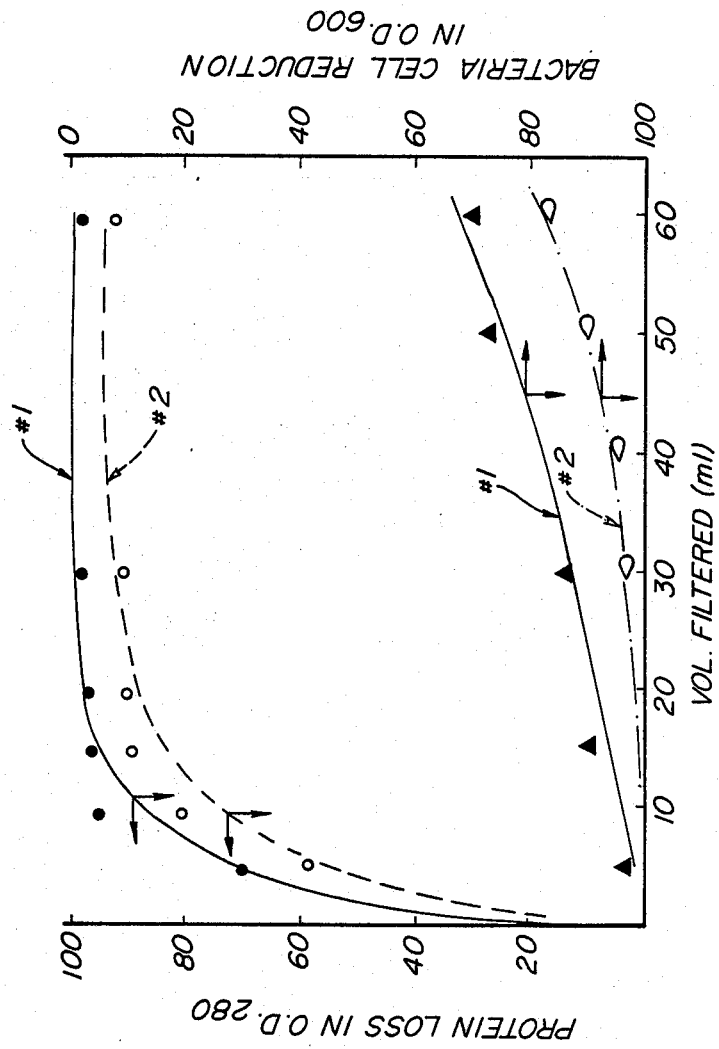
FIG-18 BACTERIA ADSORPTION BY AMF FILTERS IN HUMAN SERUM

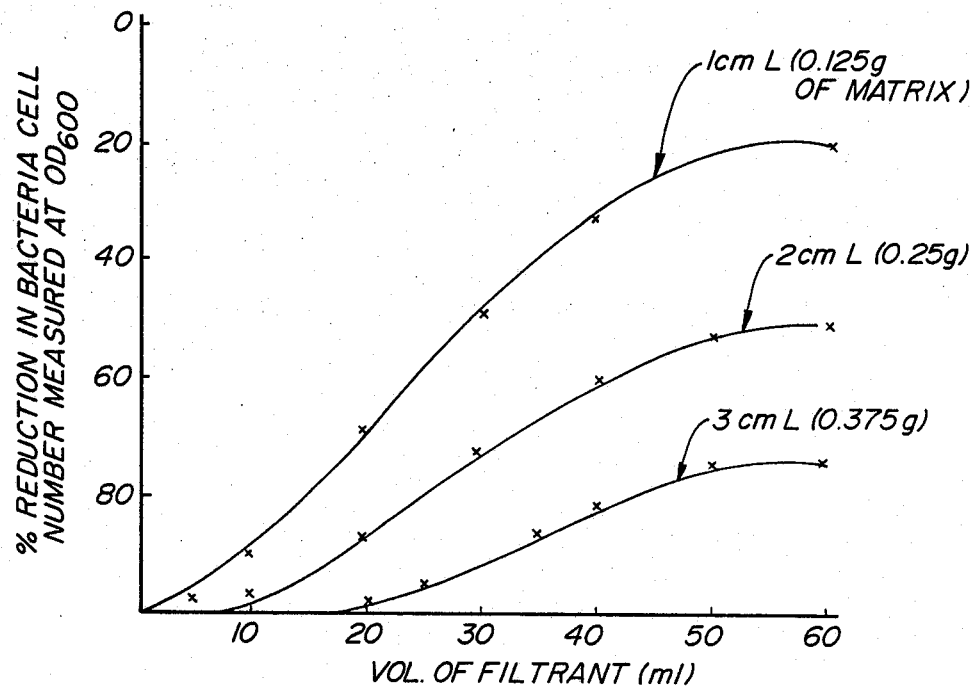

POLYIONENE TRANSFORMED MODIFIED POLYSACCHARIDE SUPPORTS

CROSS REFERENCE TO RELATED APPLICATIONS

The present application is a continuation-in-part of application Ser. No. 576,448, filed Feb. 2, 1984 now U.S. Pat. No. 4,663,163, which in turn is a continuation-in-part of application Ser. No. 466,114, filed Feb. 14, 1983 now abandoned. Further, the application is related to application Ser. No. 723,691, filed Apr. 16, 1985 now U.S. Pat. No. 4,675,104, (which is a continuation-in-part of Ser. No. 633,904, filed Jan. 23, 1985, abandoned, which is a continuation of Ser. No. 505,532, filed June 17, 1983, now U.S. Pat. No. 4,496,461) and application Ser. No. 758,036, filed concurrently herewith. These patent applications are incorporated by reference herein.

BACKGROUND OF THE INVENTION

1. Field of the Invention

The present invention relates to separation matrices useful for removing microorganism-originated contaminants from biological liquids and methods for their preparation and use. The separation matrices may be used as chromatographic separation media as well as providing the added benefit of antimicrobial activity and are characterized by the presence of immobilized polyionene.

2. Brief Description of the Background Art

The broad applicability of ion exchange chromatography, which ranges from separation of inorganic and organic ions to that of protein molecules and other biomolecules, has made it a powerful and versatile tool for chemical and biochemical separations. The technique was originally limited to the use of natural products such as cellulose, clay and other minerals containing mobile ions that would exchange with ionic materials in the surrounding solute phase. Because of the low exchange capacity of these natural products, however, practical utilization thereof was limited, and synthetic organic polymers capable of exchanging ions were developed.

Among the first generation of synthetic ion exchange materials were the ion exchange resins. The fundamental framework of these ion exchange resins is an elastic three-dimensional hydrocarbon network comprising ionizable groups, either cationic or anionic, chemically bonded to the backbone of a hydrocarbon framework. The network is normally fixed, insoluble in common solvents and is chemically inert. The ionizable functional groups attached to the matrix carry active ions which can react with or can be replaced by ions in the solute phase. Therefore, the ions in the solute phase can be easily exchanged for the ions initially bound to the polymeric resins. Typical examples of commercially available ion exchange resins are the polystyrenes crosslinked with DVB (divinylbenzene), and the methacrylates copolymerized with DVB. In the case of polystyrene, a three-dimensional network is formed first, and the functional groups are then introduced into benzene rings through chloromethylation. Since ion exchange resins are elastic three-dimensional polymers, they have no definite pore size; only a steadily increasing resistance to flow of the polymer network limits the uptake of ions and molecules of increasing size.

The resistance to flow exhibited by these resins is controlled by the degree of crosslinking. With a low degree of crosslinking, the hydrocarbon network is more easily stretched, the swelling is large, and the resin exchanges small ions rapidly and even permits relatively large ions to undergo reaction Conversely, as the crosslinking is increased, the hydrocarbon matrix is less resilient, the pores of the resin network are narrowed, the exchange process is slower, and the exchanger increases its tendency to exclude large ions from entering the structure. The ion exchange resins made from polymeric resins have been successfully applied for the removal of both organic and inorganic ions from aqueous media but they are normally unsuitable for the separation of biopolymers such as proteins. This is due, among others, to the following reasons:

(1) The highly crosslinked structure of the resins has rather narrow pores to accommodate the diffusion of proteins; the proteins therefore are virtually restricted to the macrosurface area of the beads with consequent limitation of solute loadings;

(2) The high charge density close to the proximity of the resin surface is unsuitable, since it causes excessive binding and distortion of protein structure;

(3) The hydrocarbon matrix is usually hydrophobic and is potentially dangerous to the subtle three-dimensional structure of biopolymers, often causing denaturation of proteins.

The next generation of chromatographic materials useful for separation of proteins and other labile biological substances was based on cellulose ion exchangers. These lacked nonspecific adsorption and had practicable pore structure. Such prior art ion exchange celluloses are made by attaching substituent groups with either basic or acidic properties to the cellulose molecule by esterification, etherification, or oxidation reactions. Examples of cationic exchange celluloses are carboxymethylated cellulose (CM), succinic half esters of cellulose, sulfoethylated cellulose, and phosphorylated cellulose. Examples of anionic exchange celluloses are diethylaminoethyl cellulose (DEAE), and triethylaminoethyl cellulose (TEAE). Ion exchange materials based on cellulose as the principal backbone or anchoring polymer, however, have not enjoyed complete success due primarily to an inherent property of cellulose: its affinity for water. Thus, prior art ion exchange materials based on cellulose, while typically having high exchange capacity, are difficult to use as a consequence of their tendency to swell, gelatinize or disperse on contact with an aqueous solution. An ideal ion exchange material should minimally interact with the solvent system which carries the ions in solution through its pores; only in this manner is it possible to obtain a rapid, free flowing ion exchange system.

A third generation of ion exchange materials, which were developed to solve some of these problems, were the ion exchange gels. There gels comprise large pore gel structures and include the commercially known material Sephadex ®, which is a modified dextran. The dextran chains are crosslinked to give a three-dimensional polymeric network. The functional groups are attached by ether linkages to the glucose units of the dextran chains. Proteins are not denatured by the hydrophilic polymeric network. Sephadex ® exhibits very low nonspecific adsorption, which makes it ideal as a matrix for biological separations. However, the porosity of ion exchange gels is critically dependent on its swelling properties, which in turn is affected by the environmental ionic strength, pH and the nature of the counter-ions. Swelling of gels in buffer is caused primarily by the tendency of the functional groups to become hydrated. The amount of swelling is directly proportional to the number of hydrophilic functional groups attached to the gel matrix, and is inversely proportional to the degree of crosslinking present in the gel. This characteristic swelling is a reversible process, and at equilibrium there is a balance between two forces: (1) the tendency of the gel to undergo further hydration, and hence to increase the osmotic pressure within the gel beads, and (2) the elastic forces of the gel matrix. The osmotic pressure is attributed almost entirely to the hydration of the functional groups, and, since different ions have different degrees of hydration, the particular counter-ions in an ion exchange gel can be expected to have a considerable influence upon the degree of swelling. Since the pH, the electrolyte concentration and the nature of the counter-ions can all affect the hydration, leading to a different degree of gel swelling, the pore size in the gels is not in well defined form but is rather dependent on the environmental conditions. Gels without crosslinking provide large pores and high capacity due to maximum swelling. They suffer, however, from the weakness of structural integrity and can easily be crushed with a minimum amount of pressure. Removal of the solvent from the gels often results in collapse of the matrix. Highly crosslinked gels have mechanical strength, but lose capacity and pore size due to restrictions in swelling.

Ion exchange gels made from synthetic polymers have also been used, and they include crosslinked polyacrylamide (Bio-Gel P ®), microreticular forms of polystyrene (Styragel ®), poly(vinyl acetate) (Merck-o-Gel OR ®), crosslinked poly(2-hydroxy ethylmethacrylate)(Spheron ®), and polyacryloylmorpholine (Enzacryl ®). All of these follow the general trend: it may be possible to obtain dimensional stability with high flow rate or, alternatively, high capacity with swelling. It is, however, not possible to obtain both capacity and high flow rate at the same time.

The failure of single components to have both capacity and dimensional stability led to yet another generation of ion exchange materials comprising composite structures, e.g., hybrid gels. Hybrid gels are made by combining a semi-rigid component, for the purpose of conferring mechanical stability, with a second component, a softer network, which is responsible for carrying functional groups. Agarose gel, which would otherwise be very soft and compressible, can be made stronger through hybridizing with crosslinked polyacrylamide. The crosslinked polyacrylamide component is mechanically stronger than the agarose, improves the gel flow properties, and reduces the gel swelling, but it sacrifices molecular fractionation range. Examples of hybrid gels other than polyacrylamide/agarose (Ultrogels ®), are polyacryloylmorpholine and agarose (Enzacryl ®), and composite polystyrenes with large pore polystyrenes as a framework filled with a second type of lightly crosslinked polymer.

Yet another composite gel structure is achieved by combining inorganic materials coated with organics, and are the types known as Spherosil ®. Porous silica beads are impregnated with DEAE dextran so that the product will have the mechanical properties of silica, with the ion exchange properties of DEAE dextrans. These composites, however, have severe channeling defects arising out of particle packing, and they have capacity limitations on the coated surfaces.

Totally rigid inorganic supports such as porous silica or porous glass which are not susceptible to degradation have also been used to provide high porosity, and high flow rate systems. The major problem, however, is nonspecific adsorption of proteins due to the silanol groups on the silica surface. Since the hydrolysis of silica is directly related to the pH conditions, the nonspecific adsorption by silica is minimal at neutral pH, but increases as the pH changes both to the acidic or alkaline ranges. A monolayer coating by either hydrophilic organic polymers or silanization has been used in an attempt to overcome this problem.

In the technique of affinity chromatography, which enables the efficient isolation of biological macromolecules or biopolymers, by utilizing their recognition sites for certain supported chemical structures with a high degree of selectivity, the prior art has also utilized materials of varying chemical structure as supports. For example, agarose gels and crosslinked agarose gels have been the most widely used support materials. Their hydrophilicity makes them relatively free of nonspecific binding, but their compressibility makes them less attractive as carriers in large scale processing, such as in manufacturing. Controlled-pore glass (CPG) beads have also been used in affinity chromatography. Although high throughputs can be obtained with columns packed with CPG, this carrier is even more expensive than agarose gel beads. Cellulose particles have also been used by immunochemists for synthetic affinity sorbents. However, compared to agarose gels, cellulose particles are formed with more difficulty and therefore, have received less attention in the preparation of affinity sorbents for enzymes. Cellulose, however, is perhaps the least expensive of all support matrices. Two lesser used support matrices are polyacrylamide gel beads and Sephadex ® gel beads made from dextran and epichlorohydrin. Although convenient methods have been developed for using them, the softness of these beads yields poor column packings, and their low molecular porosity yields a sorbent with poor ligand availability to the ligate.

Coupek et al., U.S. Pat. No. 4,281,233 show supports for affinity chromatography which comprise copolymers of hydroxy alkyl acrylates or methacrylates with crosslinking monomers. The copolymers contain covalently attached mono- or oligosaccharides. (An oligosaccharide is defined in the art as having up to nine saccharide units. See, e.g., Roberts, J. D., and Caserio, M. C., *Basic Principles of Organic Chemistry*, 1964, p. 615.)

A carrier for bio-active materials is also disclosed in Nakashima et al., U.S. Pat. No. 4,352,884. The Nakashima carrier comprises a substrate coated with a copolymer. The substrate may be one of various materials, including inorganic materials such as glass, silica, alumina, synthetic high polymers such as polystyrene, polyethylene and the like, and naturally occurring high polymers such as cellulose. The copolymer is made of a hydrophilic acrylate or methacrylate monomer which is a hydroxy or alkoxy alkyl acrylate or methacrylate, and a copolymerizable unsaturated carboxylic acid or amine. The base material or substrate is coated with the copolymer by conventional coating or deposition procedures, such as spraying, dipping, phase separation or the like. The copolymer may also contain small amounts of a crosslinking agent such as glycidyl acrylate or methacrylate. The crosslinking agent allows for crosslinking treatment after the coating process, and provides for the prevention of elution (presumably of the bioactive materials) from the coating layer. The amounts of cross-linking agent are quite small, and range between 0.5 and 1 percent by weight of the total copolymer weight. Such amounts of cross-linking agent are insufficient to cause substantial covalent bonding or grafting of the copolymer onto the underlying substrate. The copolymer in Nakashima is thus essentially only physically coating the underlying substrate. Physical coating, however, is accompanied by a series of problems. The carrier would not be expected to have an even distribution of the copolymer, would show a multilayered structure, and may have a possible uneven distribution of functional groups.

Another reference of interest is Kraemer, U.S. Pat. No. 4,070,348, which shows copolymers of glycidyl- and amino-containing acrylates, useful as carriers for biologically active substances, such as polysaccharides, enzymes, peptides, hormones, etc. The structure of the final product in Kraemer is that of an acrylic copolymer chain covalently modified at a multiplicity of sites thereon with substances such as enzymes, proteins, and the like.

This review of the prior art, its advantages and drawbacks, leads to the conclusion that there exists a need for a support useful both for ion exchange and affinity chromatography-based purification which will have high stability, high porosity, low nonspecific adsorption, high flow rate, poor compressibility, controlled gelation, and which will be useful for industrial-scale biological separations. It is at the industrial level of manufacturing, especially, where the aforementioned drawbacks have had their most important effect and where this need is the strongest.

Industrial scale molecular separation materials comprising fibrous matrices with particulate immobilized therein have been described in commonly assigned U.S. Pat. No. 4,384,957 to Crowder, which is herein incorporated by reference. This patent describes a composite fiber material formed by wet layering a sheet from an aqueous slurry of particulate, small refined fiber pulp and long soft fiber pulp. The purpose of the soft long fiber is physically to hold clumps of particulate material and refined pulp together. Sheets are formed from a wet slurry by vacuum filtration, wherein the long fibers form in a plane which is perpendicular to the direction of flow of the chromatographic carrier fluid. This permits channels to form in the composite material which are perpendicular to the direction of flow of the chromatographic carrier fluid and allows these materials to serve as internal flow distributors. The resulting matrix structure has proven to be an effective way of eliminating channeling defects through internal flow distribution mechanisms.

It is inevitable in prior art wet slurrying processes with slurries comprising cationic materials, to obtain materials having uneven distribution of charges, wherein multilayer coating may occur in one spot, whereas other spots on the surface may be bare. Such products are acceptable in filtration processes due to the fact that the amount of impurities needed to be removed is relatively small compared to the bulk liquid volume, and that uneven charge distributions can be compensated by the depth of the filters. However, such products cannot readily be applied to delicate ion exchange processes. The number of active sites, as well as the accessibility of the active sites, is critical to the capacity of such process. The chemical functional groups in ion exchangers cannot be buried close to the surface, but have to be somewhat removed from the surface, possibly with a molecular side arm for accessibility. One way of achieving this has been through the incorporation into the fibrous matrix of silanes which are chemically modified. Such silanes may carry functional groups such as DEAE, CM or affinity chromatography sites. They are mechanically stable and strong and do not swell. However, they are expensive, and show very high nonspecific adsorption of protein by the silica hydroxy groups.

In sum, neither the ion exchange nor affinity chromatography supports commonly used in laboratory scale purifications, nor the particulate (or ion exchange modified particulate) containing fibrous matrices for chromatography or filtration have proven to be of great use in scale-up of delicate purification processes.

A need therefore continues to exist for supports useful in industrial scale ion exchange and affinity chromatography purification processes, which will be noncompressible, controllably swellable, have high exchange capacity, exhibit high flow rates, be versatile and be relatively inexpensive to produce. Recognizing this need, Hou et al. developed the invention embodied in the aforementioned application Ser. Nos. 466,114 and 576,448.

Purification of protein from bacteria contamination remains a recalcitrant problem in bioprocess. Hou et al, U.S. Pat. No. 4,361,486, discloses a bacteriocidal filter media which comprises an amount of metal peroxide immobilized in a substantially inert porous matrix. Both gram-positive and gram-negative bacteria are negatively charged, mainly owing to an excess of carboxyl and phosphate groups. Gram-positive bacteria contain both teichoic and teichuronic acids in their walls, whereas gram-negative organisms have phospholipids, with the negatively charged lipid portion of lipopolysaccharides as components of their outer membranes. In aqueous environments, the cell membrane exists as a continuum of lipid and protein, organized as a molecular double layer, with the hydrophobic portions of the lipid molecule being opposed and the hydrophilic groups projecting outwardly into the aqueous phase.

Phosphoglycerides account for about half the lipids, with polar groups, such as glycerol, serine, and carboxyl providing the hydrophilic components. While various forms of proteins are embedded in the lipid, the major determinants of charge are surface polysaccharides covalently linked to the membrane proteins and lipids.

The effectiveness of bacteria removal through charge interaction has been previously demonstrated, for example, by Ostreicher et al., U.S. Pat. Nos. 4,305,782 and 4,473,474 and Barnes, U.S. Pat. No. 4,473,475. Capture of bacteria, endotoxins, and viruses by charge modified filters are described in *Applied and Environmental Microbiology*, 40: 892-896 (1980). Positively charged ion exchange resins have been utilized for bacteria adsorption (Daniels, S. L., *Development and Industrial Microbiology*, 13: 211-253 (1972)).

Olson et al, U.S. Pat. No. 4,411,795 describes a variety of polymers attached to substrates including cellulose and recognized that the combined effect of hydrophobic and ionic binding enhances adsorption of lipnin-containing cells.

Zvaginstev, D. G. et al., *Mikrobiologiya* 40: 123–126 (1971), concluded that adsorption of bacterial cells by ion exchange resins was attributable to electrostatic attraction between quaternary ammonium groups on the resin surface and carboxyl groups on the bacteria cell surface. Hogg, in his Ph.D. thesis for the University of Salford, England (1976), demonstrated the interaction of bacteria with cellulose-based DEAE. The adsorption of several gram-negative organisms was shown, including *Escherichia coli, Salmonella typhimurium,* and *Pseudomonas aeruginosa.*

The major forces impacting on bacterial adhesion to solid surfaces have been summarized by Rutter, P. R. in "The Physical Chemistry of the Adhesive of Bacteria and Other Cells," (1980) *Microbial Adhesion to Surfaces,* Editors Berkley et al., Ellis Howard Ltd., Publishers, West Sussex, England. According to Rutter, the Van der Walls force and charge interaction may be considered as long range forces. Where the distance between bacteria and solid surfaces are short, other interactions must be taken into account, for example, ion-dipole, dipole-dipole, hydrogen bonding, etc. The short range effects are particularly important in aqueous systems. When the bacteria particles approach the microscopic solid surface, the local ordered water structure near the surface must be broken down. This leads to a short range repulsion force, which may be sufficient to prevent the bacteria from coming closer to the solid surface. On the other hand, when both the surfaces involved are hydrophobic, the short range interaction is a net attraction. This energy favorable process, called "hydrophobic interaction", is the basis for the well-known high performance liquid chromatography applied in protein separations. As is known, a hydrocarbon chain of optimum length, when attached covalently to a solid matrix, may adsorb one protein in preference to another due to the difference in hydrophobicity between proteins.

However, an overly strong hydrophobic solid surface may uncoil the protein structure leading to the exposure of hydrophobic regions and increase tendency for hydrophobic interaction. If the uncoiling is too extensive, denaturation of the protein may result.

In most of the practical applications for bacteria and endotoxin inactivation and removal from biological and pharmaceutical products, protein contamination by bacteria is the most prevalent problem. One must be able to inactivate and remove the microorganism-originated contaminants from protein specifically without causing loss or denaturation of the final products. Accordingly, an optimal solid matrix should exhibit a hydrophobic force which just matches the surface hydrophobicity of proteins and maximally exploits these selected differences in such hydrophobicity.

Thus, a need has continued to exist for a solid matrix for removal of microorganism-originated contaminants from biological and pharmaceutical products which will effectively eliminate the contaminants without denaturing the final product.

Poly-quaternary ammonium polymeric polyelectrolytes are known to the prior art, these polymeric compositions produced by the polymerization of a dihalide and a ditertiary amine. These polymers are characterized by high charge density and have found substantial utility as flocculants in the clarification of residential and industrial water supplies, as catalysts in pigment retention additives, and as geling agents. These polyelectrolyte materials are also known to be useful in the rheological modification of fluids such as friction reducers, as dispersants for clay and sludge in both aqueous and oil-based systems, as anti-static agents, and as additives to cosmetics, textile finishes and lubricating oils. The materials are known to exhibit germicidal action or effective bactericidal and fungicidal agents. See Rembaum et al., U.S. Pat. No. 3,898,188.

Buckman et al., U.S. Pat. No. 3,784,649, discloses "high molecular weight" ionene polymeric compositions for utility, among others, as broad spectrum microbicides for efficient control of bacteria including sulphate reducers, fungi, algae, and yeast. The Buckman et al. polyionenes are suggested as additives to paper making systems, the polyionenes increasing production per unit of equipment, improving formation and strength properties of paper and paper board, and alleviating water pollution problems.

Rembaum, U.S. Pat. No. 4,046,750, discloses ionene modified beads for use in binding small and large anionic compounds. The bead substrates are formed by the aqueous copolymerization of a substituted acrylic monomer and a cross-linking agent. The formed polymeric beads are reacted with a mixture of a ditertiary amine and a dihalide or with a dimethylaminoalkyl halide to attach ionene segments to the halo or tertiary amine centers on the beads. The thus-formed polyionene-modified beads find use in affinity or pellicular chromatography for removal of heparin from its mixture with polycations or neutral substances such as proteins or serums. Further disclosed utilities include use of the modified beads in the separation of cholesterol precursors such as bile acid from bile micellar suspensions, for binding RNA or DNA irreversibly, and a variety of other utilities which depend upon the binding characteristics of the polycationic nature of the polyionene.

Rembaum, U.S. Pat. No. 4,013,507, discloses ionene polymers which bind negatively charged mammalian cells such as malignant cells for selectively inhibiting the growth in vitro thereof. Conversely, U.S. Pat. No. 3,910,819 to Rembaum et al. discloses the use of polyionene-coated containers for increasing the rate of cell growth.

U.S. Pat. No. 3,927,242 to Rembaum et al. discloses the use of polyionenes as coatings for paper substrates. Further disclosed are substrates coated with the polyelectrolyte to maximize the bactericidal activity of the polyionene. Suggested utilities include the impregnation of gauze material to form an antiseptic coagulant, germicidal dressing material.

U.S. Pat. No. 4,075,136 to Schaper discloses a class of ionene polymers which contain certain functional groups such as nitriles, acrylates, vinyl acetates, ketones, acrolein, acrylamides, methosulfates, sulfonic acids, pyridines, and pyrrolidones. A host of utilities are disclosed, including the use of the functional ionene polymers as biocides and as functional coatings on paper, for example, electroconductive, adhesive and photosensitive coatings.

In summary, polyionenes have been known and used for a substantial period of time and for a variety of purposes. However, the combination of polyionenes with the modified polysaccharide substrates of the present invention have not been suggested.

SUMMARY OF THE INVENTION

It is therefore an object of the invention to provide a novel molecular support.

Another object of the invention is to provide a molecular support useful for ion exchange chromatography, affinity chromatography or reverse phase chromatography.

Yet another object of the invention is to provide a chromatographic support useful for industrial scale chromatographic operations.

Still another object of the invention is to provide industrial processes of ion exchange, affinity chromatography, and reverse phase chromatography.

Yet another object of the invention is to provide processes for the preparation of ion exchange, affinity and reverse phase chromatographic supports.

This invention comprises a novel molecular support useful for ion exchange chromatography, affinity chromatography or reverse phase chromatography. The novel separation matrix provides chromatographic separation useful for industrial scale chromatographic operations, industrial processes of ion exchange, affinity chromatography, and reverse phase chromatography. This invention further comprises processes for the preparation of ion exchange, affinity and reverse phase separation matrices.

More specifically, the invention comprises a polyionene-transformed modified polysaccharide separation matrix, the modified polysaccharide comprising an insoluble polysaccharide covalently bonded to a synthetic polymer, said synthetic polymer made from (a) a polymerizable compound which has a chemical group capable of being covalently coupled directly or indirectly to said polysaccharide; and (b) one or more polymerization compounds containing (i) an ionizable chemical group, (ii) a chemical group capable of transformation to an ionizable chemical group, (iii) a chemical group capable of causing the covalent coupling of said polymerizable compound (b) to an affinity ligand or to a biologically active molecule, or (iv) a hydrophobic chemical group. Polymerizable compounds (a) and (b) may be the same or different. The thus-modified polysaccharide is then transformed by reactively bonding a polyionene thereto. The invention also comprises a process for preparing the polyionene-transformed modified polysaccharide, the process comprising polymerizing the monomers, grafting the polymerized monomers to the polysaccharide, and then reactively bonding the modified polysaccharide with polyionene. Separation matrices derived from the aforementioned polysaccharide materials are capable of acting as chromatographic supports for ion exchange chromatography, for affinity chromatography, reverse phase chromatography or as reagents for biochemical reactors. The thus-transformed modified polysaccharide demonstrates a two-phase adsorptive capability as a result of charge interaction with the microorganism-originated contaminant as well as hydrophobic interaction therewith. Additionally, the quaternary ammonium groups of the polyionene are biocidal.

The polyionene-transformed modified polysaccharide will, in addition, demonstrate biocidal and bacterial adsorption capabilities.

In order to put the theoretical aspects of protein interaction phenomena into practical use in a form of a separation device, a separation matrix was developed by taking the following steps:

1. formation of a hydrophilic physical structure with controlled high porosity as backbone material;

2. synthesis of a reagent for adsorption of contaminants of microorganism origin;

3. coupling or coating the reagent formed in step 2 to the physical structure of step 1.

The development of such separation matrices basically requires a physical structure of sufficient rigidity to sustain the high liquid flow without causing structural deformation, yet the pore has to be sufficiently large to accommodate the migration of large protein molecules without restriction. It must also be compatible with proteins yet chemically stable under different aqueous conditions. The invention of a matrix physical structure fulfilling such requirements has been fully disclosed in our previously filed pending application Ser. No. 576,448. The present invention provides an improvement thereon wherein the modified polysaccharide is transformed by reactively bonding thereto a polyionene polymer.

These separation matrices have been attained by providing:

A modified polysaccharide material, which comprises:

1. a polysaccharide covalently bonded to a synthetic polymer;

2. said synthetic polymer made from at least one of (a) a polymerizable compound which has a chemical group capable of being covalently coupled directly or indirectly to said polysaccharide; and (b) one or more polymerizable compounds containing (i) an ionizable chemical group, (ii) a chemical group capable of transformation to an ionizable chemical group, (iii) a chemical group capable of causing the covalent coupling of said polymerizable compound (b) to an affinity ligand or to a biologically active molecule, or (iv) a hydrophobic chemical group;

3. said modified polysaccharide having bonded thereto a polyionene.

Molecular separation materials derived from the aforementioned polysaccharide materials are capable of acting as chromatographic supports for ion exchange chromatography, for affinity chromatography, reverse phase chromatography or as reagents for biochemical reactors, wherein control of microorganisms-originated contaminants is essential.

BRIEF DESCRIPTION OF THE DRAWINGS

The present invention will become better understood by reference to the detailed description provided hereinafter when considered together with the accompanying drawings, wherein

FIG. 17 is a graph demonstrating the effectiveness of polyionene-transformed cellulose at separation of Salmonella G-130 from a liquid.

FIG. 18 is a graph demonstrating the effectiveness of polyionene-transformed modified cellulose at separation of Salmonella G-130 from biological fluids containing albumin.

FIG. 19 is a graph demonstrating the impact of column length on removal of bacteria from a liquid.

BRIEF DESCRIPTION OF THE PREFERRED EMBODIMENTS

The present invention is related to the discovery and development of materials useful as insoluble supports for a variety of applications including a wide range of chromatographic separations, i.e., affinity separations, or even as insoluble supports for bioreactors.

The support materials are based on a composite of an organic synthetic polymer and a polysaccharide which is subsequently transformed by bonding polyionene thereto. In its most used embodiment the composite per se is biologically inert. The organic synthetic polymer carries chemical groups which are capable of coupling to said polysaccharide, and also carries chemical groups which can provide ion exchange capacity, which can provide ion exchange capacity, which can provide anchoring capacity for affinity ligands or for biologically active molecules in general, or which can provide hydrophobic groups.

Strictly speaking, the polymer coupled to the polysaccharide may be either a copolymer or a homopolymer. When the chemical groups capable of coupling to the polysaccharide are the same as the chemical groups useful as anchoring units for affinity ligands or biologically active molecules, the polymer, in this particularly form would be a homopolymer. In another form, however, the polymer is a copolymer containing groups capable of coupling to the polysaccharide and also different groups capable of serving as anchoring groups for molecules.

The invention also relates to ion exchange materials obtained from the polyionene-transformed modified polysaccharide which are obtained by further reaction with crosslinking agents, and/or by further reactions such as chemical ionization, or unmasking of potentially masked ion exchange groups.

The invention also relates to materials derived from the polyionene-transformed modified polysaccharide by attaching thereto affinity ligands or biomolecules, to thereby obtain affinity chromatography or bioreactive materials, or attaching thereto hydrophobic substituents for reverse phase chromatography.

The invention also relates to mixtures of the aforementioned materials with unmodified polysaccharides, with modified or unmodified particulate material, or mixtures thereof to give a variety of separation media.

MATERIALS

The term "polysaccharide" as used in the specification and claims is meant to include compounds made up of many—hundreds or even thousands—monosaccharide units per molecule. These units are held together by glycoside linkages. Their molecular weights are normally higher than about 5,000 and up into the millions of daltons. They are normally naturally occurring polymers, such as, for example, starch, glycogen, cellulose, gum arabic, agar and chitin. The polysaccharide should have one or more reactive hydroxy groups. It may be straight or branched chain. The most useful of the polysaccharides for the purposes of this invention is cellulose.

The polysaccharide is preferably fully unprotected and carries all of its hydroxy groups in the free state. Some blocking of the hydroxy groups is possible, as for example by acylation or aminoacylation. Extensive blocking of the hydroxy groups of the polysaccharide, however, is undesirable since the polysaccharide thereby loses its hydrophilic character, which is necessary to provide appropriate chemically compatible interaction with biomolecules. If the polysaccharide becomes too hydrophobic, negative interactions with such molecules as proteins leads to possible non-specific bonding and denaturation phenomena. Also, if the masking of the polysaccharide hydroxy groups is too extensive, the reactivity of the resulting material with the polymer is greatly diminished. For all of these reasons, it is preferred to retain substantially all hydroxy groups in the free state. The polysaccharide may, however, be chemically activated, as seen infra.

Cellulose is the preferred polysaccharide. By "cellulose" is intended to mean any of the convenient and commercially available forms of cellulose such as wood pulp, cotton, hemp, ramie, or regenerated forms such as rayon. There exists no criticality as to the selection of a suitable form of cellulose. Cellulose is a naturally occurring polysaccharide consisting of beta -1,4- linked glucose units. In the native state, adjacent cellulose chains are extensively hydrogen bonded forming microcrystalline regions. These regions are interspersed by amorphous regions with less hydrogen-bonding. Limited acid hydrolysis results in preferential loss of the amorphous regions and gives so-called microcrystalline cellulose. The cellulose useful in the present invention is either cellulose in the native state, or in the microcrystalline state. Also, cellulose derived from cotton linter is better than that derived from wood pulp, as the latter contains lignin.

Figure 1A:
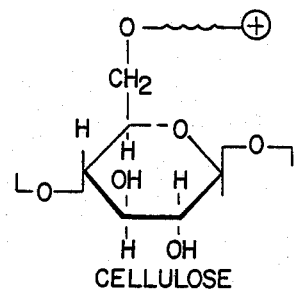
FIG. 1 is a diagram showing (A) an anion exchange cellulose derivatized by a prior art approach which yields one cationic site per saccharide unit and (B) an anion exchange cellulose derivatized by the approach of the invention which yields multiple cationic sites per saccharide unit.
Figure 1B:
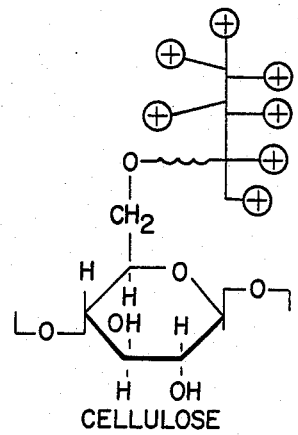
Figure 2:
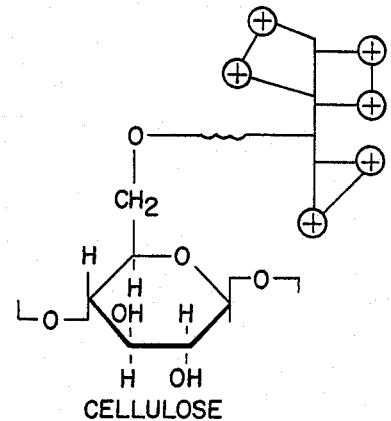
FIG. 2 shows the derivatized anion exchange cellulose of FIG. 1(B) after further cross-linking or quaternization.

Chemical reactions to attach the polymer to the polysaccharide material normally proceed with difficulty in crystalline regions but take place more readily in amorphous regions. For example, the substitution of functional groups into cellulose has a disruptive effect on the structure thereof. If carried out to completion, the cellulose matrix would be destroyed and utimately water soluble polymers would be formed. Typical examples of this phenomenon are the hydroxyethyl cellulose and cellulose gums of the prior art, which become the commonly used adhesives and binders after dissolving in water.

Each anhydrous saccharide unit in a polysaccharide molecule may have three or more reactive hydroxy groups. Theoretically, all three or more can be substituted with the polymer. The product from such reaction, however, would have a degree of substitution of three or more, which in the case of ion exchange materials, would render it soluble. Even at levels of substitution below those at which total water solubility occurs, such polysaccharide derivatives become unsuitable as chromatographic supports. Therefore, substitution of the polysaccharide is restricted to the more reactive centers of the amorphous regions and is seldom carried out beyond the level of about 1 meq/gm of dry weight in fiber form. At this level of substitution, the native configuration of the polysaccharide structure is only slightly modified, and the low density non-uniform exchange sites are readily accessible to large biomolecules.

The final structure of a molecular support of the invention thus comprises a polysaccharide chain covalently modified at a multiplicity of sites along such chain with the synthetic polymers.

The polymer which modifies the polysaccharide is either a homopolymer or a copolymer. The definition of the polymer as a homo- or copolymer depends on whether the polymerizable compounds (a) and (b) are different. In its most general form, the copolymer could be a random, a block or an alternating copolymer.

In one embodiment, the polymerizable compound (a) (also called "comonomer (a)") may have a group capable of reacting with a hydroxy group of polysaccharide with the formation of a covalent bond. Such polymerizable compounds are defined for example in U.S. Pat. No. 4,070,348 to Kraemer et al., which is herein incorporated by reference. The chemical groups are capable of reacting with hydroxy groups at temperatures up to those at which the polysaccharide begins to decompose or depolymerize, e.g., 0° to 120° C., in aqueous solution and thereby form covalent bonds with the oxygen atoms of the hydroxy groups. Since water is always present in considerable excess with respect to the hydroxy groups, chemical groups which react spontaneously with water, such as, for example, isocyanate groups, are less suitable. Aqueous solutions comprise pure water or mixtures of water with one or more water miscible co-solvents, such as alcohols, ketones, and the like.

Hydroxy reactive groups of comonomer (a) are preferably activated carboxy groups such as are known from peptide chemistry or O-alkylating agents, such as alkyl halide or epoxide groups. Representatives of the O-alkylating comonomers are acrylic- and methacrylic anhydrides, acrylolylmethacryloyl N-hydroxy succinimides, omega-iodo-alkyl esters of acrylic or methacrylic acid in which the alkyl group in general contains 2 to 6 carbon atoms, allyl chloride, chloromethylstyrene, chloroacetoxy ethyl methacrylate, and compounds having a glycidyl group. The latter are ethers or esters formed between a glycidyl alcohol and an unsaturated alcohol or unsaturated carboxylic acid, respectively. The glycidyl alcohols are aliphatic and cycloaliphatic alcohols and ether alcohols having from 3 to 18 carbon atoms which are esterified with an alpha,beta-unsaturated carboxylic acid, preferably acrylic or methacrylic acid, or are etherified with an olefinically or acetylenically unsaturated alcohol. Typical compounds are glycidyl acrylate and methacrylate; 4,5-epoxy-pentylacrylate; 4-(2,3-epoxy-propyl)-N-butyl-methacrylate; 9,10-epoxy-stearylacrylate; 4-(2,3-epoxypropyl)-cyclohexyl methacrylate; ethylene glycol-monoglycidyl etheracrylate; and allyl glycidyl ether.

Preferred monomers for the homopolymers or copolymers of the synthetic polymer grafted to the polysaccharide are glycidyl acrylate and glycidly methacrylate, with a homopolymer of glycidyl methacrylate most preferred. Such homopolymers may be further modified by conversion to carboxylic groups (by reaction with, for example, acrylic acid) to amine-containing groups (by reaction with, for example, a diamine) and to hydroxy groups.

If the active comonomer units (a) are sensitive to hydroxy groups, and if they do not react with the polysaccharide offered, they may be transformed, in the presence of water, into hydrophilic carboxy or hydroxy groups. The activated groups are therefore present in the polymeric material in generally greater number than is necessary for the bonding with the polysaccharide.

In another embodiment, the polymerizable compound (a) may be one which does not react directly with hydroxy groups of the polysaccharide, but rather is covalently coupled to the polysaccharide indirectly, via a bridge compound. This is the case when the polysaccharide is first chemically activated as by oxidation, and reacted with a compound having, e.g., an epoxy group or a vinyl group, capable of reaction with an appropriate functionality of polymerizable comonomer (a).

The polymerizable comonomer (b) will vary depending on the ultimate use of the carrier material. If the carrier material's ultimate use is to serve as an ion exchange chromatographic material, the comonomer (b) may contain any of the well known ionizable chemical groups or precursors thereof such as compounds containing a vinyl or vinylidine group and a carboxylic acid, a carboxylate salt, a carboxylate ester, preferably having 1 to 6 carbon atoms, a carboxylic acid amide, a secondary or a tertiary amine, a quaternary ammonium, a sulfonic acid, a sulfonic acid ester, a sulfonamide, a phosphoric or phosphonic acid, or a phosphoramide or phosphonamide group.

When comonomer (b) carries the precursor of a material having ion exchange properties, the ion exchangable group itself can be obtained by unmasking, such as for example, by selective hydrolysis of an anhydride, ester or amide, or salt formation with an appropriate mono-, di- or trivalent alkaline or alkaline earth metal, as is otherwise well-known in the art.

Preferred ion exchange functionalities for comonomer (b) are aminoethyl, carboxymethyl, carboxyethyl, citrate, diethylaminoethyl, ecteola (mixed amines), guanido ethyl, phosphonic acid, p-aminobenzyl, polyethylene imine, sulphoethyl, sulphomethyl, triethylaminoethyl, or chelating groups such as —N(CH$_2$CO$_2$H)$_2$. When the ultimate use of the carrier material is as a support for an affinity liquid, comonomer (b) carries a chemical group capable of causing the covalent coupline of said comonomer (b) to an affinity ligand, i.e. an "anchoring" group. Since most affinity ligands carry nucleophiles such as hydroxy, amino, thiol, carboxylate, and the like, any electrophilic group capable of reacting with such nucleophile can be present in comonomer (b). Such electrophilic groups include, but are not limited to, those described previously as active groups capable of reacting with the hydroxy group of cellulose. They also include activated carboxy groups used in peptide chemistry for the formulation of peptide bonds, such as carbonyl chlorides, carboxylic anhydrides and carboxylic acid azide groups, as well as phenyl esters and aldehydes used for the formation of Schiff (imine) bases.

Also useful are the carboxylates of hydroxylamino derivatives of the formula (1)

$$R-CO-O-R'''-N\begin{matrix}R'\\R''\end{matrix} \quad (1)$$

in which R is an alpha,beta-unsaturated, polymerizable radical and R' and R" are identical or different C$_1$-C$_6$ alkyl or alkanoyl groups. R''' may be a direct bond (—) or a C$_2$-C$_3$ alkyl group. R' and R" together with the N atom may also form a heterocyclic ring. Typical compounds of this type are:

CH$_2$=C(H or CH$_3$)—CO—O—N—(C$_2$H$_5$)$_2$

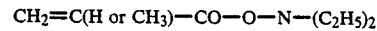

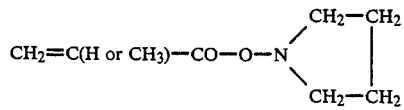

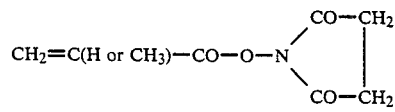

CH$_2$=CH(H or CH$_3$)—CO—O—C$_2$H$_4$—N(C$_2$H$_5$)$_2$

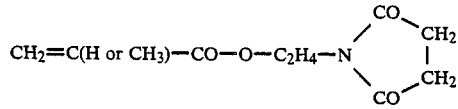

Other compounds having activated carboxyl groups include acryloyl- and methacryloyl chloride, acrylic and methacrylic anhydride, maleic anhydride, phenyl acrylate and methacrylate, glycidyl acrylate and methacrylate, and 4-iodobutylacrylate and methacrylate.

A very useful potentially electrophilic reactive group in comonomer (b) useful for coupling to an affinity ligand is a group capable of being activated to an electrophilic group with a reagent such as a cyanogen halide. It is known in the art the cyanogen halides react with 1,2-diols to yield activated structures of the following types:

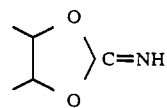

This structure is then capable of reacting with the nucleophile of an affinity ligand. Among the preferred 1,2-diols present in comonomer (b) are various saccharides, including monosaccharides such as glucose, mannose and galactose, disaccharides such as lactose and maltose, trisaccharides such as raffinose or, generally, glycosides. The 1,2-diol-containing functional group can be attached to the polymerizable comonomer (b) by such reactions as esterification, amide formation, and the like. Among the most preferred of these is the reaction of glycidyl acrylate or methacrylate with a saccharide, to yield an ether-containing comonomer (b).

When the ultimate use of the carrier material is as a carrier for biological molecules, any of the anchoring groups mentioned for comonomers (a) or (b) can also be used. Other types of activated groups such as those containing aldehydes or amines can also be used.

The polymerizable comonomer (b) can be substantially of one type or can be a mixture of one or more types. This is particularly applicable when the ultimate use of the material is as an ion exchange carrier. Comonomers (b) can then contain such functional groups as anionic exchange groups and cationic exchange groups in various different ratios, if desired.

Preferably, the polymerizable monounsaturated compounds (b) are polymerizable compounds of the formula (4):

wherein
R$^1$ is hydrogen or methyl;
A is CO, or SO$_2$;
X is OH, OM (where is a metal ion), OR$^2$ (where R$^2$ is a straight or branched chain C$_1$-C$_{18}$ alkyl group), OR$^3$OH (where R$^3$ is a straight or branched chain C$_2$-C$_6$, alkyl or aromatic group), NR$^4$R$^5$ or N$^+$R$^4$R$^5$R$^6$ (where R$^4$ is the same or different as R$^5$ which is the same or different as R$_6$, and are hydrogen, R$^2$ or R$^3$OH);
AX may also have formula (5):

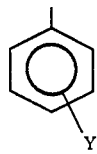

wherein Y is —CO$_2^-$, —CH$_2$CO$_2$O$^-$, —SO$_3^-$, —CH$_2$SO$_3^-$, —PO$_4$H$^-$, —CH$_2$PO$_4$H$^-$, —CH$_2$N(CH$_2$—COO$^-$)$_2$, —CH$_2$—NR$^4$R$^5$, or —CH$_2$—NR$^4$R$^5$R$^6$, or the corresponding free acid, ester or partial ester groups, as described previously. In these formulae, the groups $R^4$, $R^5$; $R^4$, $R^6$; or $R^5$, $R^6$ may form a 5-7 membered heterocyclic ring with the nitrogen atom. $R^4$, $R^5$, and $R^6$ are as previously defined.

Alternatively, (and when the material is to be used as an anchor for affinity ligands or biomolecules), A is CO or $SO_2$, and X is most preferably O—$CH_2$—CH(OH)—$CH_2$-Saccharide, where "-Saccharide" is a mono-, di- or polysaccharide having a group which can be activated for reaction with nucleophilic reactive groups on the affinity ligand or the biomolecule by a cyanogen halide.

The preferred comonomer (a) for anionic exchange materials is glycidyl acrylate or methacrylate. The preferred comonomer (b) for anionic exchange materials is diethylaminoethyl acrylate or methacrylate. The most preferred comonomer (b) for anchoring materials is the comonomer obtained from reaction of glycidyl acrylate or methacrylate with glucose.

The preferred comonomer (a) for cationic exchange materials is aminoethyl methacrylate, coupled to the polysaccharide by previous oxidation thereof. The preferred comonomer (b) for cationic exchange materials is methacrylic acid, acrylic acid and acrylic acid dimer, or glycidyl methacrylate further oxidized to a carboxylic acid group after copolymerization.

However, as stated above, where the primary function of the matrix is for removal of microrganism-originated contaminants, the preferred modifier for the polysaccharide is a homopolymer of glycidyl methacrylate, perhaps reacted to provide carboxy, amine or hydroxy reactive sites.

The average molecular weight of the polysaccharide-modifying polymer is dependent on the number of monomers present therein. It is required to have at least a sufficient number of comonomers (a) so as to be able to form covalent attachment throughout amorphous regions of the polysaccharide surface. The number of comonomers (b) cannot be too small, since otherwise the exchange capacity, or the anchoring/interacting capacity is negligible. The number of comonomers (b) can neither be too high, since this would cause great difficulty in the reaction between the reactive groups of comonomer (a) and the polysaccharide. Preferably, the polysaccharide-modifying copolymer carries anywhere between 1 and 500 units (a) plus (b), most preferably between 20 and 100 units. This corresponds to molecular weights of between about 100 and 100,000, preferably between 1,000 and 10,000.

Other neutral comonomers (c), different than those represented by (i), (ii), (iii) or (iv) supra, can also be added to the polymer, if desired. These comonomers may be polymerizable unsaturated compounds carrying neutral chemical groups such as hydroxy groups, amide groups, alkyl groups, aryl groups and the like. Preferred among comonomers (c) are $C_1$-$C_6$ alkyl acrylates or methacrylates, or the corresponding hydroxy alkyl acrylates or alkacrylates. The function of comonomers (c) may be to increase the presence of hydrophobic or hydrophilic residues in the polymers, so as to provide a desired balance of hydrophilic and hydrophobic groups, if necessary.

The minimum ratio of comonomer (a) to total comonomer content is important. The synthetic polymer should have a sufficient amount of comonomer (a) to permit substantial covalent coupling of the polymer to the polysaccharide. If too little comonomer (a) is present in the polymer, then grafting becomes difficult, if not impossible. Generally, a minimum of about 4-12, preferably 5-10% by weight of comonomer (a) relative to the total of (a) plus (b) (and (c) if any is present) is needed. Amounts of about 0.5 to 1 or 2% by weight appear to merely cross-link the polymer without substantial grafting onto the polysaccharide.

The upper limit of comonomer (a) in the polymer can be varied up to 99.9% by weight depending on the desired amount of rigidity, functionality and hydrophilicity. Increasing the amount of comonomer (a) too much above 15 to 20% by weight, however, decreases the porosity. Large molecules then have difficulty in graining full access to the functional groups in comonomer (b). Of course, where microorganism-originated contaminants are the primary concern, this is not a factor. In some instances, it may be preferred to have a predominance of comonomers (b) over comonomers (a). Comonomers (c) may be present in an amount of up to 20 percent by weight of the total (a) plus (b) plus (c).

The weight ratio of polysaccharide to the modifying polymer is freely adjustable, and varies from 0.1 to 5 weight parts of copolymer to parts by weight of the polysaccharide.

When comonomers (b) carry ionizable chemical groups capable of providing cation exchange capacity, it is found that unless some degree of crosslinking is provided, the flexibility of the material in solution tends to favor the formation of micelle-type aggregates and slow loss of capacity. Therefore, it is a preferred mode of the invention to provide polymeric crosslinking for these types of modified polysaccharides. Crosslinking can be provided either by incorporating into the polymerization recipe a small amount of polyunsaturated comonomer having at least two polymerizable alpha,-beta-carbon double bonds, such as for example mono- and polyethylene glycol dimethacrylates and diacrylates (with the polyethylene glycol residue containing up to 6 ethylene groups), ethylene dimethacrylate, ethylene diacrylate, tetramethylene dimethacrylate, tetraethylene diacrylate, divinylbenzene, triallyl cyanurate, methylene-bis-acrylamide or -bis-methacrylamide, and the like.

Another type of crosslinking agent is particularly applicable to copolymers made from an aminoalkyl comonomer (b). Because of the presence of a free pair of electrons on the aminoalkyl nitrogen atoms, crosslinking can be carried out with such bifunctional reagents as would react with nitrogen free electron pairs. Among these are the diacyl halides, such as Hal—CO—($CH_2$)$_n$—CO—Hal, or the alkyl dihalides, such as Hal—($CH_2$)$_n$—Hal, wherein Hal is a halide such as chloride, bromide or iodide, and n may be anywhere between 2 and 12. Other bifunctional reagents capable of reaction with nitrogen atoms can also be used. The advantage of these bifunctional reagents is that they simultaneously crosslink the copolymer, while also providing a cationic charge at the nitrogen centers, thereby ionizing the material.

The amount of crosslinking agent is best determined empirically. It is to be considered sufficient when the polymer preserves the ion exchange capacity at a constant value over time, yet would be too high if swelling is prevented, and too much rigidity is obtained in the final materials. Ideally, an amount of crosslinking agent between 5 to 20 mole percent of the synthetic polymer units is sufficient.

By the term "affinity ligand" as used throughout the present application and in the claims, is meant to include any small or high molecular weight molecule which can be immobilized in a stationary phase and used to purify a complementary binding molecule from a solute phase by affinity chromatography. For example, a ligand can be an inhibitor, a cofactor, a prosthetic group, or a polymeric substrate, all of these useful to purify enzymes or holoenzymes. Other ligand/ligate pairs are enzymes/polymeric inhibitors; nucleic acid, single strand/nucleic acid, complementary strand; hapten or antigen/antibody; antibody/proteins or polysaccharides; monosaccharides or polysaccharides/lectins or receptors; lectins/glycoproteins or receptors; small target compounds/binding proteins; and binding protein/small target compounds. When antigen/antibody pairs are used as the ligand/ligate pair, the technique takes the particular name "immunoaffinity" chromatography.

The "biologically active molecule" which can be bound to the carriers of the invention can include enzymes, enzyme substrates, inhibitors, hormones, antibiotics, antibodies, antigens, peptides, saccharides, nucleic acids, and the like. The only requirement for these molecules is that they have reactive groups thereon which can be covalently coupled to the anchoring chemical groups on comonomer (b).

Of particular interest is the immobilization of enzymes such as hydrolases, isomerases, proteases, amylases, and the like. These immobilized enzymes can then be used in biochemical reactors, as is otherwise well-known in the art.

By the use of the term "reverse phase chromatography" or "hydrophobic interaction chromatography" is meant to include chromatography used to adsorb hydrophobic components in mixtures. Such components include lipids, cell fragments and the like. In this embodiment, comonomer (b)(iv) is usually an acrylate or methacrylate ester of $C_6$-$C_{18}$ straight or branched chain alcohols, or of aromatic alcohols such as phenol or naphthol.

However, in a preferred configuration wherein the modified polysaccharide is to be utilized as a separation matrix, in combination with a polyionene, for the bacterial decontamination of pharmaceutical and/or biological solutions, the polysaccharide is cellulose and the modifier thereof is a homopolymer of glycidyl methacrylate as in Example 3 below.

The term "polyionene" or "ionene-type polymeric composition," first coined by Rembaum, A. et al., *Polymer Letters*, 6: 159–171 (1968), has been adopted by other authors in the field, including *Chemical Abstracts*, as reported in U.S. Pat. No. 3,784,649. However, for the present invention, "polyionene" is meant to include those water-soluble polymers having polyquaternary ammonium groups separated by hydrophobic groups, said hydrophobic groups comprising aromatic groups or alkyl groups containing at least six carbon atoms.

The polyionenes of the present invention include those polymers having the following repeating units:

$$R_2^7\overset{+}{N}-L-R_2^8\overset{+}{N}-M$$

wherein $R^7$ and $R^8$ are $C_1$-$C_4$ alkyl; L is $-(CH_2)_n-P-(CH_2)_m$; M is $-(CH_2)_o-Q-(CH_2)_p-$, with P and Q being the same or different and representing at least one of $CH_2$, CHA, $C_6H_4$, pyridine, $C_6H_3A$, $C_6H_4-CHA-C_6H_4$, or $R^9C_6H_2A$; wherein A is a reactive group, typically OH, amino, aldehyde, halide, epoxy and carboxy, wherein $R^9$ is $C_1$-$C_4$ alkyl; and wherein m, n, o and p represent integers from 1 to 20.

In general, polyionene polymers are prepared by reacting a dihalo organic compound with a secondary or tertiary amine. Typical polymerization processes and reactants are described in U.S. Pat. No. 2,261,002 to Ritter; U.S. Pat. No. 2,271,378 to Searle; U.S. Pat. No. 3,489,663 to Bayer et al., U.S. Pat. No. 3,784,649 to Buckman et al.; and U.S. Pat. No. 4,038,318 to Tai. Additionally, Rembaum, at U.S. Pat. Nos. 3,898,188; 3,910,819; 3,927,242; and 4,013,507 describes additional polyionenes and their synthetic procedures. Each of the above-referenced U.S. patents is specifically incorporated in its entirety herein.

Typical dihalo organic compounds included within the scope of the present polyionene precursors include those compounds having the following general formula:

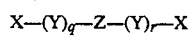

where X is I, Br, or Cl; Y represents a $CH_2$ group and/or a substituted $CH_2$ group wherein one of the hydrogens is replaced with a $C_1$-$C_4$ alkyl or hydroxy-substituted $C_1$-$C_4$ alkyl; and q and r independently represent integers varying from 1 to 10. Z represents $CH_2$, CHA, $C_6H_4$, $C_6H_3A$, $C_6H_4-CHA-C_6H_4$ and $R^9C_6H_2A$ where $R^9$ represents a $C_1$-$C_4$ alkyl, with A defined as above.

In a preferred embodiment, wherein the modified polysaccharide substrate is treated with the polyionene, Z represents a moiety such as CHA, $C_6H_3A$ or $R^9C_6H_2A$, the presence of the A group providing a linking site for subsequent reaction with the modified polysaccharide substrate.

Suitable secondary and ditertiary amines include, but are not limited to N,N,N',N'-tetramethylethylenediamine, N,N,N',N'-tetraethylethylenediamine, N,N,N',N'-tetramethyl-1,3-butanediamine, N,N,N',N'-tetraethyl-1,3-butanediamine, N,N,N',N'-tetramethyl-1,4-butanediamine, N,N,N',N'-tetraethyl-1,4-butanediamine, N,N'-dimethylpiperazine, N,N'-diethylpiperazine, 1,4-diazabicyclo(2,2,2)octane, 4,4'-dipyridyl, N,N,N',N'-tetramethylbenzidine, N,N,N',N'-tetraethylbenzidine, oxy-bis-2,2(N,N-dimethylethylamine), 4,4'-bis(dimethylamino)benzophenone, p,p'-methylene-bis(N,N'-dimethylaniline), N,N,N',N'-tetrakis(hydroxyethyl)ethylenediamine, N,N,N',N'-tetrakis(2-hydroxypropyl)ethylenediamine, N,N,N',N'-tetramethyl-2-butenediamine, N,N,N',N'-tetramethyl-1,6-hexanediamine, bis(dimethylaminomethyl)benzenes, bis(dimethylaminomethyl)toluenes, bis(dimethylaminomethyl)xylenes, dimethylamine, diethylamine, diisopropylamine, dibutylamine, diethanolamine, diisopropanolamine, piperidine, morpholine, 2,6-dimethyl-morpholine, 1,2,4-trimethylpiperazine, and 1,4-bis(2-hydroxypropyl)-2-methylpiperazine.

Among the preferred reactants are the N,N,N',N'-tetra-($C_1$-$C_4$ alkyl) alkyl diamines having 1 to 10 carbon atoms between the substituted amine groups. More preferred is N,N,N',N'-tetramethyl-1,6-hexanediamine and N,N,N',N'-tetraethyl-1,6-hexanediamine.

Included as well, however, are compounds having the general formula:

$$N(CH_3)_2-CH_2-M-CH_2-N(CH_3)_2$$

where M is a reactive moiety-containing group such as hydroxy, amino, aldehyde, carboxy, halide and epoxy. Typically, M maybe CHOH, $C_6H_3OH$, $C_6H_4CHOHC_6H_4$ and $R^9C_6H_2OH$, with $R^9$ as described above.

Typical reactions for the synthesis of the polyionenes for the practice of the present invention wherein the polyionenes are coated or grafted onto the modified polysaccharide substrate are as follows:

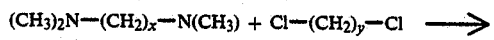

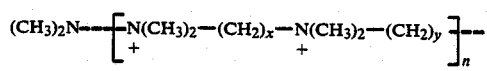

(where x and y are whole number integers of 6-20)

where n is a whole number integer. Typically, the polyionenes of this invention have molecular weights in the range of 10,000 to 100,000.

Where, for example, x is 6 and y is 6, the resulting product is a 6,6-polyionene having the general formula:

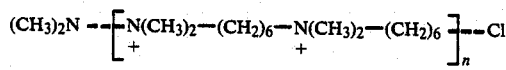

where x is 6 and y is 10, the resulting product is a 6,10-polyionene having the general formula:

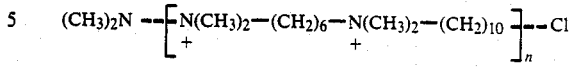

Also contemplated are the reaction products wherein a mixture of dihalo compounds are used, for example, where $Cl-(CH_2)_6-Cl$ and $Cl-(CH_2)_{10}-Cl$ are reacted with a secondary or ditertiary diamine, yielding a product having the general formula:

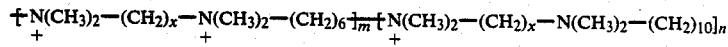

where m and n are whole number integers.

The last above concept is especially useful where it is desirable to synthesize polyionenes which contain reactive groups, i.e. hydroxyl groups. A typical reaction is as follows:

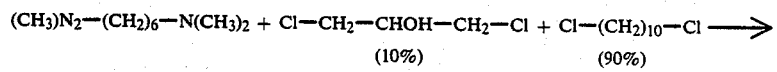

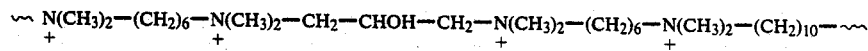

Similarly, reactive group-containing polyionenes may be obtained from the following reaction:

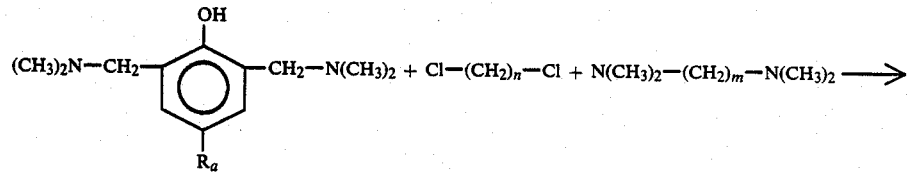

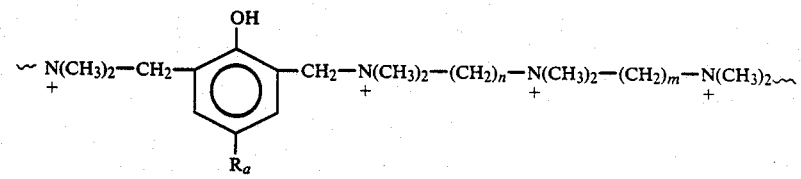

where $R_a$ is, for example, a $C_1$-$C_4$ alkyl.

By reacting the pendant reactive group with, for example, epichlorohydrin, the polyionene may be restructured to contain epoxy groups, said epoxy groups themselves useful for bonding onto the modified polysaccharide substrate.

Another manner for creating reactive sites on the polyionene for subsequent bonding is as follows:

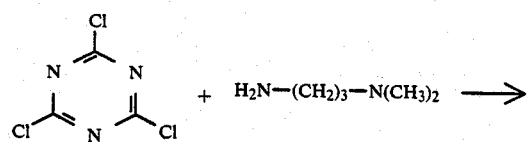

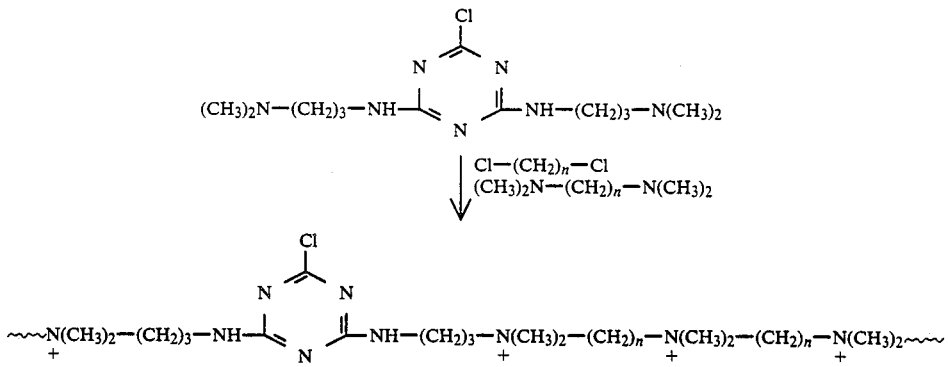

The resulting polyionene, containing a substituted halide (chloride) in the heterocyclic ring, may then be reacted with a suitable hydrophobic spacer arm, for example NH$_2$—(CH$_2$)$_3$—NH—(CH$_2$)$_3$—NH$_2$, to yield a reaction product with an amine terminated linker arm:

said amine terminated linker arm may subsequently be reacted with, for example, epoxy functional groups on the modified polysaccharide to thereby graft the polyionene to the modified substrate.

An alternative procedure for creating reactive groups, i.e. hydroxy groups, on the polyionene is as follows:

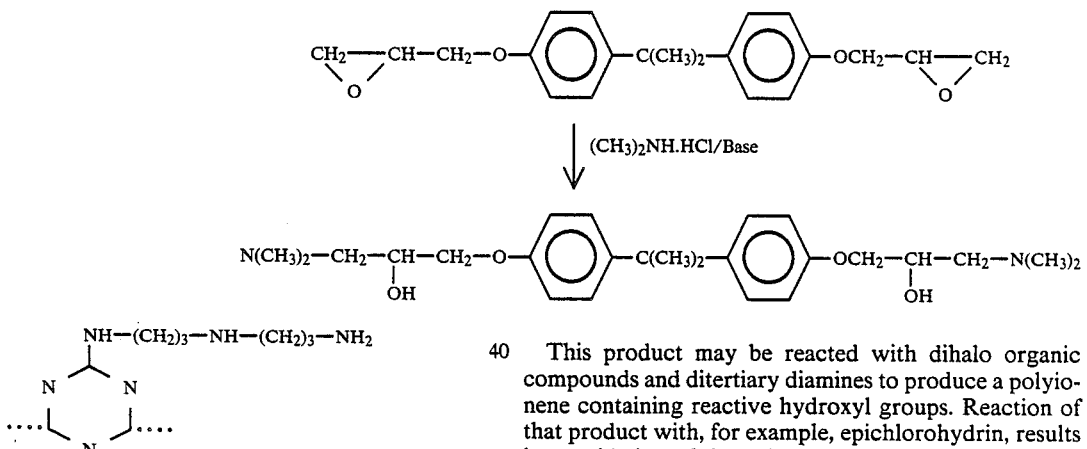

This product may be reacted with dihalo organic compounds and ditertiary diamines to produce a polyionene containing reactive hydroxyl groups. Reaction of that product with, for example, epichlorohydrin, results in epoxidation of the polyionene as above.

Another method for producing reactive group-containing polyionenes is as follows:

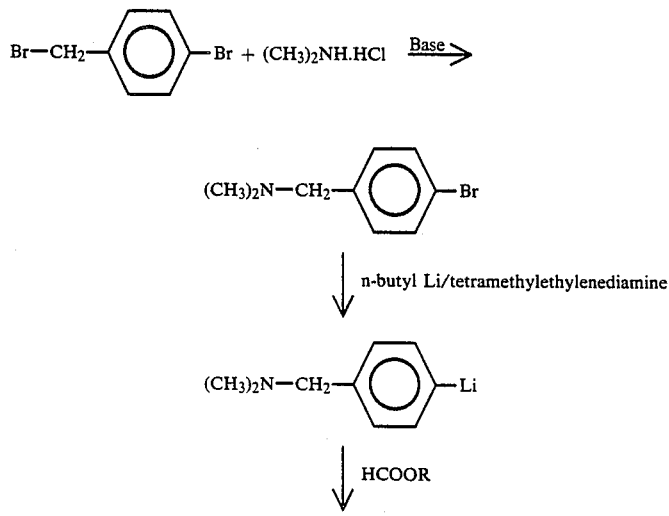

-continued

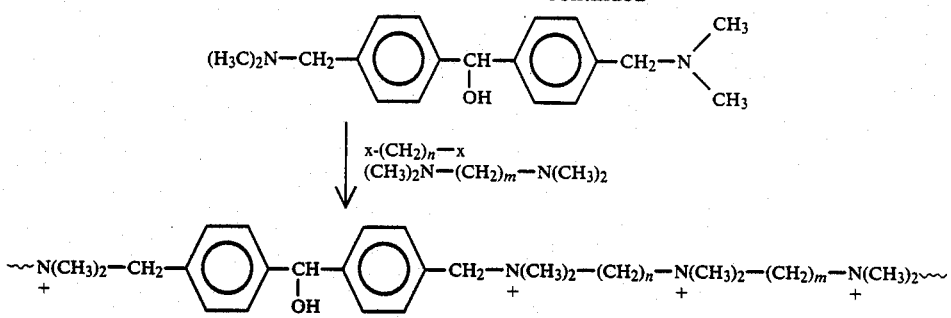

Further, a mixture of ditertiary diamines and a reactive group-containing ditertiary diamine, for example, 1,3-bis-(dimethylamino)-2-propanol may be reacted with a dihalo compound as follows:

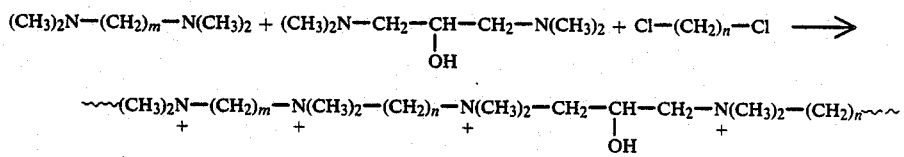

As above, the hydroxyl group may then be reacted with, for example, epichlorohydrin to produce an epoxidized derivative for bonding purposes.

By the term "polyionene-transformed modified polysaccharide" is meant to include any and all of the above-described modified polysaccharides which have been transformed by the presence of a polyionene bonded to the surface of said modified polysaccharide. In one embodiment, the polyionene is reactive coupling to the modified polysaccharide through the hydroxy coupling groups thereon. The coupling process substantially improves the resistance of the polyionene-transformed modified polysaccharide to leaching during use thereof.

By the term "bonding" or "bonded" is intended that the polyionene is sufficiently attached to the modified polysaccharide that said polyionene will not significantly be extracted under the intended conditions of use.

By the term "microorganism-originated contaminants" or "contaminants of microorganism origin" is meant to include bacteria, bacterial products such as endotoxins, viruses, micoplasma and the like.

By the term "biological liquids" is meant to include each and every liquid system which is derived from or amenable to use with living organisms. Such liquids are ordinarily handled and processed under sanitary or sterile conditions and therefore require sanitized or sterilized media for separation. Included within such terms are isotonic solutions for intramuscular or intravenous administration, solutions designated for oral adminstration, solutions for topical use, biological wastes or other biological fluids which may comprise filterable bodies such as impurities, e.g. bacteria, viruses, or endotoxins which are desirably isolated or separated for examination or disposable by immobilization or fixation upon or entrapment within separation media.

Separation media in accordance with this invention may be employed alone or combination with other separation media to treat pharmaceuticals such as antibiotics, saline solutions, dextrose solutions, vaccines, blood plasma, serums, sterile water or eye washes; beverages such as cordials, gin, vodka, beer, scotch, whiskey, sweet and dry wine, champagne or brandy; cosmetics such as mouthwash, perfume, shampoo, hair tonic, face cream, or shaving lotion; food products such as vinegar, vegetable oils; chemicals such as antiseptics, insecticides, photographic solutions, electroplating solutions, cleaning compounds, solvent purification and lubrication oil; and the like, where retention of submicronic particles, removal of contaminants of microorganism origin, and resolution of colloidal hazes is desired. The separation media may be used to isolate blood parasites from peripheral blood and also to remove microorganism-originated contaminants from peripheral blood. Included among the contemplated utilities are the use of the separation media for separating contaminants from blood to be used for re-infusion. Ren, H. E. et al., *Arch. Biochem. Biophys.*, 209: 579 (1981).

The carrier materials of the present invention can be used per se in the same manner as other polysaccharide-based carrier materials of the prior art. Alternatively, and in a preferred mode, the polysaccharide material, which is preferably in fibrous form after the modification and polyionene transformation, can be formed into a self-supporting fibrous matrix, such as a fibrous sheet, with ion exchange properties, affinity chromatography properties, bioreactive or reverse phase properties, while at the same time demonstrating the capacity to remove microorganism-originated contaminants. The modified fibrous polysaccharide fibrous media can also incorporate unmodified fibers of various different sizes, and, in addition, can also incorporate modified or unmodified particulate material. However, due to the biocidal and entrapping characteristics of the polyionene-transformed modified polysaccharides, these separation media are especially well suited for decontamination of biological and pharmaceutical solutions.

The fibrous media comprises a porous matrix of fiber wherein, because of the nature of the present invention, the fiber is effective for molecular or ionic separations or molecular reactions. The matrix is substantially homogeneous with respect to each component. When a particulate is present, it is preferred to modify it so that it is also effective for molecular or ionic separations or reactions. Such a particulate should be contained in the fibrous phase in an effective amount to achieve the desired separations or reactions. The overall media is substantially inert and dimensionally stable.

The preferred particulates which can be used include all of those substances which can be provided in finely divided form and exhibit chromatographic functionality, i.e., capable of effective molecular separations and/or reactions. Mixtures of such compositions may also be utilized. Exemplary of such particulates are silica, alumina, zirconium oxide, diatomaceous earth, perlite, clays such as vermiculite, carbon such as activated carbon, modified polymer particulates such as other ion exchange resins, crystalline cellulose, molecular sieves, and the like, the surfaces of which may be modified in a conventional manner. Such materials are commercially available under a variety of trademarks such as Biosila, Hi-Flosil, Li Chroprep Si, Micropak Si, Nucleosil, Partisil, Porasil, Spherosil, Zorbax cil, Corasil, Pallosil, Zipax, Bondapak, LiChrosorb, Hypersil, Zorbax, Perisorb, Factosil, Corning Porous Glass, Dowex, Amberlite resins, and the like.

Examples of references which describe particulates effective for molecular separations are Miller, U.S. Pat. No. 3,669,841, Kirkland et al., U.S. Pat. No. 3,722,181, Kirkland et al., U.S. Pat. No. 3,795,313, Regnier, U.S. Pat. No. 3,983,299, Chang, U.S. Pat. No. 4,029,583, Stehl, U.S. Pat. No. 3,664,967, Krekeler, U.S. Pat. No. 4,053,565 and Iher, U.S. Pat. No. 4,105,426. The entire disclosures of all of these references are incorporated by reference herein.

The particle size of the particulate is not critical but influences somewhat the flow rate at which the sample to be treated passes through the material. Usually, uniform particle sizes greater than about 5 microns are preferred, with about 10-100 microns constituting a practical operational range. The amount of the particulate can vary widely from about 10 wt.% up to 80 wt.% or more of the solid phase. The optimum particulate concentration will vary depending on the molecular separation desired.

The fibrous media should be capable of immobilizing the particulate contained therein, i.e., capable of preventing significant particulate loss from the stationary phase, yet having a porosity which enables the fluid to pass through the media. Thus, although the modified cellulose materials of the present invention are self-bonding and the addition of extra fibers or binders may not be necessary, it is possible to utilize such extra fibers or binders. Other fibers usable for the media include polyacrylonitrile fibers, nylon fibers, wool fibers, rayon fibers and polyvinyl chloride fibers, other cellulose fibers such as wood pulp and cotton, and cellulose acetate.

One embodiment of the invention is the provision of a fibrous media comprising two different types of celluloses: one a modified cellulose according to the invention and another an unmodified cellulose.

Another embodiment of the invention, which may also be coupled with the aforementiond celluloses is an unrefined structural fiber which assists in providing sheets of sufficient structural integrity in both the wet "as formed" condition, and in the final dry condition, and also allows handling during processing as well as suitability for the intended end use. Such fibers are typically relatively lrge, with commercially available diameters in the range of 6 to 60 micrometers. Wood pulp can also be used and has fiber diameters ranging from 15 to 25 micrometers, and fiber lengths of about 0.85 to about 6.5 mm. The unrefined self-bonding structural fibers typically have a Canadian Standard Freeness of +400 to +800 ml. These long self-bonding fibers may constitute greater than 50% of the fibrous media, by weight, preferably 60-100% of the fibrous media, and most preferably 100%. Optionally, a minor portion of cellulose pulp which has been refined to a Canadian Standard Freeness of between +100 and −600 ml may be incorporated with a major portion of the normally dimensioned cellulose pulp (+400 to +800 ml). In particular, from about 1 to about 20% of the refined pulp and about 50% to about 90% of the unrefined cellulose may be contained in the matrix. Particulate may also be added.

When the particulate materials are millimicron-sized, it may be desirable to use, in addition, a mixture of cationic and anionic resins as described by assignee's U.S. Pat. No. 4,511,473, incorporated by reference herein. Alternatively, one may use a medium containing, in addition to the millimicron-sized particles, a neutral organic polymeric resin having oxygen atoms along the polymeric backbone thereof, as described in the assignee's co-pending U.S. patent application Ser. No. 401,361, filed on July 23, 1982, incorporated by reference herein.

Also of particular interest in the present invention is the use of modified cellulosic fibrous media carrying modified inorganic support materials, such as for example are described in Regnier, U.S. Pat. No. 3,983,299, Kirkland et al., U.S. Pat. No. 3,795,313, Kirkland et al., U.S. Pat. No. 3,722,181, Mazarguil et al., U.S. Pat. No. 4,034,139, Talley et al., U.S. Pat. No. 4,118,316, Ho Chang et al., U.S. Pat. No. 4,029,583 or Regnier, U.S. Pat. No. 4,108,603. These are all incorporated herein by reference. In particular, it is possible to derivatize siliceous particles with silanes and attach thereto various ion exchange or anchoring groups. In this embodiment then, both the cellulosic fiber and the siliceous particulate are modified, and their interaction provides increased anchoring and/or ion exchange capacity. The addition of particulate material tends to increase the rigidity and strength of the fibrous media and renders it readily useful for industrial applications, especially those involving high pressure.

PROCESS OF PREPARATION

The polymer-modified polysaccharide material of the invention can be prepared in various modes. Generally speaking, in one mode, one can first prepare the polymer and then condense the same through its hydroxy reacting groups (if available) to the polysaccharide. Alternatively, in another mode, one can first react the polysaccharide with a hydroxy group-reactive comonomer (a) followed by copolymerization with comonomer (b) and any other comonomers (e.g., crosslinking comonomers, hydrophobic comonomers, etc.), as desired. These reactions are therefore of two types: (1) coupling of saccharides to hydroxy reactive groups on comonomer (a), and (2) polymerization of polymerizable unsaturated compounds. The order in which these are carried out is not particularly critical.

Still a third method of (indirectly) attaching the synthetic polymer to the polysaccharide involves previous chemical activation of the polysaccharide. For example, polysaccharide can be treated with oxidizing agents such as periodate, hydrogen peroxide, ceric or other metallic oxidizing ions or the like. Reaction of the activate polysaccharide with an amino-containing polymerizable monomeric compound followed by reduction, will normally yield derivatized polysaccharide-carrying unsaturated functionalities along the chain thereof. These unsaturated functionalities can then serve as further attachment positions for conjugating the polymer thereto.

Another type of chemical activation of the polysaccharide involves reaction with a compound such as a diepoxide or epichlorohydrin, which yields a derivatized polysaccharide-carrying epoxy or other groups along the chain thereof. These epoxy or other groups then serve as conjugating positions on the polysaccharide chains.

The chemical activation modes of (indirect) attachment of the polymer to polysaccharide are particularly useful when introducing negative (anionic) functionalities into the polymer. This is due to the fact that graft polymerization, which is a common way of conferring positive charge to polysaccharides such as cellulose, is not very effective when attempting to confer negative charges (present in carboxy, phosphoric, sulphonic groups, etc.) thereto.

Polymerization of comonomers can be carried out by radical chain, step-reaction, ionic and coordination polymerization. Particularly useful is radical polymerization.

The free radical addition polymerization of radical polymerizable comonomers is carried out with free radical initiators using the well known steps of initiation, addition and termination. A usual procedure is to utilize a substance or substances which produce radicals capable of reacting with the monomers. Probably the simplest of all polymerization initiators are the organic peroxides and azo compounds. These substances decompose spontaneously into free radicals in common organic solvents at a finite rate, at temperatures between 50° and 140° C. For example, benzoyl peroxide decomposes into two benzoyloxy radicals at 60° C. Another example is afforded by the azo compound azo-bis-isobutyronitrile which similarly decomposes into radicals at easily accessible temperatures.

The necessary energy may also be provided by irradiating the initiator system with ultraviolet light. For example, initiation can be provided by irradiating the initiator system in the presence of photo initiators such as benzophenone and its derivatives, benzoin alkyl ethers or derivatives, or acetophenone, with ultraviolet light. It is then necessary that the initiator molecules absorb in the spectral region supplied. In this way, radicals can be generated at a finite rate at considerably lower temperatures than are necessary if purely thermal excitation is used. Finally, bimolecular reactions may produce radicals capable of initiating polymerization. Particularly important are the redox reactions, which occur in aqueous media, and involve electron transfer processes. For example, the systems Fe(II) plus hydrogen peroxide, or Ag(I), plus $S_2O_3^{--}$ are particularly important in initiating the radical polymerization of monomers. Because of the low temperature of initiation, the redox initiators or photochemically induced initiators are particularly preferred in the present invention. The amount of initiator is that sufficient to initiate the polymerization reaction. Polymerization is carried out until substantially all of the monomers or comonomers have been incorporated into the polymeric chains. This can be readily ascertained by simple analytical tests on the reaction mixture. Preferably, this polymerization is accomplished almost simultaneously with or immediately prior to the covalent coupling of the polymer to the polysaccharides. Preferably, the coupling and polymerization are performed in the same aqueous phase.

In one embodiment, the condensation of the comonomer (a) with the hydroxy group or groups of polysaccharide, whether carried out before polymerization or thereafter, is normally carried out by adjusting the temperature of the reaction mixture, or by adding an appropriate acid/base catalyst.

The most preferred method of carrying out the process is in a "one-pot" system, using a hydroxy reactive comonomer (a). All desired comonomers and polysaccharide are added to an inert solvent system, such as, e.g., water, alcohols, organics, and the like. The polysaccharide and comonomers are treated under conditions which will initiate polymerization of the comonomers. This can be accomplished, for example, by adding to a well stirred mixture a water solution of an initiator such as ammonium persulfate and sodium thiosulfate, and initiating polymerization from about 15° C. to 40° C. Alternatively, a photolibile initiator can be added and initiation caused by photochemical means. After stirring for a time sufficient to allow the polymerization to proceed to completion, the linking of the formed copolymer to the hydroxy groups of polysaccharide is caused by increasing the temperature of the reaction mixture to a temperature sufficient to cause this condensation. In the case when the linking group on the copolymer is a glycidyl group, such temperature is normally around 80°-100° C. Reaction is then allowed to proceed at the second temperature for a time sufficient to either go to completion, or to achieve modification of the polysaccharide to the desired capacity. The product is filtered, washed and dried for further treatment, if necessary. Unreacted monomer is preferably washed away with alcohol, unreacted catalyst with aqueous media and polymer with methanol or ethanol.

Further reaction of the modified polysaccharide may be by crosslinking, activation of the ion exchange potential, as for example by quaternization of nitrogen functions, saponification of esters, ionization of acids, sulfonation, phosphorylation or oxidation of epoxides, or other similar procedures. Quaternization, saponification, oxidation and salt formation are reactions well known to those skilled in the art, and will not be described in greater detail. Needless to say, the reactions useful for potentiation of the ion exchange potential of the material should not destroy the polysaccharide-copolymer linkages. Generally, strong acid conditions should be avoided.

Quaternization of aminoalkyl functions can be carried out simultaneously with crosslinking by reacting the modified polysaccharide with diacyl halides or alkyl dihalides, at a ratio of 0.1 to 30 parts by weight of the halides per 100 parts of polysaccharide at appropriate temperature, time and solvent conditions.

Another further reaction of the modified polysaccharide materials would be to anchor the affinity ligands or biologically active molecules to the anchoring groups of comonomer (b). This reaction can be readily accomplished by mixing in an appropriate solvent, normally aqueous, the affinity ligand or biomolecule to be anchored and the modified polysaccharide, and carrying out anchoring for a time and under conditions sufficient to cause covalent coupling therebetween. It may be necessary to activate polysaccharide groups on comonomer (b) with such materials as cyanogen halides, and to then further treat the activated polysaccharides with the affinity ligands or biomolecules. In this embodiment, it is preferred to first couple the affinity ligand or biologically active molecule to comonomer units (b), and then bind the resulting polymer or copolymer to the polysaccharide.

The reactions between the affinity ligand or biologically active molecule and the anchoring groups on comonomer (b) are normally carried out at temperatures of from 0° C. to 50° C., and may involve the addition of catalysts such as acid or base, or metals, or such other materials as DCC. The resulting ligand- or biomolecule-containing modified polysaccharide is washed under appropriate conditions and is ready for further treatment, if necessary.

Hydrophobic comonomers (b)(iv) are normally added to a copolymerization mixture in the presence of alcoholic solvents and/or surfactants. Washing is then carried out with alcohols.

As an illustrative example of the formation of a product under this invention can be described a composite of (1) cellulose, (2) a copolymer of (a) glucidyl methacrylate (GMA) and (b) diethylaminoethyl methacrylate (DEAEMA) and (3) a polyionene which has the following repeating units:

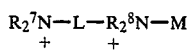

wherein $R^7$, $R^8$, L, and M are as described above.

This will be used only to show the many variables which are involved in the preparation, and which can be controlled to achieve a virtually unlimited number of products and resulting properties.

Step 1. Fiber dispersion and addition of monomers

Cotton linter is dispersed in water at 1% solids content—DEAEMA and GMA are added.

| | Variables |
|---|---|
| (A) | Chemical nature and physical size of cotton; |
| (B) | Purity of monomer; |
| (C) | Percent solid content; |
| (D) | Monomer/cotton ratio; |
| (E) | DEAEMA/GMA ratio. |

Step 2. Polymer Formation

Temperature of slurry is raised to 15° C. to 40° C., followed by addition of catalyst and reaction for 1-2 minutes.

| | Variables |
|---|---|
| (A) | Temperature and reaction time; |
| (B) | Amount of catalyst |

Step 3. Coupling of Polymers to Cotton

Temperature of slurry is raised to 80° C. to 100° C. within 25 minutes. Surfactant is added.

| | Variables |
|---|---|
| (A) | Rate of temperature rise; |
| (B) | pH of slurry; |
| (C) | Surfactant effect. |

Step 4. Wash (1)

Four volumes of water are used to wash the product in order to remove the inorganic catalyst left in the system.

| | Variables |
|---|---|
| (A) | Volume of water required to bring out the salt; |
| (B) | Mode of washing |

Step 5. Wash (2)

Two volumes of methanol are used to wash the product in order to remove the homopolymer and unreacted monomer.

| | Variable |
|---|---|
| (A) | Amounts of methanol, depending on reaction conditions |

Step 6. Wash (3)

Four volumes of water are used to wash the product in order to remove the methanol entrapped in the fibers.

| | Variable |
|---|---|
| (A) | Amount of water |

Step 7. Acidification

The product from Step 6 is redispersed in water and 1M HCl is added gradually to pH 4.0-4.5.

| | Variable |
|---|---|
| (A) | Amount of water |

Step 8-14: Quaternization

Step 8. Redispersal

The product from Step 6 is redispersed in water to a 1% solids content.

| | Variable |
|---|---|
| (A) | Solids content |

Step 9. Quaternization 1,6 dichlorohexane is added to the slurry in the presence of KI as catalyst. The temperature is raised to 95° C. and refluxed for 15 hours.

| | Variables |
|---|---|
| (A) | Quaternization agent; |
| (B) | Solvent; |
| (C) | Reaction time and temperature |

Step 10. Wash (5)

Water is used to remove the KI salt and the quaternization agent.

Step 11. Wash (6)

Methanol is used to remove excess quaternizing agent by increasing its solubility.

| Variable | |
|---|---|
| (A) | Degree of washing |

Step 12. Wash (7)

A water wash is used to removal methanol from the system.

Step 13. Acidification

1M HCl is used to protonate remaining unquaternized DEAE.

| Variable | |
|---|---|
| (A) | Balanced DEAE and QAE depends on the degree of quaternization carried out in the system |

Step 14. Wash (8)

Excess acid is washed away.

The preferred formation of self-supporting fibrous media from the modified polysaccharide materials of the invention can be carried out immediately after polymerization and polysaccharide modification. In this mode, unmasking the ion exchange groups or anchoring of affinity ligands or biomolecules may be carried out on the formed sheets themselves. Alternatively, the fibrous media is formed after unmasking of the ion exchange groups and/or anchoring of affinity ligands or biomolecules. The preferred method is to form the fibrous sheets after polysaccharide modification, and carry out further reactions, such as unmasking and anchoring on the sheets.

The production of an effective polyionene-transformed modified substrate requires a binding method such that the chemical groups essential for anti-bacterial action are not blocked or stearically hindered, while at the same time maximizing the presence of said groups. In the present invention, a preferred approach involves a two-step procedure wherein reactive groups are introduced into the polyionene molecule and the polyionene containing reactive groups then bound to the substrate, perhaps through a linker or spacer group. In this manner, the biocidal polyionene retains its active form after binding to the substrate, with the tertiary structure essentially unaltered, thereby maximizing the hydrophobic and charge interaction forces for entrapment and deactivation of the bio-organisms.

Transformation of the modified polysaccharide may proceed in a variety of ways. Where the polyionene polymer has been synthesized to produce a polymer absent reactive groups along the polymer backbone, for example a 6,10 polyionene, addition of a diamine, typically ethylene diamine, will serve to link the pendant chloride groups of the polyionene to the modified polysaccharide where the modified polysaccharide is one containing functional groups. A typical and preferred modified polysaccharide is the cellulose-GMA of Example 3, but the hydroxy, carboxy, and amine modified substrates are also useful.

Alternatively, where the polyionene itself has been synthesized to contain reactive groups along the polymer backbone as well as pendant reactive chloride groups, addition of a diamine such as ethylene diamine produces superior binding to the modified substrate as a result of the greater number of reactive sites per polymer chain.

Typically, the reaction mixture of modified polysaccharide, polyionene (2–30% based on the weight of the modified polysaccharide) and diamine (0.1–10% based on the weight of the modified polysaccharide) are reacted in aqueous solution at 25°–75° C. for a sufficient period of time to permit bonding of the polyionene to the modified substrate. Titration of the diamine to constancy is one means of following the course of the reaction. As is understood by those skilled in the art, the course of the bonding reaction will vary with conditions such as temperature, reactants, concentration, and the like.

A self-supporting fibrous matrix using the polyionene-transformed modified polysaccharide of the invention can preferably be made by vacuum filtering an aqueous slurry of fibers and, if desired, additional resins and modified or unmodified particulate. This forms a sheet having uniformly high porosity, fine pore-size structure with excellent flow characteristics and is substantially homogeneous with respect to fiber, resins and particulate.

The vacuum filtration is performed on a foraminous surface, normally a woven wire mesh which, in practice, may vary from 50 mesh to 200 mesh, with mesh openings ranging from 280 micrometers to 70 micrometers, respectively. Finer meshes are unsuitable because of clogging problems and/or structural inadequacy.

The sequence of adding the overall components to the slurry (modified fibers, other fibers, particulates, modified particulates, other resins, etc.) is relatively unimportant, provided that the slurry is subjected to controlled hydrodynamic shear forces during the mixing process. The slurry is normally prepared at, say, about 4% consistency and then diluted with additional water with a proper consistency required for vacuum filtering and sheet formation. This latter consistency will vary depending upon the type of equipment used to form the sheet. Typically, the slurry is cast onto a foraminous surface, vacuum filtered and dried in the conventional manner.

The flat, dimensionally stable sheet can be of any desired thickness and is then cut to the appropriate dimensions for each type of application. Preferably, the wet sheet is dried and then cut to proper size in order to form discs. These discs can be loaded onto an appropriately sized cylinder column to form the desired medium. The disc and cylinder should preferably be in interference fit so that the disc can be pushed into the cylinder without distortion, but not fall under gravitational force allowing gaps between the discs and the cylinder. After the column is packed dry, a pump can be used to pump solvent through the element stacked in the column. Preferably, the elements swell to form a substantially tight edge seal to the cylinder wall. Because the individual elements are dimensionally stable, the column is not sensitive to orientation or handling, a problem which is common with other chromatographic media, particularly of any gel type media. A typical column is disclosed by Crowder, III et al., U.S. Pat. No. 4,384,957, incorporated by reference herein.

In a preferred embodiment, the modified polysaccharide media of the invention in fibrous form is shaped into a jelly-roll configuration, as disclosed in copending U.S. patent application Ser. No. 505,532, filed June 17, 1983 by Leeke et al., or in configuration similar to that described for mechanical filtration in U.S. Pat. Nos. 2,539,767 and 2,539,768 to Anderson, and available from AMF, Incorporated, Cuno Division, as Micro- Klean ® Filter Cartridges, and described in a brochure of the same title, 1981, herein incorporated by reference.

The jelly roll configuration is normally shaped into a cartridge. Utilization of the cartridge has several advantages. Production scale flow rates of 200–500 ml/min can be utilized with the cartridge, depending on the application. The cartridges can be autoclaved separately by rolling/encasing in Kraft non-shredding paper. They can be housed in special housings made of polysulphone tubing with acetyl end caps, where the cartridge can be autoclaved. The cartridges show long term stability with respect to their binding capacities at room temperature storage.

The rigidity of the matrix allows the column to be operable in unrestricted diameter for high volume processes. The column volume is virtually unaffected by changing pH or ionic strength in the buffer solution. Such a system can be equilibrated and regenerated in a short period of time, eliminating cumbersome procedures of column preparation and regeneration.

USES

The ion exchange, affinity, reverse phase, or bioactive materials of the invention can be used in any of the well known prior art processes of ion exchange, affinity or reverse-phase chromatography, or as supports for bio-reactors, depending on the extent to which the polymer modifier of the polysaccharide substrate is itself bonded to by the polyionene.

The materials obtained in the present invention have unique properties over materials used heretofore. A binary system formed by mixing modified polysaccharide, e.g., cellulose, with other type of polysaccharide, such as microcrystalline cellulose, and forming a fibrous sheet (without the addition of extra particulate material) has the advantage of lacking silica materials, which normally shows nonspecific adsorption of proteins. A highly controllable degree of swelling which can be readily controlled by adjusting the multiple variables present in the system, allows the replacement of unmodified microcrystalline cellulose by other mechanical strengtheners, has low production cost, and high exchange capacity or anchoring capacity, which can, in any event, be modified by controlling the ratio of comonomers (a) and (b).

A ternary system formed from modified polysaccharide, modified or unmodified particulate, and modified or unmodified fibers other than polysaccharide has the advantage of potential maximization of swelling, rigidity and capacity obtainable through varying the multiple variables present in the system. Flow rates can be controlled by varying the ratio of organic to particulate (especially silica) components without significant loss of capacity. In addition, such a system shows advantages over prior art systems using nonmodified celluloses in that, in many instances, no refined pulp is necessary, since the polymer linked on the polysaccharide will function as well as refined pulp in bridging particles to the fiber surfaces. The polymeric components in the present system may also function as binder resins; therefore, addition of resins to the slurry can, if desired, be eliminated.

While ordinarily the prior art has relied on materials with high surface area to bind the maximum number of chemical groups thereon, the materials of the present invention provide means of binding multifunctional groups per each polysaccharide molecule. As long as these functional groups are made accessible for ion exchange or anchoring, the preparation is no longer limited to high surface area materials.

In any event, as a result of transformation of the modified polysaccharide substrate with polyionene, an additional dimension of biocidal and bacterial entrapment results in separation matrices as above described which serve to decontaminate biological and pharmaceutical solutions from microorganism-originated contaminants.

The polyionenes of the present invention are insolubilized by bonding to the modified polysaccharide substrate. The polyionenes contain both hydrophobic and charged groups for bacterial adsorption. By the insertion of coupling groups and/or linker arms, the higher molecular weight bioadsorptive compounds are bonded to the modified substrate but still provide a degree of flexibility thereto, and distortion of the structural conformation of proteins in solution is avoided, thereby retaining the biological activity thereto.

In protein separations and purifications, the key factor which ought to be avoided is possible damage to the protein molecules. In the present invention, this is avoided by using biocompatible materials such as polysaccharides with only limited amounts of organic polymers. The materials are swellable and provide for very little denaturation of protein. Nonspecific adsorption of biopolymers is decreased, since both acrylic and saccharide polymers show very low amounts thereof, and are hydrophilic in nature.

Another area of design flexibility and design control is in the possible adjustment of the length of the acrylic polymer carrying the various ion exchange or anchoring groups. The variability of the polymer length not only may eliminate steric hindrance due to solute or ligand accessibility, but also minimizes leakage of the ligand from the matrix. The polymer "arm" should not be too long to avoid potential internal hydrophilic interaction, such as folding back. An "arm" of about 5 to 20 atoms is generally ideal for attaching the bioligands.

By the use of well-known anchoring groups for affinity ligands or biomolecules, the materials can incorporate all of the synthetic methods developed in prior art commercial materials, such a Sephadex ® or Sepharose ®.

The matrix is chemically and physically stable with minimum change of dimensional stability upon contact with salt and eluents.

Additionally, however, the presence of the polyionene provides an exceptional capacity for bacterial decontamination of the solutions being processed.

The polyione-transformed modified polysaccharide separation matrices of this invention, also called the stationary phase below, are useful in the same manner as the prior art separation matrices or stationary phases.

Further, as is understood by those skilled in the art, while the above description has focused on polyionene-transformed modified polysaccharides as the separation matrix, any substruate may be equally suitable for polyionene transformation so long as there exists a mechanism for bonding the polyionene thereto. For example, co-pending application Ser. No. 758,036, filed concurrently herewith, discloses a polyionene-transformed microporous membrane for separating contaminants of microorganism origin from biological liquids. Essentially any and all previously known or yet to be discovered separation matrices which satisfy the physical characteristics of rigidity, porosity and stability, and which further lend themselves to polyionene transformation are within the scope of this invention.

In one embodiment, the stationary phase, in sheet form, is used as the stationary phase in a chromatography column.

Figure 7:
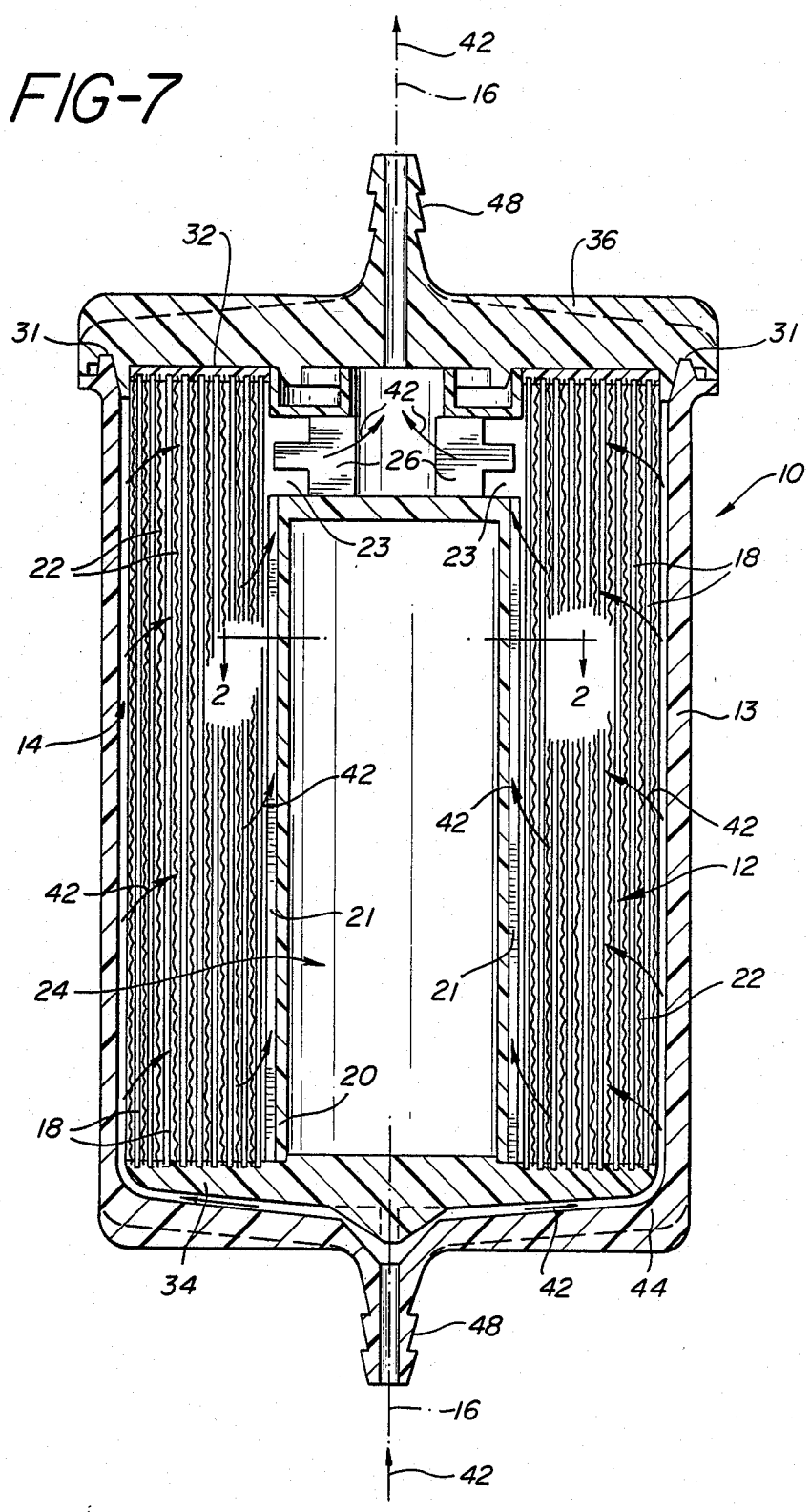
FIG. 7 is a partial sectional view of a side elevation of one embodiment of the chromatography column of this invention.

Referring to FIG. 7, the column, which may be in cartridge form, generally designated 10, is comprised of a cylindrical stationary phase 12, and cylindrical tube 13, which form a cylindrical chamber 14 which acts as a housing for the stationary phase 12. The solid stationary phase 12 can be inserted into chamber 14 formed by a glass, metal or polymeric tube or cylinder 13 having a diameter somewhat larger than the external diameter of the stationary phase 12. Suitable fluid admission, collection and monitoring systems can also be employed with the column as in conventional analytical and preparative columns. The stationary phase 12 is positioned within the chamber 14 and preferably has a longitudinal axis 16 coaxial with the axis of the cylindrical chamber 14. Optionally, a plurality of cartridges may be placed in a single housing in various configurations to effect parallel and/or series flow between the cartridges (not shown). The solid stationary phase has chromatographic functionality and is effective for chromatographic separation.

Figure 8:
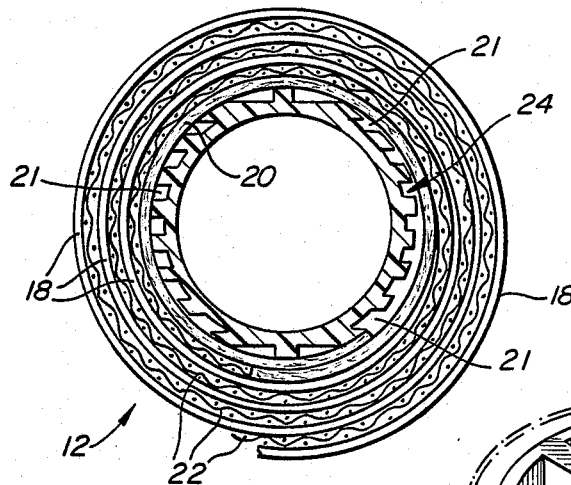
FIG. 8 is an enlarged cross-sectional view taken along line 2—2 of FIG. 7.
Figure 9:
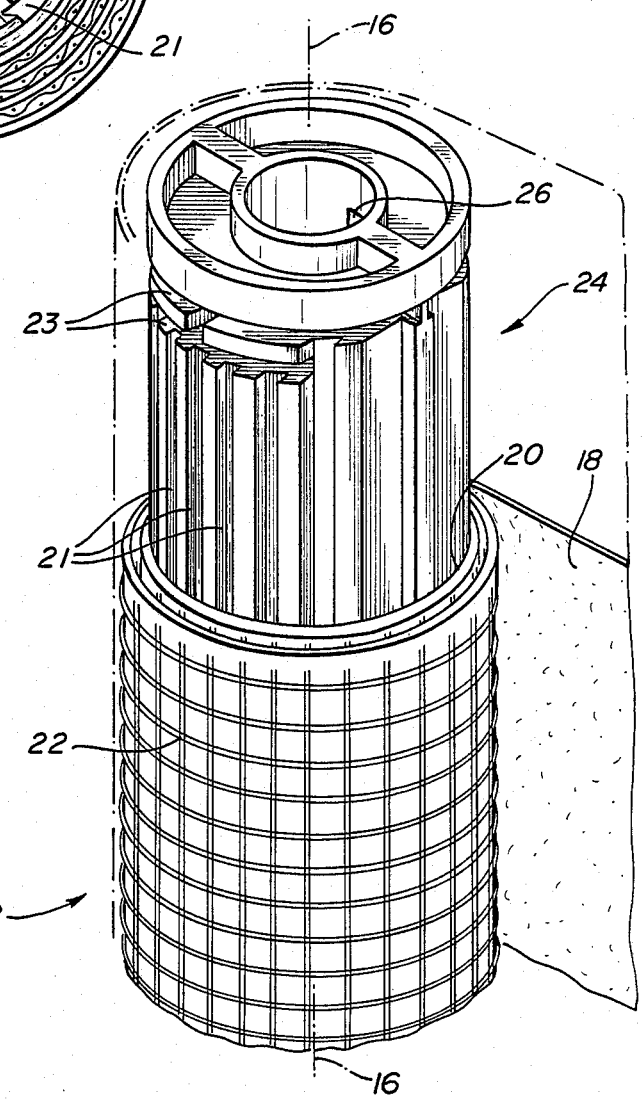
FIG. 9 is a perspective view of the core with a portion of the solid stationary phase broken away therefrom showing the spirally wound chromatographic media and spacer means therebetween.

Referring to FIGS. 8 and 9, the stationary phase 12 is constructed of a swellable fibrous matrix 18, usually hydrophilic swellable, in sheet form which is the active media for chromatographic separation. The chromatographic media in sheet form 18 is sandwiched between a single non-woven mesh 22 or plurality of mesh. The composite sheet of chromatography media 18 and mesh 22, preferably non-woven, is spirally wound around a cylindrical core 24 having a longitudinal axis 16 to form a plurality of layers around the axis 16. The core 24 is provided with a plurality of longitudinal and axially oriented channels 21 for directing the liquid into circumferential channels 23 which are in fluid communication with core 24. The mesh 22, due to the openness and thickness thereof, acts as a spacer means between each layer of media 18 which permits the controlled swelling of the media and enhances the distribution of the sample flowing through the stationary phase 12. The cylindrical core 24 is provided with apertures 26 near the top thereof for the flow of sample from the circumferential channels 23 into the open interior of the core.

Figure 10:
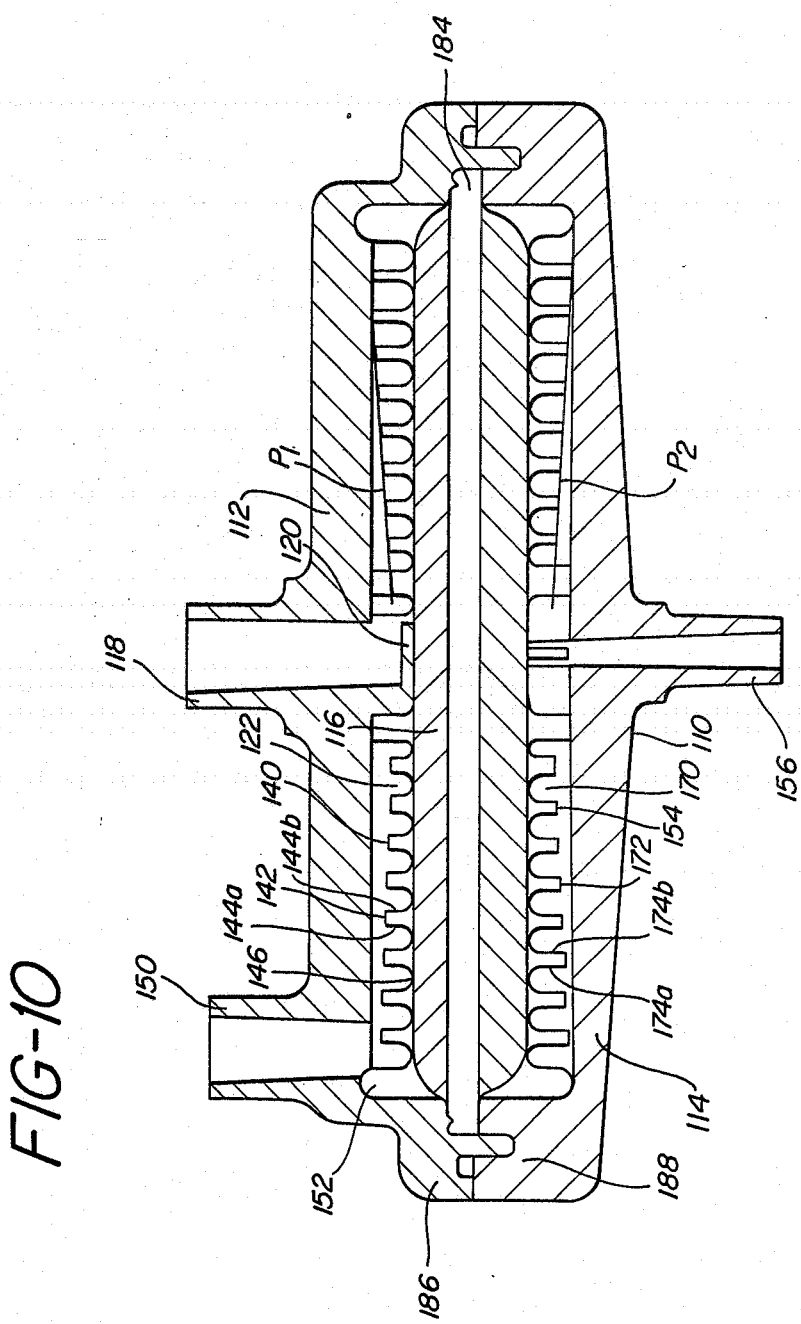
FIG. 10 is a cross-sectional view of another embodiment of the invention wherein the chromatography column is in disc configuration.

Referring to FIG. 10, the wound composite sheet 18 and 22 and core 24 are then capped by stationary phase end caps 32 and 34. The stationary phase end caps 32 and 34 of this subassembly are sealed by thermoplastic fusion to the core 24 and also to the ends of the composites 18 and 22. The subassembly, comprising 18, 22, 24, 32 and 34 is then slipped into chamber 14. The cylinder end cap 36 is then thermoplastically fused to the top edge 31 of cylinder 13. The fluid or sample 42 can thus flow radially from the outside through the solid stationary phase to the open channel 21 of core 24, since the interior and exterior are completely separated by the solid stationary phase and sealed off by stationary phase end caps 32 and 34.

The preformed stationary phase end caps 32 and 34 are preferably applied to the cylindrical solid stationary phase 12 by heating an inside face of the thermoplastic stationary phase end cap to a temperature sufficient to soften a sufficient amount of the stationary phase end cap to form a thermoplastic seal with the ends of the core 24 and composite sheet 18 and 22. All of the edges are then embedded into the softened material. The softened material is then hardened, typically by ambient conditions, to form a thermoplastic sealing relationship between the sealing surface of the stationary phase end caps 32 and 34, the core 24 and the ends of the solid stationary phase 12 to form a leak-proof seal. Such methods of applying stationary phase end caps are well known in the filtration art. See, for example, U.S. Ser. No. 383,383 and U.S. Ser. No. 383,377, filed on May 28, 1982, to Meyering et al. and Miller, respectively. Optionally, the stationary phase end caps can be molded integrally in situ onto the solid stationary phase.

Stationary phase end caps of thermoplastic materials are preferred because of the ease of bonding, but it is also possible to use thermo-setting resins in a thermoplastic, fusible or heat-softenable stage of polymerization, until the bondings have been effected, after which the curing of the resin can be completed to produce a structure which can no longer be separated. Such a structure is autoclavable without danger of destroying the fluid tight seal, the solid stationary phase 12, and the stationary phase end caps 32 and 34. Thermoplastic resins whose softening point is sufficiently high so that they are not softened under sterilizing autoclaving conditions are preferred for biomedical use. Exemplary of the plastic materials which can be used are polyolefins.

Referring to FIG. 7, the preferred column 10 has a stationary phase end cap 34 on one end which does not open to the exterior of the subassembly 18, 22, 24, 32, and 34 but is closed off. This stationary phase end cap 34 can nest on the bottom end wall 44 of cylinder 13 while still permitting the flow of sample 42 into chamber 14 around the outside of stationary phase 12, or this lower stationary phase end cap 34 of the subassembly 18, 22, 24, 32 and 34 is in spaced apart relationship from the bottom end wall 44 of cylinder 13, thus permitting the flow of sample 42 into the chamber 14.

The upper end of cartridge 40 has a cylinder end cap 36 which is in fluid communication with channels 21 of cylindrical core 24 thus permitting the flow of fluid from the outer periphery of cylindrical core 24 to the center of core 24 to the outside of cylinder end cap 36. The cylinder end cap 36 has molded thereon fitting 48 for fluid connection through a collection means (not shown).

Referring to FIG. 8, prior to winding the chromatography media 18 on the core 24, the exterior surface of core 24 may be completely wrapped with a scrim material 20. Additionally, after winding the chromatography media 18 on the core 24, the exterior surface thereof may be completely wrapped with mesh material 22.

Figure 11:
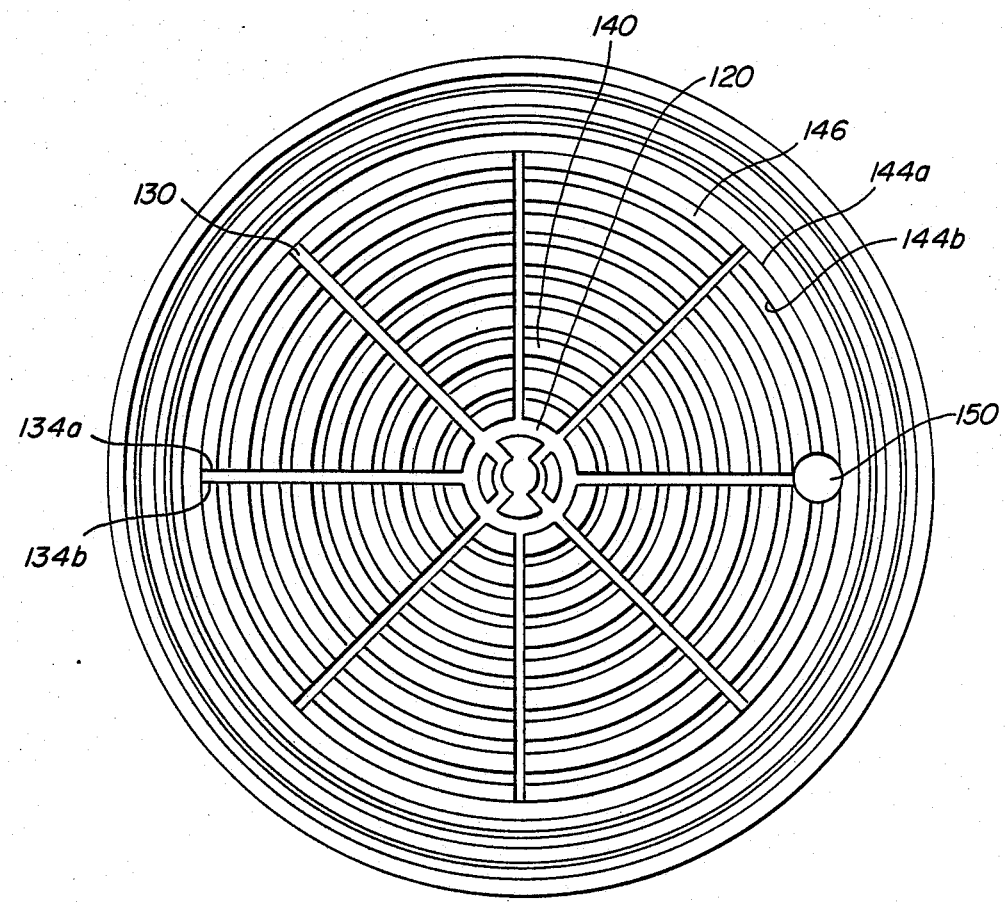
FIG. 11 is a top plan view of the inlet housing member of the invention embodiment in disc configuration.
Figure 12:
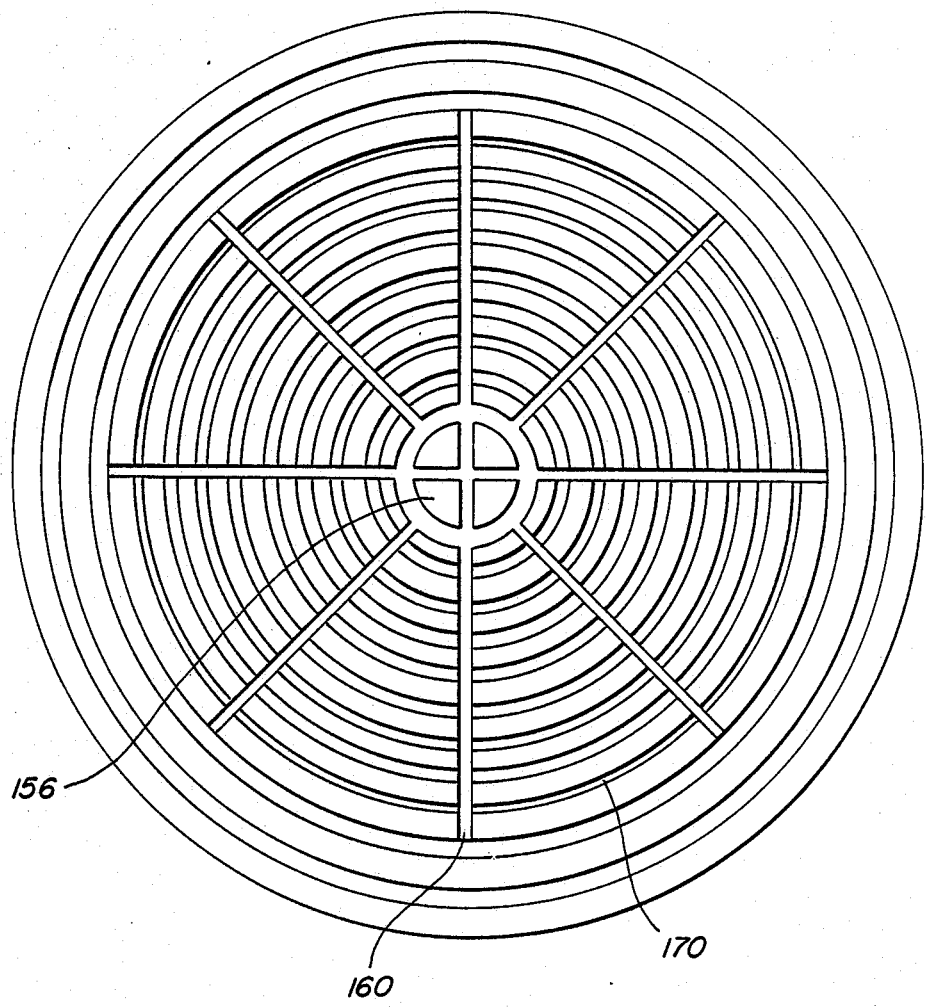
FIG. 12 is a top plan view of the outlet housing member of the invention embodiment in disc configuration.

FIGS. 10 through 12 depict another embodiment of the chromatography column of this invention, the embodiment wherein the column is in disc configuration, again wherein like character references indicate like parts.

Referring to FIGS. 10-16, the column in disc configuration, generally designated 110, comprises an inlet housing member 112, an outlet housing member 114, and a stationary phase 116.

The inlet housing member 112 comprises a sample inlet means 118, baffle means 120, and sample distribution means 122. The sample inlet means 118 is in communication with the sample distribution means 122.

The sample distribution means 122 comprises plural radial distribution channels or grooves 130 and plural concentric distribution channels 140, the radial distribution grooves 130 and concentric distribution channels 140 being in communication with each other and with inlet means 118. Radial distribution grooves 130 comprise distribution groove bottom portions lying in a plane represented by line $P_1$ in FIG. 10 and $P_1'$ in FIG. 12, and distribution groove wall portions 134a and 134b. Concentric distribution channels 140 comprise concentric distribution channel bottom portions 142, concentric distribution channel wall portions 144a and 144b, and concentric distribution channel apex portions 146.

Optionally, the inlet housing member 112 may contain a venting means 150, the function and operation of which will be defined below. The venting means is in communication with a chamber 152. Chamber 152 is formed by inlet housing member 112 and outlet housing member 114 (see FIGS. 10 and 16). Chamber 152 contains the stationary phase 116.

The outlet housing member 114 comprises a sample collection means 154 and sample outlet means 156, sample collection means 154 being in communication with sample outlet means 156.

Sample collection means 154 comprises plural radial collection grooves 160 and plural concentric collection channels 170. Radial collection grooves 160 and concentric collection channels 170 are in communication with each other and with sample outlet means 156.

Figure 16:
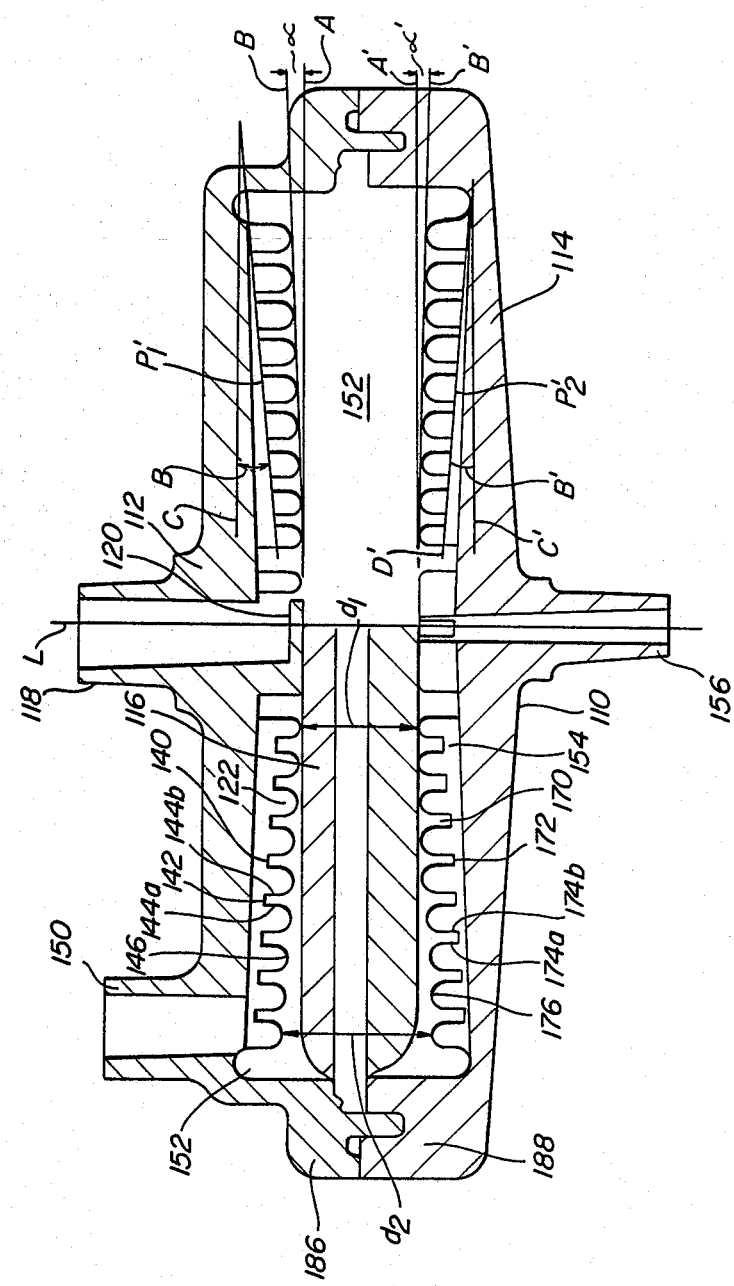
FIG. 16 is a cross-sectional view of a preferred configuration for the invention column in disc configuration. In this configuration, the housing in disc configuration forms a radially outwardly expanding chamber. A portion of the spacer means is removed for clarity.

Radial collection grooves 160 comprise radial collection groove bottom portions lying in a plane represented by line $P_2$ in FIG. 10 and $P_2'$ in FIG. 16, and radial groove wall portions 164a and 164b. Concentric collection channels 170 comprise concentric collection channel bottom portions 172, concentric collection channel side wall portions 174a and 174b and concentric collection channel apex portions 176.

Figure 13:
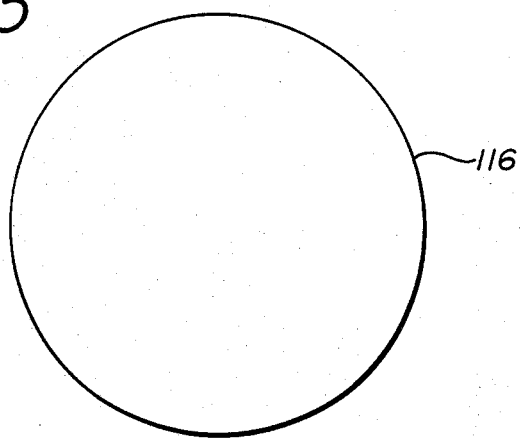
FIG. 13 is a top plan view of one embodiment of the stationary phase of the invention column in disc configuration.
Figure 14:
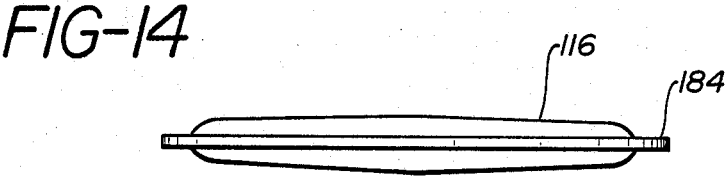
FIG. 14 is a side elevation of one embodiment of the stationary phase of the invention column in disc configuration.
Figure 15:
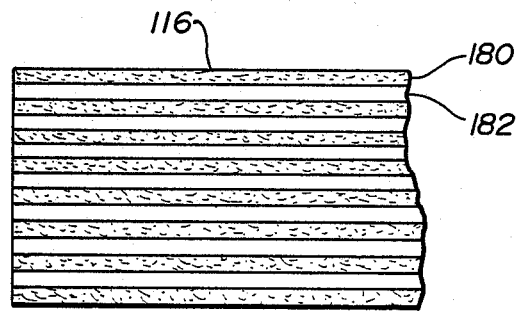
FIG. 15 is a cross-sectional view of one embodiment of the stationary phase of the invention column in disc configuration depicting a plurality of layers of separation media and spacer means interposed between adjacent layers of said separation media, prior to the sonic welding of the peripheral edges.

Stationary phase 116 has chromatographic functionality and is effective for chromatographic separation. Referring to FIGS. 13, 14 and 15 in particular, the stationary phase 116 may comprise a plurality of layers of a swellable fibrous matrix 180 in sheet form, having chromatographic functionality and being effective for chromatographic separation, and a spacer means 182 between each adjacent layer of swellable fibrous matrix 180. This configuration is best shown in FIG. 15, a cross-sectional view of one embodiment of the separation phase 16.

The swellable fibrous matrix 180 is preferably hydrophilic swellable and comprises the active media for chromatographic separation. The spacer means 182 may be typically a woven or non-woven mesh similar to mesh 22 of FIGS. 8 and 9 above and is further described below. The mesh, due to the openness and thickness thereof, acts as a spacer means between each layer of swellable fibrous matrix 180 and permits the controlled expansion thereof without closing off the porous structure of the media, thereby enhancing the distribution of the sample flowing through the stationary phase 116.

As may be seen from FIG. 14, a typical manner of conforming the stationary phase 116 is to produce a "sandwich" of alternating layers of swellable fibrous matrix in sheet form and layers of spacer means, with the periphery of the sandwich compressed into a fluid tight configuration 184. Typically, the peripheral edges of alternating discs of swellable fibrous matrix 180 and spacer means 182 are joined. Preferably, the fibrous matrix 180 contains or has bonded therein a thermoplastic polymeric material. Similarly, in a preferred embodiment, spacer means 182 also is made of or contains thermoplastic polymeric materials. In this configuration, the edges may be uniformly joined by appropriate heat treating, e.g. sonic welding. As may be seen from FIG. 10, in a preferred embodiment, the fluid tight peripheral configuration 184 is itself contained in a fluid tight, hermetic seal formed by the mating edges 186 and 188 of, respectively, the inlet housing member 112 and the outlet housing member 114. In this manner, sample entering through inlet means 118 must pass through stationary phase 116 prior to exiting through outlet means 156.

The disc configured chromatography column of FIGS. 10-16 is formed using conventional and well known fabrication techniques. Typically, the stationary phase 116, a preformed "sandwich" of alternating layers of swellable fibrous matrix and spacer means, with peripheral edges sonically welded and configured as in FIG. 16, is placed in inlet housing 112 and outlet housing member 114 is placed thereover. Subsequently, the mating edges 186 of the inlet housing member 188 and of the outlet housing member 190 are joined to form an airtight and fluid tight seal. In one embodiment, the edges are sealed by sonically welding same, the technique described in Branson Sonic Power Company, Danbury, Conn., Information Sheet PW-3, 1971, incorporated by reference herein.

Vent means 150, as mentioned above, represents an optional configuration of the disc embodiment of the column. Its purpose is to allow air in the column to exit the column during use. Typically, vent means 150 is adapted to be sealed off when all air has been removed from the system. In an alternative embodiment, vent means 150 contains a hydrophobic media which will allow the passage of gases but not liquids, as disclosed in U.S. Pat. No. 4,113,627, incorporated herein by reference.

In a preferred embodiment, depicted by FIG. 16, chamber 152 is radially outwardly expanding. By the term "radially outwardly expanding" is meant that the volume at the interior chamber is less than the volume at the periphery of the chamber. In this configuration, referring to FIG. 16, the distance between distribution means 112 and collection means 114 at the interior, $d_1$, is less than the distance between distribution means 112 and collection means 114 at the periphery $d_2$.

Because the stationary phase 116 is hydrophilic swellable, sample solution on contact with separation phase 116 causes the separation phase to swell. As the separation phase swells, the pressure differential between the inlet and outlet sides of the separation media increases, thereby restricting sample flowthrough. By designing a housing as described above, i.e. in radially outwardly expanding configuration, the pressure differential between the inlet and outlet sides of the stationary phase decreases towards the periphery, thereby maximizing utilization of the chromatographic separation function of the stationary phase and substantially increasing the adsorption capacity of a given unit.

In another preferred embodiment, also depicted in FIG. 16, the volume of each succeeding concentric distribution channel 140 and concentric collection channel 170 increases from the interior to the periphery of the chromatographic column. In this manner, clogging of the channels by the swelling of the hydrophilic swellable stationary phase is vitiated, thereby promoting uniform distribution of sample and maximum utilization of column capacity.

In the embodiment depicted in FIG. 16, lines A, A', C and C' are lines which represent cross-sectional view of parallel planes which are perpendicular to the longitudinal axis L of the chromatography column. Lines B and B', respectively, represent cross-sectional views of planes which are substantially tangent to the apices 146 and 176 of concentric distribution channels 140 and concentric collection channels 170. Planes B and B' form angles $\alpha$ and $\alpha'$ with planes A and A'. Thus, planes B and B', at angles $\alpha$ and $\alpha'$ to planes A and A', respectively, define a radially outwardly expanding chamber 152, which in turn defines the limits of expansion of stationary phase 116. As described above, the optimal configuration for the radially outwardly expanding embodiment is such that stationary phase 116, in maximally swelled status, is just touching the most peripheral apices 146 and 176. It is to be understood that angles $\alpha$ and $\alpha'$ may be the same or different and may vary with the number of layers of swellable fibrous matrix and the particular matrix in use. Typically, $\alpha$ and $\alpha'$ are about $2\frac{1}{2}°$.

Lines D and D', respectively, represent cross-sectional views of planes which contain concentric distribution channel bottom portions 142 and concentric collection channel bottom portions 172 and define angles $\beta$ and $\beta'$ with planes C and C'. Thus, planes D and D', at angles $\beta$ and $\beta'$ to planes C and C', respectively, define the slope of the increasing depth of channels 140 and 170. In the embodiment of FIG. 10, $\beta$ and $\beta'$ are typically each about 5°. However, these angles may be varied, both with respect to one another and absolutely.

In similar manner, it is within the scope of the present invention to configure a chromatographic column such that radial distribution grooves 130 and/or radial collection grooves 160 increase in volume from the interior to the periphery of the column. Such a configuration is disclosed in U.S. Pat. No. 3,361,261, incorporated by reference herein.

As is understood by those skilled in the art, it is desirable to minimize the hold-up volume of a chromatographic column. With this in mind, an optimal design for a radially outwardly expanding chamber is that where the distance $d_2$ is such as to allow the swellable stationary phase to swell to its maximum, but with no unused space left. In this manner, the pressure differential at the periphery is minimized, while at the same time reducing hold-up volume to its lower limit as well. This housing configuration permits as well the use of a single layer of fibrous matrix or a plurality of layers of fibrous matrix with no spacer means interposed between layers. The radially outwardly expanding chamber coacts with the thus configured stationary phase to uniformly distribute sample thereacross.

In order to provide a chromatographic media matrix which is coherent and handleable, it is desirable that at least one of the components which go into forming the porous matrix be a long, self-bonding structural fiber. Such fiber gives the stationary phase sufficient structural integrity in both the wet "as formed" condition and in the final dry condition. Such a structure permits handling of the phase, in particular a sheet, during processing and at the time of its intended use. Preferably, the sheets which form the chromatographic media are formed by vacuum felting an aqueous slurry of fibers. The sheets may also be pressure felted or felted from a non-aqueous slurry. The sheet shows a uniform high porosity, with excellent flow characteristics, and is substantially homogeneous. In general, the media can range in thicknesses from about 5 mils to about 150 mils (dry); however, thicker or even thinner media may be utilized provided the sheet can be sprially wound or layered to produce a column which can perform as described above. The media can swell to at least 25% this thickness, and generally greater, e.g. two to four times, this thickness.

It is important when constructing the chromatography column of this invention that the chromatographic media used in the column be of uniform thickness throughout its length and width and that the media have a substantially uniform density throughout. It is preferred that the layer of media be substantially homogenous with respect to itself; however, for certain applications and material, it is understood that non-homogeneous construction may be employed.

Since the solid stationary phase is intended in use to effect separation by maintaining a substantial pressure differential across the solid stationary phase, it is essential that the solid stationary phase have a sufficient degree of compressive strength to withstand deformation under such loads as may be imposed upon it. Such compressive strength must not only exist in the media itself but in the spacer means and the internal core upon which the chromatography media, or solid stationary phase is compressed.

Due to the swellability of the media, a key element of this invention is the spacer means between each layer of the media and/or the coaction of the chamber wall and the fibrous matrix. The spacer means permits controlled expansion of the media and enhancement of the distribution of sample flowing through the stationary phase. The spacer means located between each layer of the swellable chromatographic media provides for the distribution movement of the sample as the sample passes through the solid stationary phase. The spacer means functions to uniformly control thickness and density of the chromatographic media during use. In addition, the spacer means can serve as a backing or support for the layer of chromatographic media. This latter aspect is particularly useful during the manufacturing phase.

It is preferred that the spacer means be composed of a material which is inert with respect to the chromatographic process. By inert, it is meant the material does not adversely affect the function of the solid stationary phase.

Referring to FIGS. 8 and 9, the spacer means comprises the mesh 22. Alternatively, where the column design is as depicted in FIGS. 10–16, the spacer means 182 may also comprise a mesh, or scrim and mesh. A scrim material can function to channel, to a certain extent, the sample flowing through the media and substantially evenly disperse the sample axially and circumferentially across the media. The mesh material provides spacing between the media to permit controlled expansion thereof to prevent the "cut-off" to flow therethrough by compression of the permeable media and also assists in distributing or channeling the sample flowing through the media.

The mesh material is an open type of material having openings ranging, for general guidance, from 1/16 inch to $\frac{1}{4}$ inch.

It should be noted that the thickness of the spacer means, i.e. the scrim and particularly the mesh material, and the pore size of each to be used may be readily determined by one skilled in the art by performing tests which vary these factors. Such factors as the openness and thickness of these spacer means are highly dependent on the type of media utilized, e.g. swellability, wettability, thickness, chemical composition, etc., the flow rate of the sample through the stationary phase, the surface area of the stationary phase, e.g. number of windings, thickness of media, diameter of stationary phase, etc. Is is thus very difficult to clearly specify these variables, other than to say that these may be determined by either trial and error or more elaborate testing procedures to determine the optimum parameters.

The preferred mesh material, at this time, is polypropylene CONWED (Grade TD-620).

The overall width of the stationary phase in accordance with the present invention can be infinite, the actual diameter being limited only by practical considerations such as space requirements. Since the diameter or width of the overall column can be increased without theoretical limitation, the sample size or amount of substance to be separated in the bed is not limited. Thus, the diameter can be increased to separate the desired amount of sample substance to be produced.

In operation, the sample is driven through the stationary phase and separated into distinct chromatographic fractions by the chromatographic media. The spacer means induces and permits flow of this stream as it moves through the column and therefore provides for improved resolution and utilization of the media's potential capacity.

Referring to FIG. 7, the sample is preferably introduced at the bottom of the column flowing to the outer surface of the solid stationary phase and then flowing radially inward through the layers of chromatographic media and spacer means into the channels 21 of core tube 24 and is withdrawn centrally. It is apparent, from what has been set forth above, that the radial flow can also be caused to circulate in the opposite direction.

Referring to FIG. 10, sample is preferably introduced at the inlet 118, passes to distribution means 122, is substantially uniformly distributed over the surface of the stationary phase 116 by radial distribution grooves 132 and concentric distribution channels 130, and passes through radial collection grooves 140 and concentric collection channels 170 and exits through outlet 156.

The chromatographic columns of this invention may be used for any of the well-known chromatographic separations usually performed with conventional columns. Additionally, the columns of the present invention may be found useful in the areas where conventional columns are impractical.

The novel columns of this invention can be used for separations in the analytical and preparative fields. The columns can be connected to all common types of chromatographic equipment. Several columns or cartridges of solid stationary phase can be connected in series or parallel. In large units, the columns can contain identical or different chromatographic media and can be of identical or different length and/or diameter. See for example Daly et al., application Ser. No. 611,662, filed May 18, 1984, incorporated by reference herein. It has been found that the aforedescribed stationary phase produces unexpected results in that the flow of sample through the column is enhanced without destroying the adsorptive capacity of the media. Additionally, when protein and dye staining tests were performed it was found that the stationary phase of this invention provided even distribution of sample flow therethrough without an increase in pressure drop when compared to a stationary phase not utilizing the spacer means described herein.

The stationary phases decrease total processing time and when used with the proper chromatographic media has excellent binding capacity. The stationary phases may be used with standard type pumps, gravity feed, or syringes, utilized, in their preferred mode, at from 1 to 50 PSI, and even under vacuum. The stationary phases of chromatographic media are totally enclosed and completely self-contained to ensure sterile conditions. Due to the fact that the solid stationary phase is manufactured in a factory and assembled therein, each is virtually identical to the other, does not vary as in previously known columns and eliminates the dependence upon packing expertise.

It has surprisingly been found that when a column configured as in FIG. 16 is employed, the actual capacity is substantially increased over that of the column of FIG. 10. In this way, the actual capacity more closely approximates the theoretical capacity of the column. By configuring the column to maximize sample distribution, minimize hold-up volume, and maximize stationary phase utilization by creating a differential pressure gradient which decreases from the interior to the periphery, the useful and effective life of the column is substantially improved.

EXAMPLES

Having now generally described this invention, the same will be better understood by reference to certain specific examples which are included herein for purposes of illustration only, and are not intended to be limiting of the invention unless otherwise specified.

Example 1

Poly(diethylaminoethyl methacrylate)-g-Cellulose (a) Recipe

| Reagent | Quantity |
|---|---|
| Microcrystalline cellulose | 10 g |
| Diethylaminoethyl methacrylate | 25 cc |
| Glycidyl methacrylate | 2.5 cc |
| Ammonium persulfate | 1 g |
| Sodium thiosulfate | 1 g |
| Water | 500 cc |

(b) Procedure

1. Cellulose was well dispersed in water in a reactor.
2. Diethylaminoethyl methacrylate and glycidyl methacrylate were well mixed before pouring into the reactor.
3. After pouring the monomers into the reactor, the mixture was stirred for 5 minutes.
4. Ammonium persulfate and sodium thiosulfate were dissolved in 20 ml water; and then poured into the reactor.
5. The reactants were stirred for 20 minutes at 15° C. to 40° C.; the temperature was then increased to 80° C.
6. Stirring was maintained for 1 hour in the range of 80°–90° C.
7. A period of 0.5 hour was allowed to cool down the products.
8. The product was filtered and washed well with water and acetone.

(c) Results

The number of available DEAE functional groups was determined by titrating with 0.1M HClO$_4$ in glacial acetic acid (0.1M HCl in aqueous solution) on Brinkman Potentiograph E 536. The instrument was calibrated by measuring commercial DEAE cellulose as the control, and capacity was expressed as milliequivalent (mEQ) per gram of dry material. The copolymerized cellulose showed approximately three times more capacity than that of the cellulose made from the conventional prior art derivative method.

The results were further confirmed by the measurement of albumin adsorption capacity. This was done by preparing a fibrous sheet, cutting into discs and packing in a 76 mm size column. Albumin in phosphate buffer solution was pumped through the column and later eluted with 1N NaCl solution. The amount of albumin measured at 280 nm O.D. showed the following results (Table 1):

TABLE 1
Beaker Test on DEAE Media

| Sample No. | Sample Weight (Dry/Wet) | pH Media in Buffer | 0.1 M NaOH Added | Media In BSA | BSA Conc. | Capacity Test A280 t = 1 hr | (Mg/g) |
|---|---|---|---|---|---|---|---|
| 1 | 1/9.9 | 5.63 | 2.7 ml | 6.25 | 1030 mg | 0.25 | 991 |
| 2 | 1/8.7 | 5.5 | 3.2 | 6.25 | 1030 | 0.33 | 978 |
| 3 | 1/8.33 | 5.68 | 2.8 | 6.25 | 1025 | 0.38 | 966 |
| 4 | 1/7.69 | 5.68 | 2.8 | 6.25 | 1025 | 0.69 | 918 |
| 5 | 1/7.69 | 5.68 | 2.8 | 6.25 | 1895 | 4.5 | 1195 |
| 6 | 1/8.7 | 5.57 | 3.9 | 6.30 | 1025 | 0.19 | 995 |
| 7 | 0.88/8.0 | 5.5 | 3.6 | 6.30 | 1533 | 1.49 | 1298 |
| 8 | 1.0/8.33 | 5.52 | 3.3 | 6.25 | 1030 | 0.36 | 974 |
| 9 | 1.0/8.33 | 5.52 | 3.3 | 6.25 | 1236 | 0.97 | 1085 |

Example 2

Quaternized Poly(diethylaminoethyl) methacrylate)-g-Cellulose (a) Recipe

| Reagent | Quantity |
|---|---|
| Poly(diethylaminoethyl methacrylate)-g-cellulose (Example 1) | 5 g |
| 1,6-Dichlorohexane or 1,4 dichlorobutane | 3 cc |
| Potassium iodide | 0.1 g |
| Isopropanol | 100 cc |
| Water | 100 cc |

(b) Procedure

1. A round neck flask was filled with wet poly (diethylaminoethyl methacrylate)-g-cellulose, 1,4-dichlorobutane, potassium iodide and isopropanol.
2. The reaction mixture was refluxed overnight.
3. The product was filtered and washed well with acetone and water.
4. The sample was acidified with $10^{-2}$N HCl, then washed well with water.

(c) Results

The results demonstrate the effectiveness of 1,6-dichlorohexane as cross-linker on fixing the charged groups. 1,6-dibromo or diiodo hexane have also been applied as cross-linkers with success.

To improve quaternization percentage, water soluble quaternization reagents, halo compounds, such as 1,3-dichloro-2-propanol, 1-chloro-2-propanol, chloroacetic acid, methyl chloroacetate and chloroethyl diethylamine can be applied with success. The quaternized (QAE) media derived from ethyl iodide showed exceptionally high BSA binding capacity in the pH range from 7 to 8.5. The results are shown in Tables 2 and 3.

TABLE 2
Quarternization Percentage in QAE Media Derived from Different Q-Reagents

| Sample No. | Q-reagent | Q (%) |
|---|---|---|
| QAE-1 | 1-chloro-2-propanol | 13 |
| QAE-2 | 1,2-dichloro-2-propanol | 77 |
| QAE-3 | methyl chloroacetate | 83 |
| QAE-4 | chloroethyldiethylamine | 82 |
| QAE-5 | ethyl iodide | 80 |

TABLE 3
BSA Capacity of Various QAE Media vs. pH of Phosphate Buffer Solution

| Sample No. | Q-reagent | BSA Cap. (Mg/g) | pH | BSA Cap. (Mg/g) | pH | BSA Cap. (Mg/g) | pH |
|---|---|---|---|---|---|---|---|
| QAE-1 | methyl chloroacetate | 1527 | 6.29 | 1027 | 7.36 | 758 | 8.69 |
| QAE-2 | 1-chloro-2-propanol | 1376 | 6.30 | 671 | 7.30 | 336 | 8.12 |
| QAE-3 | 1,2-dichloro-2-propanol | 1466 | 6.25 | 676 | 7.29 | 387 | 8.18 |
| QAE-4 | ethyl iodide | 1391 | 6.27 | 1015 | 7.59 | 816 | 8.26 |
| QAE-5 | 1-chloro-2,3-propanediol | 1397 | 6.28 | 692 | 7.33 | 367 | 7.98 |
| QAE-6 | chloroethyl diethylamine | 1483 | 6.27 | 559 | 7.39 | 290 | 8.60 |
| DEAE | — | 1625 | 6.38 | 738 | 7.32 | 296 | 7.98 |

Example 3

Preparation of Cellulose-GMA Matrix (a) Formulation

| Reagent | Quantity |
|---|---|
| Refined cellulose | 5.0 g |
| Glycidyl methacrylate | 12.5 ml |
| APS | 0.5 g |
| STS | 0.5 g |
| D.I. H$_2$O | 250 ml |

(b) Process

The cellulose was dispersed in the D.I. H$_2$O with agitation and heated to 80° C., with agitation. The glycidyl methacrylate, APS and STS were added to the reactor and the reaction permitted to proceed for one hour. The reaction was terminated and the covalently bound GMA-cellulose matrix removed, washed with 5 × 1.8 liters of D.I. H$_2$O and stored for further processing. (Conversion to polyionene-transformed matrix).

Example 4 various different types of protein molecules. The results are shown in Table 4 below:

TABLE 4

| | | Beaker Test on Media | | | | Capacity Test | |
|---|---|---|---|---|---|---|---|
| | | pH | | | | | |
| Sample No. | Sample Nature (Dry/Wet) | Media in Buffer | 0.1 M NaOH Added | Media in Protein | Protein Conc. | A280 t1 = hr | (Mg/g) |
| 1 | Ovalbumin PI = 4.6 Crude dried egg white m.w. = 43,000 50 mg/ml | 5.74 | 5.0 ml | 6.3 | 2038 | 4.37 | 1343 |
| 2 | BSA PI = 4.9 (50 mg/ml m.w. = 65,000) | 5.63 | 4.0 | 6.3 | 1811 | 3.07 | 1327 |
| 3 | Soybean PI = 4.15 Trypsin m.w. = 20,100 Inhibitor (10 mg/ml) | 5.52 | 5.0 | 6.3 | 443 | 1.55 | 200 |
| 4 | Amylo- PI = 3.5 glucosidase (20 mg/ml) | 5.60 | 4.1 | 6.3 | 954 | 4.25 | 282 |
| 5 | Pepsin PI = 2.2 (50 mg/ml) m.w. = 34,500 | 5.63 | 3.9 | 6.3 | 1744 | 2.52 | 1073 |

Preparation of Cellulose-GA Matrix (a) Formulation

| Reagent | Quantity |
|---|---|
| Refined cellulose | 5.0 g |
| Glycidyl acrylate | 12.5 ml |
| Ethoquad C/25 | 0.5 ml |
| APS | 0.5 g |
| STS | 0.5 g |
| 1.0 M HCl | 16.67 ml |
| D.I. H$_2$O | 250 ml |

(b) Process

The cellulose was dispersed in the 250 ml of D.I. H$_2$O with agitation at 80° C. and the glycidyl acrylate added to the reactor. Temperature and agitation were maintained, the APS, STS and HCl added, and the reaction permitted to proceed for one hour. The covalently bonded cellulose-GA pre-ligandized matrix was removed, washed with 7×2 liters of deionized water and stored for further further treatment. (Conversion to polyionene-transformed matrix.)

Example 5

Cellulose-GMA Matrix Modified With Methacrylic Acid (a) Formulation

| Reagent | Quantity |
|---|---|
| Refined cellulose | 5.0 g |
| methacrylic acid | 12.5 ml |
| GMA | 1.25 ml |
| APS | 0.5 g |
| STS | 0.5 g |
| D.I. H$_2$O | 250 ml |

(b) Process

The grafting-polymerization technique of Example 3 above was followed. At the end of the reaction, the matrix (CM matrix) was washed five times with 1.8 liters of D.I. H$_2$O and stored for further processing.

Example 6

A beaker test on the capacity of media prepared according to Sample 7 of Table 1 supra was carried out on

Example 7

Plasma Fractionation Using the Media of Example 2

775 ml of Cohn fractions II and III from human plasma were dissolved in 0.01M phosphate buffer at pH 6.5. This solution was added to a column (7.7 cm i.d.×4.3 cm length, vol=200 ml) containing 25 g of the media of Example 2. 2.7 g of IgG were recovered from the non-bound fractions whereas elution of bound material with 1M sodium chloride yielded 7.5 g of albumin.

Example 8

Formulation of a Sheet Containing Both Modified Cellulose and Modified Silica (a) Silanization of Silica The silanization process can be performed either in toluene or in water. The reaction mechanism involves condensation of the halide or silanol functional groups on the organo-silane with silanols on the silica surface. Therefore, the reaction conditions depend very much on the nature of the silane and the surface property of silica. The selection of silica is made based on both chemical and physical factors. Chemically, it should have a surface property favorable for silanization reactions; physically, the particle size should be large enough to permit the least amount of pressure build-up in a column up to 2 ft. length, as long as the composite structure homogeneity can be maintained in the formulation. The following three grades of silica gel from Davidson Chemicals are the choice to meet such requirements:

| Grade | Approx. Particle Size (Micron) | Surface Area (m$^2$/g) | Pore Vol. (cc/g) | Pore Dia. A | pH 5% Slurry |
|---|---|---|---|---|---|
| 922 | 50 | 750 | 0.43 | 22 | 4.0 |
| 950 | 30 | 600 | 0.43 | 25 | 6.0 |
| 952 | 70 | 320 | 1.50 | 250 | 7.0 |

The maximum pore diameter from Davidson's product is around 250 A, which can only accommodate protein molecules smaller than albumin. Controlled pore glass of 1000 A or controlled pore silica of 500 A needs to be used to facilitate the diffusion of larger protein molecules such as IgG or immune complex. DEAE or SP are introduced onto silica gel through the following route:

$$Si-OH + (EtO)_3Si(CH_2)_2OCH_2-CH\underset{O}{-\!-\!-\!-}CH_2 \longrightarrow$$

$$HOC_2H_4NH_2 \text{ or } HOC_2H_4N(C_2H_5)_2$$

$$\underset{O}{\overset{O}{Si-O-Si}}-(CH_2)_3-OCH_2-CH\underset{O}{-\!-\!-\!-}CH_2 \begin{matrix} -Si \text{ DEAE} \\ \\ -Si \text{ SP} \end{matrix}$$

$$Na_2SO_3$$

(b) Formulation of the Slurry

The modified cellulosic fiber from Example 2 and the silanized silica from (a) were mixed in a tank at 1 to 2% consistency to form a slurry according to the following formulations (Table 5):

TABLE 5

| Sample No. | Modified (Long Cellulosic) Fiber (%) | Refined Pulp (+40 CSF) % | DEAE Silica 952 % | % Retention |
|---|---|---|---|---|
| 1 | 20 | 10 | 70 | 90 |
| 2 | 30 | 0 | 70 | 80 |
| 3 | 30 | 20 | 50 | 95 |
| 4 | 50 | 0 | 50 | 90 |
| 5 | 20 | 7%(+40) & 7% (−10) | 60 | 100 |

Alternatively, copolymerization can be performed on the mixture of large and small refined pulp in the same reactor. Silica 952, being large in size (70 micron or larger), can be held by the modified cellulose alone without refined pulp. No binder is required, since the polymer on cellulose is also functional as a binder.

(c) Formulation of a Column

The slurry was cast onto a foraminous surface, vacuum felted, and dried in a conventional manner. The flat, dimensionally stable sheet was then cut to the appropriate dimensions for each type of column. The cut discs were stacked in the cylinder in an appropriate height.

(d) Discussion and Results

The above prepared matrix was cut to 9.0 mm diameter sized discs and stacked to 6-inch length with 0.85 grams of dry weight material. After following the swelling, adsorption and elution procedures, the albumin adsorption capacity was measured and the number of DEAE groups was titrated, with the results shown in the following Table 6:

TABLE 6

| Exp No. | MATRIX CHARACTERIZATION | | | CAPACITY | |
|---|---|---|---|---|---|
| | Modified | +40 Refined Pulp | Silica 952 | By Titration (mEQ/G) | Albumin Adsorption (mg/g) |
| 1 | 20% (Inact.) | 10% (Inact.) | 70% (Act.) | 0.89 | 171 182 |
| 2 | Act. | — | Act. | 2.0 | 245 249 |
| 3 | Act. | — | Inact. | 1.0 | 120 123 |
| 4 | Inact. | Inact. | Inact. | 0 | 0 |
| 5 | 100% Act. | — | — | 2.0 | 264 270 |

The results fully demonstrate the contribution of the ion exchange functional groups from the organic matrix. The enhanced capacity is achieved by making cellulose and binders all contributing their available sites for ion exchange, in addition to silica.

Example 9

Preparation of an Affinity Chromatography System

Component A: cellulosic fiber
Component B: glycidyl methacylate
Component C: glucose Method A Step 1. Coupling of C to B $$CH_2=\underset{CH_3}{\overset{|}{C}}-\underset{\underset{O}{\|}}{C}-O-CH_2-CH\underset{O}{-\!-\!-\!-}CH_2 + HO-\text{(glucose)} $$

Acid or base Catalyst $$CH_2=\underset{CH_3}{\overset{|}{C}}-\underset{\underset{O}{\|}}{C}-O-CH_2-\underset{OH}{\overset{|}{CH}}-CH_2-O-\text{(glucose)}$$

Component BC

Step 2. Formation of Polymers with Controlled Ratio of B to BC

| Component B (10%) polymerization + Component BC (90%) | Copolymer of 10% B & 90% BC |
|---|---|
| by Redox catalyst | |

Step 3. Coupling of the Above Copolymer to Component A

With excess amount of catalyst left in Step 2, the epoxy groups in Component B of the above copolymer can be coupled to cellulose, by raising the temperature to 90° C. The chemical reaction is exactly the same as Step 1, except that the Component A is in polymeric form whereas Component C is a monomer.

Method B

Step 1. Formation of Acrylic Copolymer $$CH_2=\underset{CH_3}{\overset{|}{C}}-\underset{\underset{O}{\|}}{C}-O-CH_2-CH\underset{O}{-\!-\!-\!-}CH_2 + CH_2=\underset{CH_3}{\overset{|}{C}}-\underset{\underset{O}{\|}}{C}-O-C_2H_4OH$$

Glycidyl methacrylate 90%      2 hydroxy-ethyl methacrylate 10%

↓ Potassium persulfate
  Sodium Thiosulfate

-continued

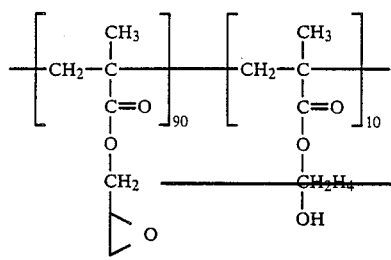

5. Fabrication of Chromatographic Columns

The materials thus prepared were formulated by vacuum felting to form composite filter pads as shown in Table 7.

TABLE 7
Formulation of Anionically Modified Pads

| Filter No. | Natural Cellulosic Fiber Soft Cotton Linter[1] | Polymer Grafted on Fiber | | Polymer Grafted on M.C.[2] Powder Cellulose | | Binder Resin Ethylene Glycol Diglycidyl Ether |
| --- | --- | --- | --- | --- | --- | --- |
| | | Type Cotton Linter with GMA | Wt. of polymer/ Wt. of Fiber | Type M.C. of 90 micron size[3] | Wt. of polymer Wt. of M.C. | |
| Cat #1 | 15% | 40% | 2.0 | 40% | 1.0 | 5% |
| Cat #2 | 20% | 40% | 1.5 | 35% | 0.5 | 5% |
| Cat #3 | 10% | 50% | 1.0 | 35% | 0.5 | 5% |

[1]Southern Cellulose Co.
[2]M.C. = microcrystalline
[3]From FMC, Grade pH 102.

Step 2.

Component C is added to the polymer on a proper molar ratio such that 90% of the available epoxy groups will be reacted with C under acid or base catalytic conditions. The remaining 10% will be left available for coupling on to the cellulose surface afterwards.

Example 10

Formation of Anionically Modified Cellulose According to the Invention

1. Cellulose Activation

Cellulose was reacted with potassium periodate in 2-5% water dispersion, with the periodate being at 2% w/v at pH 3.0 for about 2 hours at room temperature (or 30 min at 40° C.) while stirring constantly. The oxidized cellulose was vacuum felted on a screen and washed with deionized water until removal of the unreacted oxidants was complete. The conductivity of the washing water was measured until no more salt came off from cellulose.

2. Monomer Coupling to the Activated Cellulose

The activated cellulose was redispersed in deionized water at 2% consistency, and amino ethyl methacrylate (AEM) was added. The weight ratio of AEM to cellulose was approxiately 25%. The temperature was raised to 50° C. and AEM was allowed to react with the activated cellulose for 1 hour under agitation.

3. Formation of Copolymer

Glycidyl methacrylate (GMA) was then added at a weight ratio of 9 to 1 of AEM, while maintaining the reactor at 50° C. Nitrogen gas was bubbled into the reaction tank to remove oxygen gas dissolved in the aqueous system. Catalyst, such as ammonium persulfate and sodium thiosulfate mixture or organic peroxide, was added to initiate the polymerization reaction via the vinyl groups for 10 minutes. The reaction kinetics could be followed by measuring the solution turbidity or the decrease of glycidyl groups in the liquid.

4. Conversion of the Glycidyl Groups to the Corresponding Anionic Groups

The conversion of epoxy groups to carboxyl groups was performed by using potassium permanganate as oxidant at 60° C. for 4 hours. The final product was thoroughly washed with deionized water and methanol for removing unreacted species and homopolymers.

The balance of pad capacity and flow rate can be adjusted, based upon the following reaction variables:
(a) size of cotton fibers and microcrystalline cellulose powder,
(b) the amount of polymers grafted onto cellulose,
(c) the structure and nature of the polymers,
(d) the nature and the amount of the oven-dried sheets can be cut into proper sizes and can be stacked into columns for chromatographic separation of protein molecules.

Capacity Test Results

The capacity of a column with this material was measured from the amount of bovine gamma globulin (BGG) adsorbed on the column under specific conditions, and was expressed as milligrams of BGG adsorbed per gram of column material. The procedure of the test was as follows:

(a) A peristaltic pump was connected to the column with a pressure gauge installed in the line and a UV monitoring unit, to follow the protein concentration at 280 NM.

(b) Column Packing: A column packed with 25 mm dia. disks and 6-inch in height will generally have pressure across the column in the range of 1 to 10 psi, depending on the flow rate and pad porosity. The pads should be packed snugly so there is very little gap between them but not jammed with great force to fragment their structure. The total amount of pads installed in the column was weighed so the total capacity could be expressed either on the column volume or on a weight basis.

(c) Column Equilibration: The equilibration buffer was pumped through the column until the effluent had the same pH and conductivity as the starting solution. About 5 volumes of buffer were needed to reach the equilibrium conditions.

(d) Adsorption of BGG by the Cationic Exchange Column: Based on an average BGG adsorption capacity around 200 mg/g of pad, a volume of BGG solution was poured into a graduated cylinder so that there were about two volumes of the amount of BGG required to saturate the column. The solution was recycled through the column at 5 ml/min of flow. The concentration of BGG was monitored by the UV monitor at 280 NM. When the column reached the saturation point, the A280 leveled off. The column was washed with equilibration buffer until A280 returned to baseline. With the extinction coefficient of BGG being =1.3, the capacity was expressed as follows:

$$\frac{\text{capacity of BGG adsorbed}}{\text{gram of pad}} = \frac{A^{280} \times \text{total volume}}{1.3} \text{ divided by total weight of the pad}$$

The pH effect on the capacity of the cationic exchange filter No. Cat. #1 and Cat. #2 are shown in Table 8.

TABLE 8

| Pad Weight | Column Size | pH | Adsorption Condition Flow Rate | WP psi | Capacity on BSA Mg/g |
|---|---|---|---|---|---|
| 3.29 g | 25 mm × 7 pads | 5.5 | 2 ml/min | 8 | 837 |
| 3.29 g | 25 mm × 7 pads | 6.0 | 2 ml/min | 8 | 960 |
| 2.21 g | 25 mm × 4 pads | 6.5 | 2 ml/min | 0 | 665 |
| 2.03 g | 25 mm × 4 pads | 7.0 | 2 ml/min | 1 | 530 |
| 2.11 g | 25 mm × 4 pads | 7.5 | 2 ml/min | 0 | 215 |

Conclusions for Example 10

A cationic exchanger with high capacity has been developed, as tested by adsorption of Bovine gamma globulin. High flow rate applicable for large scale industrial operations can be attained.

The system is basically a composite structure with cellulose fiber as supporting backbone and an acrylic polymer carrying glycidyl groups covalently linked to the backbone. These groups are converted to corresponding anionic functional groups through various types of oxidation.

As long as the lignin content is kept low, the reaction between cellulose and the polymer will proceed according to the conditions covered in this Example.

Example 11

Cellulose Grafted with Polymethacrylic Acid (a) Recipe

| Reagent | Quantity |
|---|---|
| Cotton linter fiber | 36 g |
| Methacrylic acid (or B-carboxyethyl acrylate) | 90 ml |
| Glycidyl Methacrylate | 9 ml |
| Triton X-100 | 54 g |
| Sodium Lauryl Sulfate | 1.5 g |
| Ammonium Persulfate | 9.8 g |
| Sodium Thiosulfate | 9.8 g |
| Tributyl Amine | 1.0 ml |

(b) Procedure

1. Disperse 36 g of cotton linter fiber in 2 liters of water and add Tributyl Amine.
2. Add mixed surfactants: nonionic Triton X-100 (from Rohm & Haas) and Sodium Lauryl Sulfate (from Alcolac).
3. Add mixed monomers: methacrylic acid and glycidyl methacrylate, and raise temperature to 40° C.
4. Add catalyst mixture: ammonium persulfate and sodium thiosulfate pre-dissolved in water.
5. Raise temperature to 80° C. for 1 hour under strong agitation.
6. Let the reaction cool to room temperature, and wash with 4 columns of de-ionized water.
7. Wash with methyl alcohol once, and again wash with water to remove alcohol.
8. Adjust the pH by adding 0.1M alkaline solution.

(c) Results

The capacity test conducted by the beaker method by contacting positively charged protein molecules with the media of this example give the following results:

TABLE 9

| Protein Molecules Adsorbed | pH of Solution and Buffer Nature | Capacity |
|---|---|---|
| Bovine Gamma globulin | pH = 6.5 in Acetate buffer | 300 mg/g |
| Hemoglobin | pH = 6.5 in Acetate buffer | 700 |
| Lysozyme | pH = 7.4 in 0.01 M Phosphate buffer | 750 |
| Bovine Serum albumin | pH = 4.6 in Acetate buffer | 85 mg/g |

Examples 12–16

These examples show the use of the carrier of the invention in a fibrous matrix shaped into a jelly-roll form and in cartridge configuration.

Example 12

Separation of Protein Mixtures by DEAE Cartridges

In this example, it is demonstrated that DEAE "jelly-roll" cartridges, like columns, can be utilized to separate protein mixtures with a high degree of resolution. Unlike columns, the cartridges have no undesirable pressure problems and can therefore be operated at a high flow rate with a low pressure drop. In fact, out of 15 cartridges tested, all units gave reproducible and comparable results.

Experiment A shows the separation of an artificial mixture of bovine gammaglobulin and bovine albumin. Experiment B shows the fractionation of human plasma. Cartridges (diameter 2.5 cm, height 7.5 cm) were used in both of these experiments.

Experiment A

Protein: A mixture of two subclasses of gammaglobulin (483 mg) and bovine serum albumin (432 mg)
Buffers: Buffer A: Phosphate buffer (0.01M) at pH=6.8; Buffer B: Phosphate buffer (0.05M) at pH=6.0; Buffer C: Phosphate buffer (0.05M) at pH=6.2+1M NaCl 282 mg gammaglobulin Type I (100% pure) was eluted with 1M NaCl in Buffer A (Peak A in FIG. 3).

Figure 3:
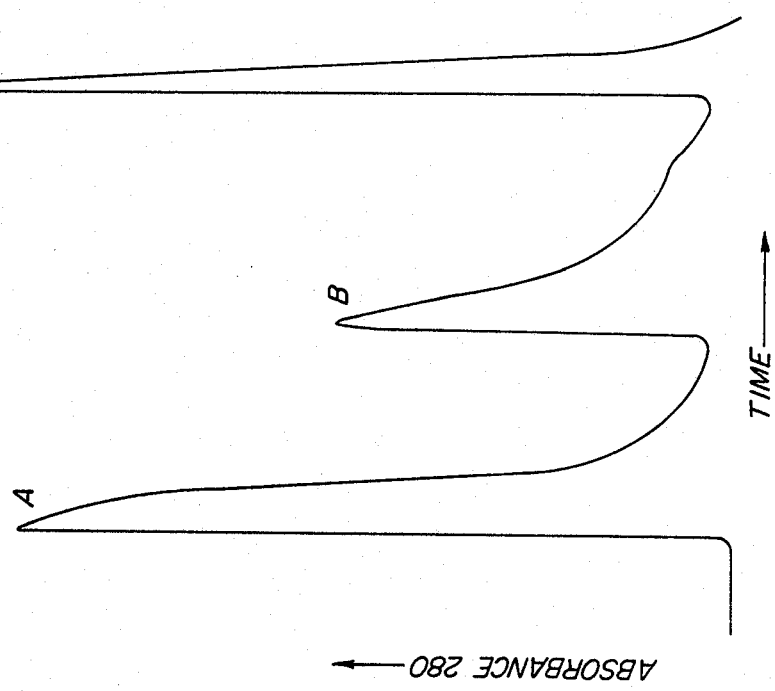
FIG. 3 shows the separation of gamma globulin type I (A), gamma globulin type II (B), and albumin (C), as per Example 10.

148 mg gammaglobulin Type II (approximately 90% purity) was eluted in Buffer B (Peak B in FIG. 3).

Albumin (95% purity) was eluted in Buffer C (Peak C in FIG. 3).

Experiment B

Protein: 10 mL plasma, pH=6.8 (adjusted pH)
Gradient elution: 0.1M phosphate buffer (pH=6.8 to 4.5)
Peak I: gammaglobulin
Peak II: transferrin
Peak III: albumin
Electrophoretic studies indicate that the fractions are at least 90% pure.

Yield and Recovery

| Protein applied | |
|---|---|
| 10 mL plasma total O.D.$_{280}$ = | 390 |
| gammaglobulin O.D.$_{280}$ = | 59.4 |
| transferrin, O.D.$_{280}$ = | 44.0 |
| albumin, O.D.$_{280}$ = | 163.0 |
| Other eluted proteins = | 84.06 |
| | 350.46 |
| Yield = | 88% |

Example 13

Elution Bound Transferrin by pH Shift Using DEAE Cartridge

DEAE ("jelly-roll") cartridge media reduces protein binding capacities at a more alkaline pH than 7.0. This unique pH shift has been utilized to elute bound proteins at higher pH without the use of salts and subsequent dialysis or ultrafiltration.

Figure 4:
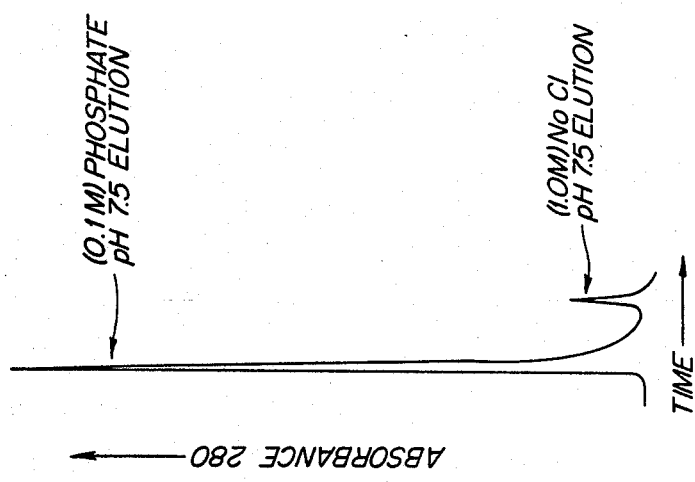
FIG. 4 shows results obtained in the elution of bound transferrin by pH shift using a DEAE cartridge, as per Example 11.

A previous study had shown that 85.4% bound BSA was eluted with (0.1M) phosphate at pH 7.5. In the present example, a similar observation was found with transferrin. Transferrin was bound to a DEAE cartridge media with a (0.01M) phosphate buffer at pH=6.8, and eluted with (0.01M) phosphate, pH=7.5. 92% bound transferrin was eluted in one column volume. The remaining transferrin was eluted with (0.1M) phosphate pH=7.5 and (1M) NaCl. FIG. 4 shows the results.

Example 14

Use of DEAE and CM Cartridges for IgG Fractionation

1. DEAE Cartridge ("Jelly-Roll")
Applied Protein: Dialyzed human plasma
Binding Conditions: Phosphate Buffer (0.01M:0.9–1.2 mS) pH=6.3
Elution Conditions (continuous or step is usable):

| | [Buffer] | Conductivity | pH |
|---|---|---|---|
| IgG | 0.01 M | 1.0 mS | 6.8 |
| Transferrin | 0.025 M | 1.75 mS | 6.04 |
| Albumin | 0.06 M | 3.85 mS | 5.14 |

2. CM Cartridge ("Jelly-Roll")
Applied Protein: Unbound IgG from previous DEAE step
Binding Conditions: Phosphate Buffer (0.01M:0.9–1.2 mS) pH=6.0
Elution Conditions:

| | [Buffer] | pH | [Salt] |
|---|---|---|---|
| IgG | 0.01 M | 6.3 | 1 M |

Example 15

CM Cartridge Capacity at Different pH Values

Figure 5:
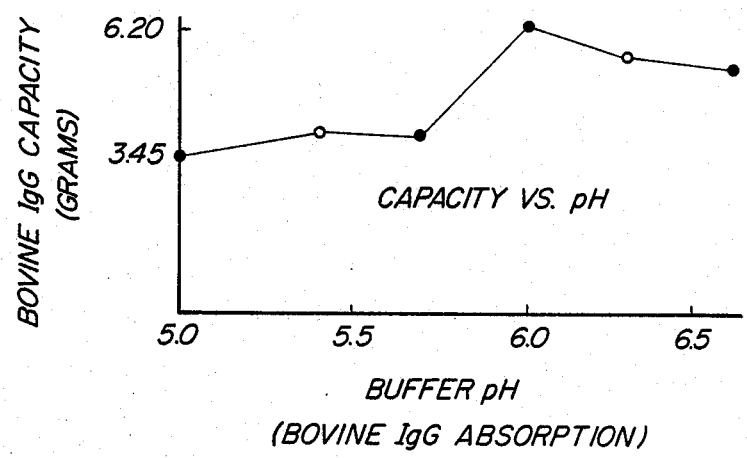
FIG. 5 shows the adsorption capacities for bovine IgG at various pH's as per Example 13.

Comparative studies were made with a CM Cartridge ("jelly-roll") and commercial Whatman ® CM-52. Details are shown on FIG. 5 and Tables 10 and 11.

TABLE 10

Invention Cartridge

| Buffer pH | Elution Condition | Cartridge Bovine IgG Capacity | Recovery (%) |
|---|---|---|---|
| Phosphate (0.01 M) pH = 6.6 | Phosphate (0.05 M) pH = 6.3 (1 M) NaCl | 5.43 g | 94 |
| Phosphate (0.01 M) pH = 6.3 | Phosphate (0.05 M) pH = 6.3 (1 M) NaCl | 5.96 g | 96 |
| Phosphate (0.01 M) pH = 6.0 | Phosphate (0.05 M) pH = 6.3 (1 M) NaCl | 6.2 g | 100 |
| Phosphate (0.01 M) pH = 5.7 | Phosphate (0.05 M) pH = 6.3 (1 M) NaCl | 3.8 g | 99 |
| Acetate (0.02 M) pH = 5.4 | Acetate (0.2 M) pH = 6.3 (1 M) NaCl | 3.9 g | 100 |
| Acetate (0.02 M) pH = 5.4 | Acetate (0.2 M) pH = 6.3 (1 M) NaCl | 3.9 g | 100 |
| Acetate (0.02 M) pH = 5.0 | Acetate (0.2 M) pH = 4.0 (1 M) NaCl | 3.45 g | 98 |

TABLE 11

Whatman cm-52 ®

| Buffer pH | Nature of Matrix | Column Dimension | Adsorption Condition | Elution Condition | Bovine IgG Capacity (mg/g) | Recovery (%) |
|---|---|---|---|---|---|---|
| Phosphate (0.01 M) pH = 6.5 | Microgranules preswollen | (a) 21 mL (b) 16 mm (dia.) | 2 mL/min. | Phosphate (0.05 M) (1 M) NaCl | 1.71 g | 42 |
| Phosphate (0.01 M) pH = 6.0 | Microgranules preswollen | (a) 21.5 mL (b) 16 mm (dia.) | 2 mL/min. | Phosphate (0.05 M) (1 M) NaCl | 4.48 g | 89 |
| Phosphate (0.01 M) pH = 5.5 | Microgranules preswollen | (a) 22 mL (b) 16 mm (dia.) | 2 mL/min. | Phosphate (0.05 M) (1 M) NaCl | 7.8 g | 87.6 |

Example 16

Plasma Fractionation Using Quaternized Media Cartridges

Figure 6:
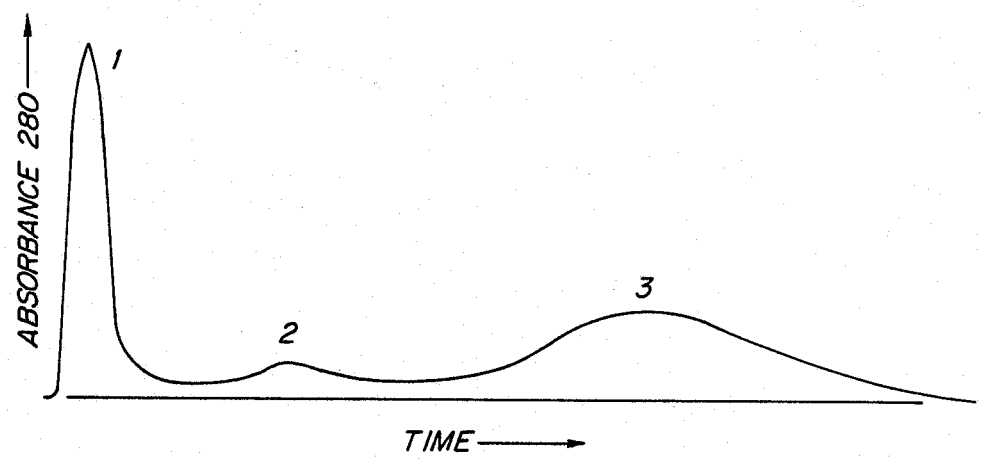
FIG. 6 shows plasma fractionation using a quaternized cartridge medium as per Example 14.

Cartridge dimensions: 2.5 cm (dia.)×7.5 cm (height)
Protein: 10 mL plasma, pH=6.8
Gradient: Continuous phosphate buffer (0.01M), pH=7.3 to (0.2M), pH=4.5
Material
Input: 10 mL plasma, total O.D.$_{280}$=400
Output: Total O.D.$_{280}$=377
Yield: 94.25%
Results are shown on FIG. 6.

Example 17

Invention Media Containing Hydrophobic Groups (a) Recipe

| Poly(n-octylacrylate)-g-Cellulose | |
|---|---|
| Reagent | Quantity |
| Refined pulp (+260) | 20 g |
| n-octyl acrylate | 50 ml |
| Glycidyl methacrylate | 5 ml |
| Ammonium persulfate | 2 g |
| Sodium thiosulfate | 2 g |
| Water | 933 cc |

(b) Procedure

1. Refined pulp (+260) was well dispersed in water in a 3 neck, 3 liter round flask.

2. n-octyl acrylate and glycidyl methacrylate were well mixed before pouring into the reactor.

3. After pouring monomers into the reactor and mixing the reaction mixture well, ammonium persulfate and sodium thiosulfate solutions were charged into the reactor at room temperature.

4. The reaction mixture was strongly agitated and the reaction temperature was raised to 82° C. within 15 minutes.

5. Stirring was maintained for 1 hour in the temperature range of 80°–85° C.

6. After cooling down the reaction mixture, the product was washed well with water.

Example 18

Invention Media Containing Chelating Groups

Poly(3-N,N-dicarboxymethyl-2-hydroxy-propyl methacrylate)-g-cellulose (a) Recipe

| Reagent | Quantity |
|---|---|
| Refined pulp (+260) | 50 g |
| Glycidyl methacrylate | 12.5 cc |
| Ammonium persulfate | 0.5 g |
| Sodium thiosulfate | 0.5 g |
| Sodium iminodiacetate | 2 g |
| Water | 250 cc |

(b) Procedure

1. Refined pulp (+260) was well dispersed in 800 cc water in a 3 neck reactor.

2. After pouring glycidyl methacrylate into the reactor and mixing the reaction mixture well, ammonium persulfate and sodium thiosulfate were charged into the reactor at room temperature.

3. The reaction mixture was strongly agitated, and the reaction temperature was raised to 80° C. within 15 minutes.

4. Stirring was maintained for 1 hour in the temperature range of 80°–85° C.

5. The reaction mixture was cooled to 60° C., and then sodium iminodiacetate was charged into the reactor. Further reaction was continued for 26 hours.

6. The reaction mixture was cooled, and product was filtered and washed.

Example 19

Effect of Polymer Composition on Protein Adsorption Capacity

| Exp. No. | Polymer Composition % GMA as Coupler | % DEAEMA as Functional Groups | Method of Polymer Formation | BSA Adsorption Capacity mg/g media |
|---|---|---|---|---|
| 1 | 16% | 84% | *10% Surfactant | 650 |
| 2 | 14 | 86 | *10% Surfactant | 854 |
| 3 | 12 | 88 | *10% Surfactant | 1,106 |
| 4 | 10 | 90 | *10% Surfactant | 1,446 |
| 5 | 8 | 92 | *10% Surfactant | 1,548 |
| 6 | 6 | 94 | *10% Surfactant | 1,620 |
| 7 | 4 | 96 | *10% Surfactant | 972 |
| 8 | 2 | 98 | *10% Surfactant | 280 |
| 9 | 83 | 91.7 | Without Surfactant | 980 |
| 10 | 10 | 90 | Without Surfactant | 1,450 |
| 11 | 12.5 | 87.5 | Without Surfactant | 1,650 |

*10% surfactant (Lauryl Alcohol Ethoxylate) on the basis of cellulose weight forms latex type polymer.

The results indicate that either increasing or decreasing the GMA composition too much beyond the range of 4 to 12% by weight decreases the adsorption capacity. Values of GMA higher than about 12% cause a decrease in porosity, whereas values lower than about 4% cause losses in grafting efficiency.

Example 20

Polyionene With OH Groups As Coupler

Case A: Introducing OH through Amine Monomers.

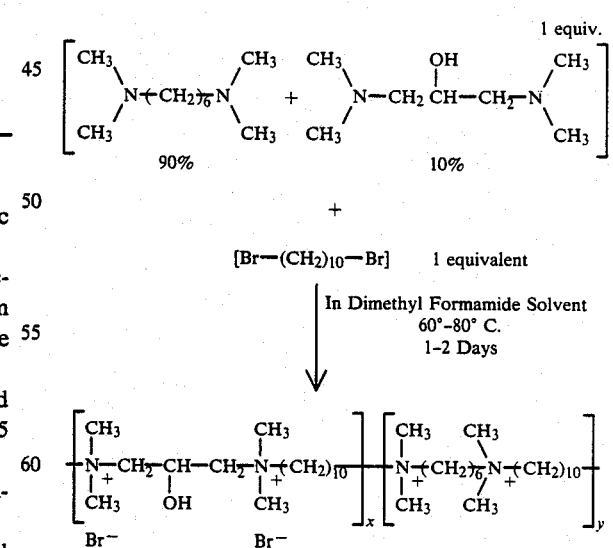

This OH group will serve as coupler to be linked on to membrane structure. Reaction with epichloro hydrin produces an epoxy group in place of the hydroxyl group based on the following reaction:

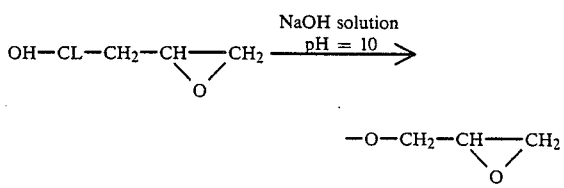
Case B: Introducing OH through Halide Monomers.
The polymer was precipitated out from the dimethyl formamide solvent with acetone and washed with acetone and stored in powder form.
Example 21
Polyionene With Chloro Groups As Coupler
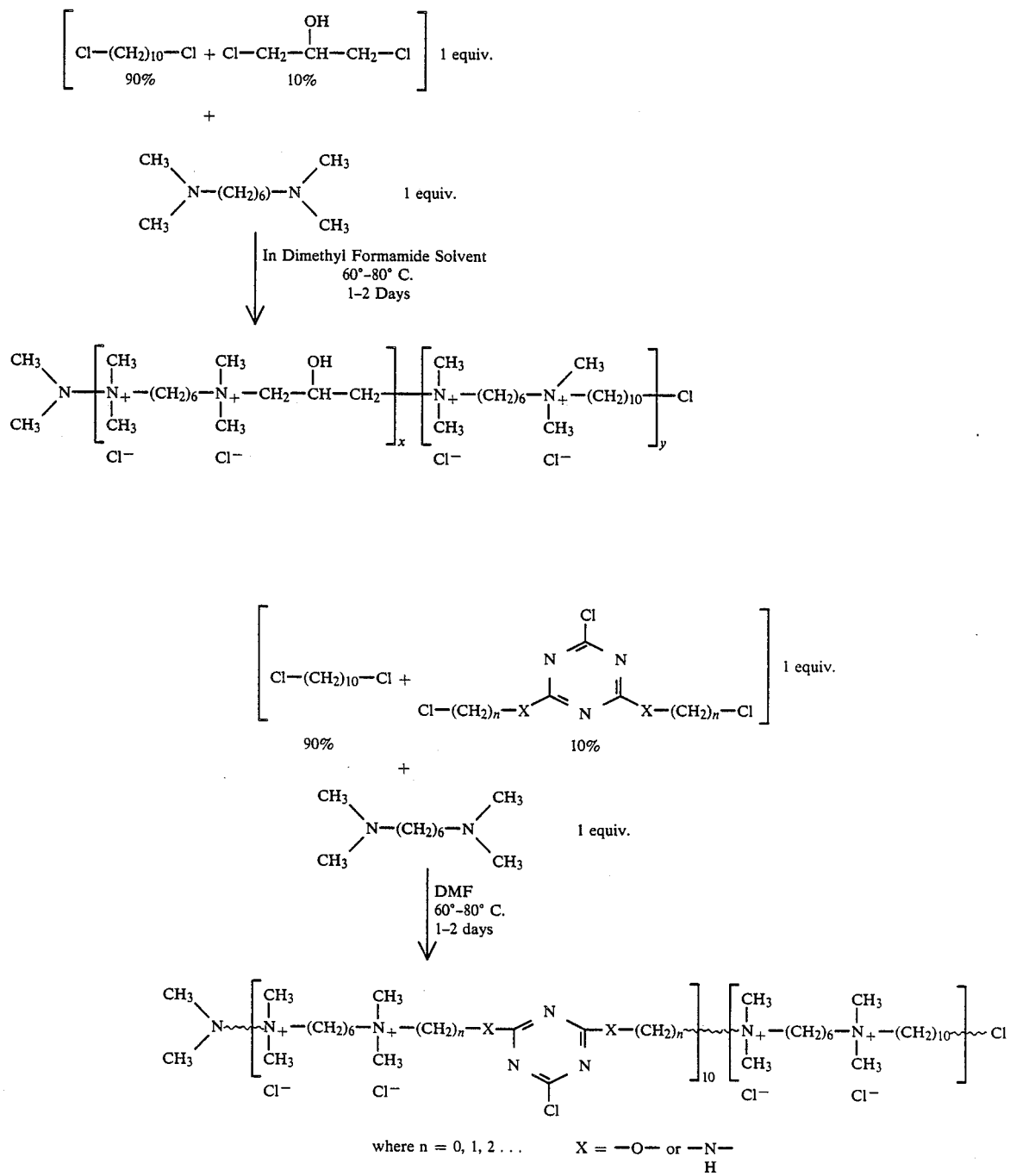

Example 22
Polyionene With Aldehyde or Amine Groups As Coupler

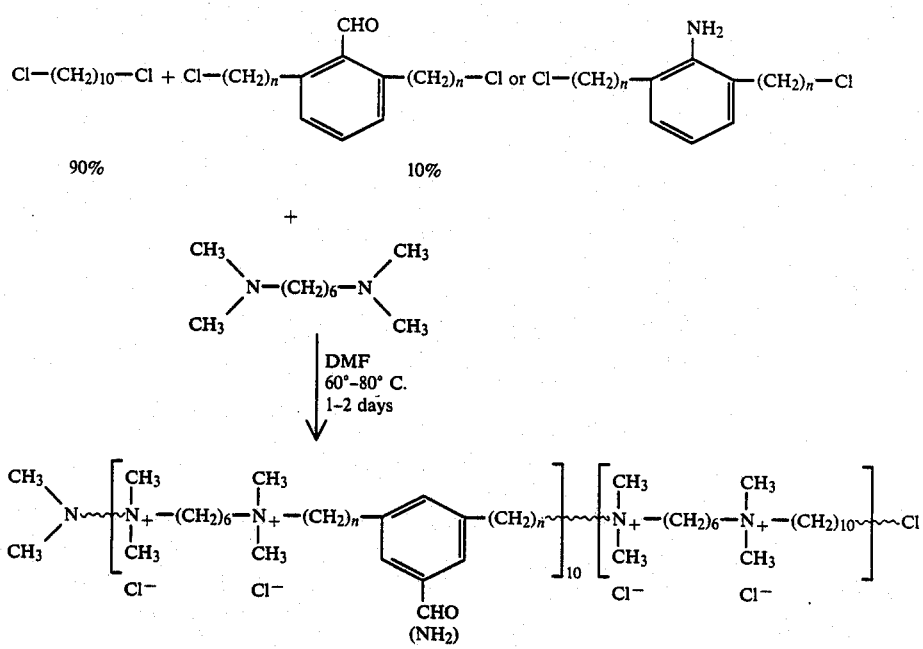

Example 23
Polyionene Carrying Vinyl Groups For Grafting

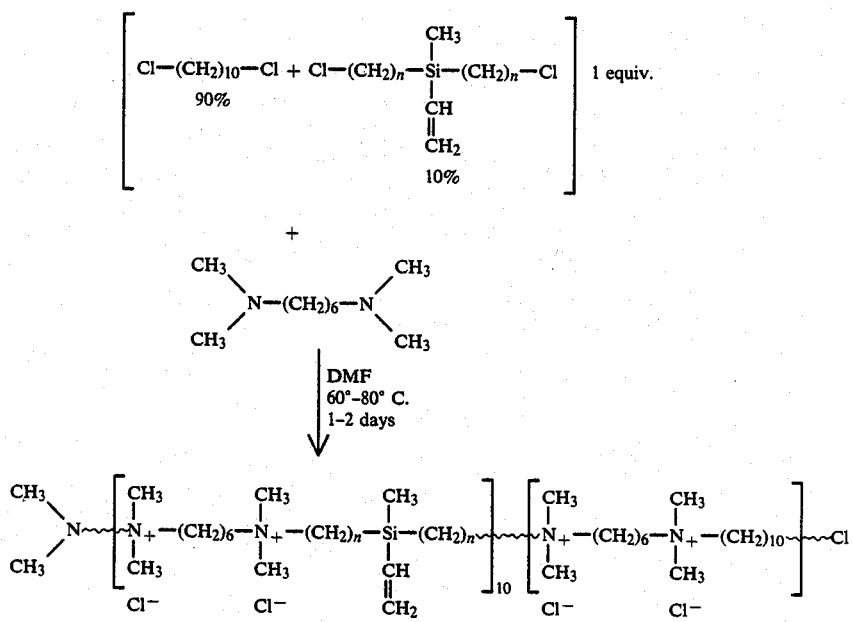

With the introduction of vinyl groups to polyionene, the polymer may be grafted by the free radical reaction to the modified substrate.

Example 24
Incorporating Polyionenes into a Cellulosic Matrix through a Cross-Linked Agent (a) Formulation of the slurry Cellulosic fibers were dispersed in a tank at 1 to 2% consistency to form a slurry. Polyionene of 30% concentration to the weight of cellulose was added to the slurry, followed by addition of 1% each of 1, 4 butanediol diglycidyl ether and tetraethylene pentamine as cross-linking agent. Agitation was continued for 10 minutes.

(b) Formation of TSM (thin sheet media)

The slurry was then cast onto a foraminous surface, vacuum felted, and dried in a conventional manner. The flat, dimensionally stable sheet of polyionene-transformed cellulose was then cut to the appropriate dimensions for each type of column.

Example 25

Covalent Bonding of Polyionene Carrying Hydroxyl Groups to GMA-Modified Cellulose (a) GMA-modified cellulose was formed according to Example 3 to introduce epoxy groups on cellulosic matrix.

(b) Polyionene carrying hydroxyl groups to be covalently bonded to the cellulosic matrix was formed according to Example 20 (Case A).

(c) A slurry was formed in the same manner as described in Example 24.

(d) TSM was formed in the manner described in Example 24.

Example 26

Covalent Bonding of Polyionene Carrying Chloride Groups to GMA-Modified Cellulose (a) The GMA-modified cellulose of Example 3 was reacted with ethylene diamine at 50° C. for 1 hour.

(b) Polyionene carrying chloride groups was prepared according to Example 21.

(c) Slurry and TSM were formed in the same manner as above.

Bacterial Removal Test

Example 27

Removal of Salmonella Typhimurium G-30 Strain Cells in Saline Solution (a) Each column (13 mm) contained 0.25 g media pad was washed with 30 mls of saline prior to use.

(b) G-30 cells were grown in PPBE media, spun down and suspended in saline to a final $OD_{600}$ of 0.256 ($1.3 \times 10^8$ cells/ml). PPBE media was made by mixing 10 g protease peptone #3 with 1 g beef extract and 5 g NaCl in 1 liter of water.

(c) 60 mls were passed through each column at a flow rate of 1 ml/min and 10 ml fractions were collected. $OD_{600}$ readings were used to determine the percentage of cells in each fraction.

Columns tested:
1 Control #1—cellulose;
2 Control #2—cellulose and diepoxide as cross-linker;
3 Media made as example 24 with 30% polyionene;
4 Media made as example 2 with 10% of polyionene;
5 Media made as example 2 with 30% of polyionene;

By taking the original $OD_{600}$ reading of 0.256 corresponding to $1.3 \times 10^8$ cells/ml, the reduction of $OD_{600}$ should represent the relative amount of bacteria cells removed by separation media. FIG. 17 shows the efficiency of the bacteria removal by the separation media made above.

Example 28

Removal of Bacteria Salmonella Typhimurin G-30 in the Presence of Human Serum

Each column (13 mm) contained 0.25 g media and was washed with 30 mls of saline prior to use. Serum and bacteria: G-30 cells were diluted in serum and some $C^{14}$ labeled G-30 cells were added (in case serum interferred with $OD_{600}$ readings).

→ph=7.8
$OD_{280}$=45.7/ml
$OD_{600}$=0.227/ml (~$1.14 \times 10^8$ cells/ml)
CPM/ml=15165 cpm/ml 60 mls were passed through each column at a flow rate of 1 ml/min and 10 ml fractions were collected. $OD_{600}$ readings were used to determine the percentage of cells in each fraction and $OD_{280}$ readings were used to determine the percentage of protein in each fraction. Two separation media were tested, No. 1 was made according to Example 25 with 10% polyionene and No. 2 with 30% polyionene. The results shown in FIG. 18 indicate that the polyionene-transformed modified cellulose works effectively for bacteria removal in the presence of human serum. It is also important to notice that the loss of protein components in serum is negligibly small as shown from the $OD_{280}$ measurement, whereas the removal of bacteria cells measured at $OD_{600}$ is quite significant under the test conditions specified in the figure.

Example 29

Test on Bacteriocidal Effect of Polyioene Bonded Filter

The bacteria removal of the two filters tested in Example 28 were further tested on their ability to stop the growth of salmonella typhimurim G-30 in the following manner.

(a) PPBE media was prepared as described in Example 27 and mixed with 15 gram Agar with 0.2% galactose to form PPBE galactose plate.

(b) A sufficient number of bacteria cells were spread on the plate to produce a lawn after an overnight incubation at 37° C.

(c) Disks of few mm size were made from the bacteriocidal filter made according to Example 25, and placed on top of the galactose plates. If the separation media inhibits the growth of the cells, there should be a clear ring of no growth around the disk. The more potent the bacteriocidal effect, the larger the diameter of the ring around the spot.

(d) Both the separation media showed clear ring spots, indicating the bacteriocidal effect of such media.

Example 30

Effect of Column Length on Bacterial Removal

The effect of column length on bacterial removal is shown in FIG. 19. The filter applied in this test was fabricated according to Example 25 with 10% polyionene. The test conditions were conducted as specified in Example 27.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A polyionene-transformed modified polysaccharide separation matrix comprising a modified polysaccharide having a synthetic polymer covalently coupled thereto and a polyionene bonded to said modified polysaccharide.

2. A separation apparatus for effecting separation of microorganism-originated contaminants from a sample flowing therethrough comprising:
   at least one solid stationary phase;
   a means for radially distributing the sample through the stationary phase;
   wherein the stationary phase comprises:

(a) a swellable fibrous matrix in sheet form spirally wound around the longitudinal axis of the solid phase to form a plurality of layers around the axis;

(b) a spacer means between each layer for permitting controlled swelling thereof and enhancing the distribution of sample flowing radially through the stationary phase, and further wherein the swellable fibrous matrix in sheet form comprises a polyionene-transformed separation matrix of claim 1.

3. A separation apparatus for effecting separation of micro-organism originated contaminants from a sample folowing therethrough comprising:
a housing;
at least one solid stationary phase in said housing, comprising at least one layer of swellable fibrous matrix;
means for distributing said sample through the stationary phase and
means for collecting said sample after the sample has flowed through the stationary phase;
wherein the swellable fibrous matrix in sheet form comprises the polyionene-transformed modified separation matrix of claim 1.

4. A separation apparatus for removing microorganism-originated contaminants from a sample flowing therethrough comprising:
a housing;
at least one solid stationary phase in said housing, comprising:
(a) a plurality of layers of sheets of swellable fibrous matrix and
(b) a spacer means between each said fibrous matrix layer for controlling swelling of the matrix and enhancing the distribution of sample flowing through the stationary phase by substantially evenly dispersing the sample across the matrix;
means for distributing the sample through the stationary phase; and
means for collecting the sample after the sample has flowed through the stationary phase, and wherein said swellable fibrous matrix comprises the polyionene-transformed modified separation matrix of claim 1.

5. A separation apparatus for removing contaminants of microorganism origin from a sample flowing therethrough comprising:
(1) a housing, said housing comprising:
(a) an inlet housing member, and
(b) an outlet housing member, said inlet housing member and said outlet housing member defining a radially, outwardly expanding stationary phase chamber; and
(2) a stationary phase within said radially outwardly expanding stationary phase chamber, said stationary phase chamber comprising at least one layer of a swellable fibrous matrix in sheet form, said swellable fibrous matrix in sheet form comprising the polyionene-transformed modified separation matrix of claim 1.

6. A separation apparatus for removing contaminants of microorganismm origin from a sample flowing therethrough comprising:
(1) a housing, said housing comprising:
(a) an inlet housing member, and
(b) an outlet housing member, said inlet housing member and said outlet housing member defining a stationary phase chamber; and
(2) a stationary phase within said stationary phase chamber, said stationary phase comprising:
(a) a plurality of layers of a swellable fibrous matrix in sheet form;
(b) a spacer means between each layer of said swellable fibrous matrix for permitting controlled swelling thereof and enhancing the distribution of sample flowing through said stationary phase,
wherein said swellable fibrous matrix in sheet form comprises the polyionene-transformed modified separation matrix of claim 1.

7. A separation apparatus for removing contaminants of microorganism origin from a sample flowing therethrough comprising:
(1) a housing, said housing comprising:
(a) an inlet housing member, and
(b) an outlet housing member, said inlet housing member and said outlet housing member defining a radially outwardly expanding stationary phase chamber; and
(2) a stationary phase within said radially, outwardly expanding chamber, said stationary phase comprising:
() a plurality of layers of a swellable fibrous matrix in sheet form, and
(b) a spacer means between each layer of said swellable fibrous matrix for permitting controlled swelling thereof and enhancing the distribution of sample flowing through the stationary phase,
wherein said swellable fibrous matrix in sheet form comprises the polyionene-transformed modified separation matrix of claim 1.

8. The separation apparatus of claim 5 wherein
said inlet housing member comprises a sample inlet means and a sample distribution means, said sample inlet means in communication with said sample distribution means, and
said outlet means comprises a sample collection means and a sample outlet means, said sample collection means in communication with said sample outlet means.

9. The separation apparatus of claim 6 wherein
said inlet housing member comprises a sample inlet means and a sample distribution means, said sample inlet means in communication with said sample distribution means, and
said outlet housing means comprises a sample collection means and a sample outlet means, said sample collection means in communication with said sample outlet means.

10. The separation apparatus of claim 6 wherein
said inlet housing member comprises a sample inlet means and a sample distribution means, said sample inlet means in communication with said sample distribution means, and
said outlet housing means comprises a sample collection means and a sample outlet means, said sample collection means in communication with said sample outlet means.

11. The separation apparatus of claim 8 wherein said sample distribution means comprises radial distribution grooves and concentric distribution channels, said grooves and channels being in communication with each other, and said sample collection means comprises radial collection grooves and concentric collection channels, said radial collection grooves and concentric collection channels in communication with each other.

12. The separation apparatus of claim 9 wherein said sample distribution means comprises radial distribution grooves and concentric distribution channels, said grooves and channels being in communication with each other, and said sample collection means comprises radial collection grooves and concentric collection channels, said radial collection grooves and concentric collection channels in communication with each other.

13. The separation apparatus of claim 10 wherein said sample distribution means comprises radial distribution grooves and concentric distribution channels, said grooves and channels intercommunicating, and said sample collection means comprises radial collection grooves and concentric collection channels, said radial collection grooves and concentric collection channels intercommunicating.

14. The separation apparatus of claims 11, 12 or 13 wherein the volume of said concentric distribution channels and/or said concentric collection channels increases from the interior to the periphery of said column.

15. The separation apparatus of claims 11, 12 or 13 wherein the volume of said radial distribution grooves and/or said radial collection grooves increases from the interior to the periphery of said column.

16. The separation apparatus of claims 8, 9 or 10 wherein said spacer means comprises:
(a) a scrim layer for channeling the sample flow through the matrix and substantially evenly dispersing the sample; or
(b) a mesh layer to provide a spacing between the layers to permit controlled expansion thereof and assist in distributing the sample; or
(c) (a) in combination with (b).

17. The separation matrix of claims 2, 3, 4, 5, 6 or 7 wherein separation matrix is polyionene-transformed cellulose.

18. The separation matrix of claims 2, 3, 4, 5, 6 or 7 wherein said separation matrix comprises
(1) polysaccharide covalently coupled to a synthetic polymer;
(2) said synthetic polymer made from at least on of
(a) a polymerizable compound which has a chemical group capable of direct or indirect covalent coupling to said polysaccharide; and
(b) one or more polymerizable compounds containing
(i) an ionizable chemical group,
(ii) a chemical group capable of transformation to an ionizable chemical group,
(iii) a chemical group capable of causing the covalent coupling of said compound (2) to an affinity ligand or biologically active molecule, or
(iv) a hydrophobic chemical group;
wherein said polyionene comprises a water soluble polymer having polyquaternary ammonium groups separated by hydrophobic groups, said hydrophobic groups comprising aromatic groups or alkyl groups, containing at least six carbon atoms.

19. The separation apparatus of claims 2, 3, 4, 5, 6 or 7 wherein said polyionene has the following repeating units:

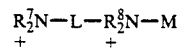

wherein $R^7$ and $R^8$ are $C_1$-$C_4$ alkyl; L is $-(CH_2)_n-P-(CH_2)_m-$; M is $-(CH_2)_o-Q-(CH_2)_p-$, with P and Q being the same or different and representing at least one of $CH_2$, CHA, $C_6H_4$, $C_6H_3A$, $C_6H_4-$CHA$-C_6H_4$, or $R^9C_6H_2A$; wherein A is a reactive group comprising hydrozy, epoxy, amino, halo, aldelyde or carboxy; wherein $R^9$ is $C_1$-$C_4$ alkyl; and m, n, o, and p represent integers of 1 to 20.

20. The separation apparatus of claims 2, 3, 4, 5, 6 or 7 wherein said separation matrix comprises a modified cellulose, said modified cellulose comprising cellulose covalently coupled to a synthetic polymer, said synthetic polymer comprising a homopolymer of glycidyl methacrylate, said modified cellulose transformed by the bonding of a polyionene thereto, said polyionene having the following repeating units:

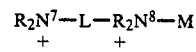

wherein L is $-(CH_2)_6-$ and M contains at least one of $-(CH_2)_{10}-$ and $-CH_2-CHOH-CH_2-$.

21. A polyionene-transformed modified polysaccharide separation matrix which comprises:
(1) polysaccharide covalently coupled to a synthetic polymer;
(2) said synthetic polymer made from at least one of
(a) a polymerizable compound which has a chemical group capable of direct or indirect covalent coupling to said polysaccharide; and
(b) one or more polymerizable compounds containing
(i) an ionizable chemical group,
(ii) a chemical group capable of transformation to an ionizable chemical group,
(iii) a chemical group capable of causing the covalent coupling of said synthetic polymer (2) to an affinity ligand or biologically active molecule, or
(iv) a hydrophobic chemical group;
said modified polysaccharide having bonded thereto, a polyionene.

22. The polyionene-transformed modified polysaccharide separation matrix of claim 21 wherein said polyionene comprises a water-soluble polymer having polyquaternary ammonium groups separated by hydrophobic groups, said hydrophobic groups comprising aromatic groups or alkyl groups, said alkyl groups containing at least six carbon atoms.

23. The polyionene-transformed modified polysaccharide seperation matrix of claim 22 wherein said polyionene has the following repeating units:

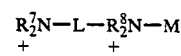

wherein $R^7$ and $R^8$ are $C_1$-$C_4$ alkyl; L is $-(CH_2)_n-P-(CH_2)_m-$; M is $-(CH_2)_o-(CH_2)_p-$, with P and Q being the same or different and representing at least one of $CH_2$, CHA, $C_6H_4$, $C_6H_3A$, $C_6H_4-$CHA$-C_6H_4$, or $R^9C_6H_2A$; wherein A is a reactive group comprising hydroxy, epoxy, amino, halo, aldelyde or carboxy; wherein $R^9$ is $C_1$-$C_4$ alkyl; and m, n, o, and p represent integers of 1 to 20.

24. The separation matrix of claim 22 wherein said polymerizable compound (a) has a chemical group capable of reacting with a hydroxy group of said polysaccharide.

25. The separation of matrix of claim 22 wherein said polysaccharide is fibrous.

26. The separation matrix of claim 22 wherein said polysaccharide is cellulose.

27. The separation matrix of claim 24 wherein said chemical group of said polymerizable compound (a) is a hydroxy reactive O-alkylating chemical agent capable of reacting with the hydroxy group of sad polysaccharide.

28. The separation matrix of claim 27 wherein compound (a) carrying said O-alkylating chemical agent is selected from the group consisting of acrylic anhydride, methacrylic anhydride, -iodo $C_2$-$C_6$ alkyl ester of acrylic acid, -iodo $C_2$-$C_6$ alkyl ester of methacrylic acid, allyl chloride, chloromethyl styrene, chloroacetoxy ethyl methacrylate, glycidyl acrylate, glycidyl methacrylate, 4,5 epoxypentyl-acrylate, 4-(2,3-epoxypropyl)-methacrylate, 9,10-epoxyate arylacrylate, allyl glycidyl ether and ethylene glycol-monoglycidyl ether-acrylate.

29. The separation matrix of claim 21 wherein said synthetic polymer is a homopolymer of glycidyl methacrylate.

30. The separation matrix of claim 22 wherein the polymerizable compound (b) has the formula:

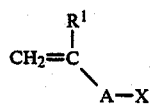

wherein
$R_1$ is H or $CH_3$;
A is CO, or $SO_2$;
X is OH, OM where M is a metal ion, $OR^2$ where $R^2$ is a straight or branched chain $C_1$-$C_{18}$ alkyl group, $OR^3OH$ where $R^3$ is a straight or branched chain $C_2$-$C_6$, alkyl or aromatic group, $NR^4R^5$ or $N+R^4R^5R^6$ where $R^4$, $R^5$ and $R^6$ are the same or different and are hydrogen, $R^2$ or $R^3OH$; or
AX taken together has the formula:

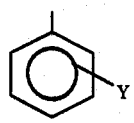

wherein Y is $-CO^2$, $-CH_2CO_2$, $-SO_3$, $-CH_2SO_3$, $PO_4H$, $-CH_2 N(CH_2COO^-)_2$, $-CH_2-NR^4R^5$, or $-CH_2N+R^4R^5R^6$, or the corresponding free acid, $R^2$ or $R^3OH$ ester, or partial ester groups thereof.

31. The separation matrix of claim 22 wherein said polymerizable compound (b) contains a chemical group capable of causing the covalent coupling of said polymerizable compound (b) to an affinity ligand or a biologically active molecule.

32. The separation matrix of claim 31 wherein said polymerizable compound (b) carries an electrophilic functional group capable of covalent reaction with nucleophilic group of said affinity ligand or biologically active molecule.

33. The separation matrix of claim 32 wherein said electrophilic group has the formula (II):

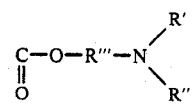

wherein R' and R" are the same or different $C_1$-$C_{18}$ alkyl or alkanoyl radicals or R' and R" together form a 5-7 membered heterocyclic ring with the N atom, and R''' is a direct bond on a $C_2$-$C_3$ alkyl radical.

34. The separation matrix of claim 27 wherein said chemical group capable of causing said covalent coupling carries an epoxy group.

35. The separation matrix of claim 22 wherein the amount of said polymerizable compound (a) in said synthetic polymer is sufficient to cause substantial covalent coupling of the polymer to said polysaccharide, yet insufficient to cause substantial loss of porosity of the modified polysaccharide.

36. The separation matrix of claim 22 wherein said polymer contains more of said polymerizable compound (b) than of said polymerizable compound (a).

37. The separation matrix of claim 36, wherein the ratio of polymerizable compound (b) to said polymerizable compound (a) is about 88-96% by weight of (b) to 4-12% by weight of (a).

38. The separation matrix of claim 23 wherein L is $-(CH_2)_6-$ and M is $-(CH_2)_{10}-$.

39. The separation matrix of claim 23 wherein L is $-(CH_2)_6-$ and M is $-(CH_2)_{10}-$ and $-CH_2-CHOH-CH_2-$.

40. A process for preparing the polyionene-transformed modified polysaccharide separation matrix of claim 21 comprising
    (1) reacting said polysaccharide with the chemical group of compound (a) in said synthetic polymer under temperature conditions sufficient to cause said covalent bonding; and
    (2) bonding a polyionene to the reaction product of (1).

41. A self-supporting cellulosic fibrous matrix comprising
    (1) cellulose covalently coupled to a synthetic polymer; and
    (2) a polyionene reactively bonded to said cellulose.

42. The self-supporting cellulosic fibrous matrix of claim 41 wherein said synthetic polymer comprises at least one of
    (a) a polymerizable compound which has a chemical group capable of direct or indirect covalent coupling to said cellulose; and
    (b) one or more polymerizable compounds containing
        (i) an ionizable chemical group;
        (ii) a chemical group capable of transformation to an ionizable chemical group;
        (iii) a chemical group capable of causing the covalent coupling of said synthetic polymer to an affinity ligand or biologically active molecule, or
        (iv) a hydrophobic chemical group;
and said polyionene comprises a water soluble polymer having polyquaternary ammonium groups separated by hydrophobic groups, said hydrophobic groups comprising aromatic groups or alkyl groups, said alkyl groups containing at least six carbon atoms.

43. The self-supporting matrix of claim 42 wherein said synthetic polymer is homopolymer of glycidyl methacrylate.

44. The self-supporting matrix of claim 42 wherein said polyionene has the following repeating units $$R_2^7 \overset{+}{N} - L - R_2^8 \overset{+}{N} - M$$

wherein $R^7$ and $R^8$ are $C_1$-$C_4$ alkyl; L is —$(CH_2)_n$—P—$(CH_2)_m$—; M is —$(CH_2)_o$—Q—$(CH_2)_p$—, with P and Q being the same or different and representing at least one of $CH_2$, CHA, $C_6H_4$, $C_6H_3A$, $C_6H_4$—CHA—$C_6H_4$, or $R^9C_6H_2A$; wherein A is a reactive group comprising hydroxy, epoxy, amino, halo, aldehyde or carboxy; wherein $R^9$ is $C_1$-$C_4$ alkyl; and m, n, o, and p represent integers of 1 to 20.

45. The self-supporting matrix of claim 44 wherein L is —$(CH_2)_6$— and M is —$(CH_2)_{10}$—.

46. The self-supporting matrix of claim 44 wherein L is —$(CH_2)_6$— and M is —$(CH_2)_{10}$— and —$CH_2$—$CHOH$—$CH_2$—.

47. The matrix of claim 41 which also comprises highly refined cellulose pulp with a Canadian Standard Freeness of between +100 to −600 ml.

48. The matrix of claim 41 which also comprises in addition a particulate substance having chromatographic or molecular separation functionality.

49. The matrix of claim 41 which is in the form of a sheet.

50. A method for removing and inactivating contaminants of a microorganism origin from a biological liquid comprising passing said liquid through a polyionene-transformed modified polysaccharide matrix wherein said modified polysaccharide matrix comprises (1) polysaccharide covalently coupled to a synthetic polymer;
(2) said synthetic polymer made from at least one of
(a) a polymerizable compound which has a chemical group capable of direct or indirect covalent coupling to said polysaccharide; and
one or more polymerizable compounds containing
  (i) an ionizable chemical group,
  (ii) a chemical group capable of transformation to an ionizable chemical group,
  (iii) a chemical group capable of causing the covalent coupling of said compound (2) to an affinity ligand or biologically active molecule, or
  (iv) a hydrophobic chemical group;
said modified polysaccharide having bonded thereto a polyionene, said polyionene comprising a water-soluble polymer having polyquaternary ammonium groups separated by hydrophobic groups, said hydrophobic groups comprising aromatic groups or alkyl groups, said alkyl groups containing at least six carbon atoms.

51. The method of claim 50 wherein said synthetic polymer is homopolymer of glycidyl methacrylate.

52. The method of claim 50 wherein said polyionene has the following repeating units $$R_2^7 \overset{+}{N} - L - R_2^8 \overset{+}{N} - M$$

wherein $R^7$ and $R^8$ are $C_1$-$C_4$ alkyl; L is —$(CH_2)_n$—P—$(CH_2)_m$—; M is —$(CH_2)_o$—Q—$(CH_2)_p$—, with P and Q being the same or different and representing at least one of $CH_2$, CHA, $C_6H_4$, $C_6H_3A$, $C_6H_4$—CHA—$C_6H_4$, or $R^9C_6H_2A$; wherein A is a reactive group comprising hydroxy, epoxy, amino, halo, aldehyde or carboxy; wherein $R^9$ is $C_1$-$C_4$ alkyl; and m, n, o, and p represent integers of 1 to 20.

53. The method of claim 50 wherein said matrix is in the form of a sheet.

54. The method of claim 53 wherein said sheet is in the form of a disc.

55. The method of claim 50 wherein said biological liquid is peripheral blood.

* * * * *